United States Patent
Wolfe et al.

(10) Patent No.: US 9,993,233 B2
(45) Date of Patent: Jun. 12, 2018

(54) LARGE CAPACITY BIOPSY FORCEPS

(71) Applicant: EndoChoice, Inc., Alpharetta, GA (US)

(72) Inventors: Justin Wolfe, Lawrenceville, GA (US); Tracy Knapp, Snellville, GA (US)

(73) Assignee: EndoChoice, Inc., Alpharetta, GA (US)

( * ) Notice: Subject to any disclaimer, the term of this patent is extended or adjusted under 35 U.S.C. 154(b) by 41 days.

(21) Appl. No.: 14/700,345

(22) Filed: Apr. 30, 2015

(65) Prior Publication Data

US 2015/0313581 A1    Nov. 5, 2015

Related U.S. Application Data

(60) Provisional application No. 61/988,172, filed on May 3, 2014.

(51) Int. Cl.
| | | |
|---|---|---|
| *A61B 5/00* | (2006.01) | |
| *A61B 10/06* | (2006.01) | |
| *A61B 10/04* | (2006.01) | |
| *A61B 10/02* | (2006.01) | |

(52) U.S. Cl.
CPC .......... *A61B 10/06* (2013.01); *A61B 10/0233* (2013.01); *A61B 10/04* (2013.01); *A61B 2010/045* (2013.01)

(58) Field of Classification Search
CPC . A61B 10/0233; A61B 10/0266; A61B 10/04; A61B 10/06
USPC .................................. 606/170, 174, 205, 207
See application file for complete search history.

(56) References Cited

U.S. PATENT DOCUMENTS

| | | | | |
|---|---|---|---|---|
| 4,817,630 A | * | 4/1989 | Schintgen | A61B 10/02 600/564 |
| 4,887,612 A | * | 12/1989 | Esser | A61B 10/06 294/116 |
| 5,094,247 A | | 3/1992 | Hernandez et al. | |
| 5,373,854 A | * | 12/1994 | Kolozsi | A61B 10/06 600/562 |
| 6,264,617 B1 | * | 7/2001 | Bales | A61B 10/06 600/564 |
| 7,775,989 B2 | * | 8/2010 | Nakao | A61B 10/06 600/564 |
| 8,313,500 B2 | * | 11/2012 | Weizman | A61B 10/06 140/111 |
| 8,672,859 B2 | | 3/2014 | Timberlake et al. | |
| 8,740,853 B2 | * | 6/2014 | Szweda | A61B 10/06 604/194 |
| 9,072,538 B2 | * | 7/2015 | Suzuki | A61B 17/29 |

FOREIGN PATENT DOCUMENTS

WO    WO 9116856 A1    11/1991

\* cited by examiner

*Primary Examiner* — Max Hindenburg
(74) *Attorney, Agent, or Firm* — Bookoff McAndrews, PLLC

(57) ABSTRACT

Biopsy forceps devices used to obtain tissue samples from a patient using an endoscopic system include larger cup size, longer jaw length, a squared front face, a tapered jaw design, and an offset pivot to enable taking a larger sample size. The forceps include a drive wire attached to the jaws by linkages having pins slidable within slots on the jaws of the forceps, providing the offset pivot point.

13 Claims, 44 Drawing Sheets

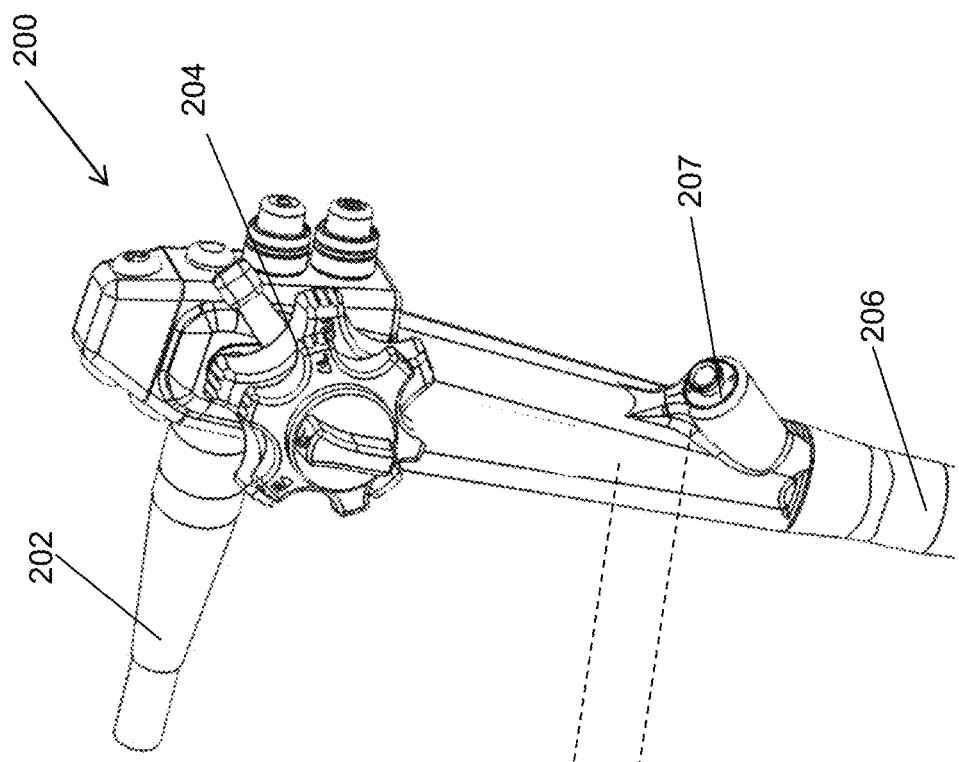
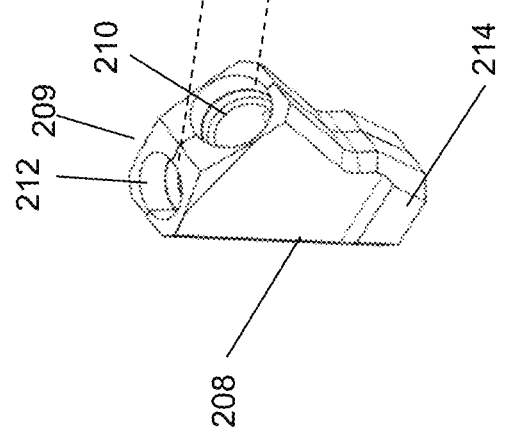
Figure 2A
Figure 2B

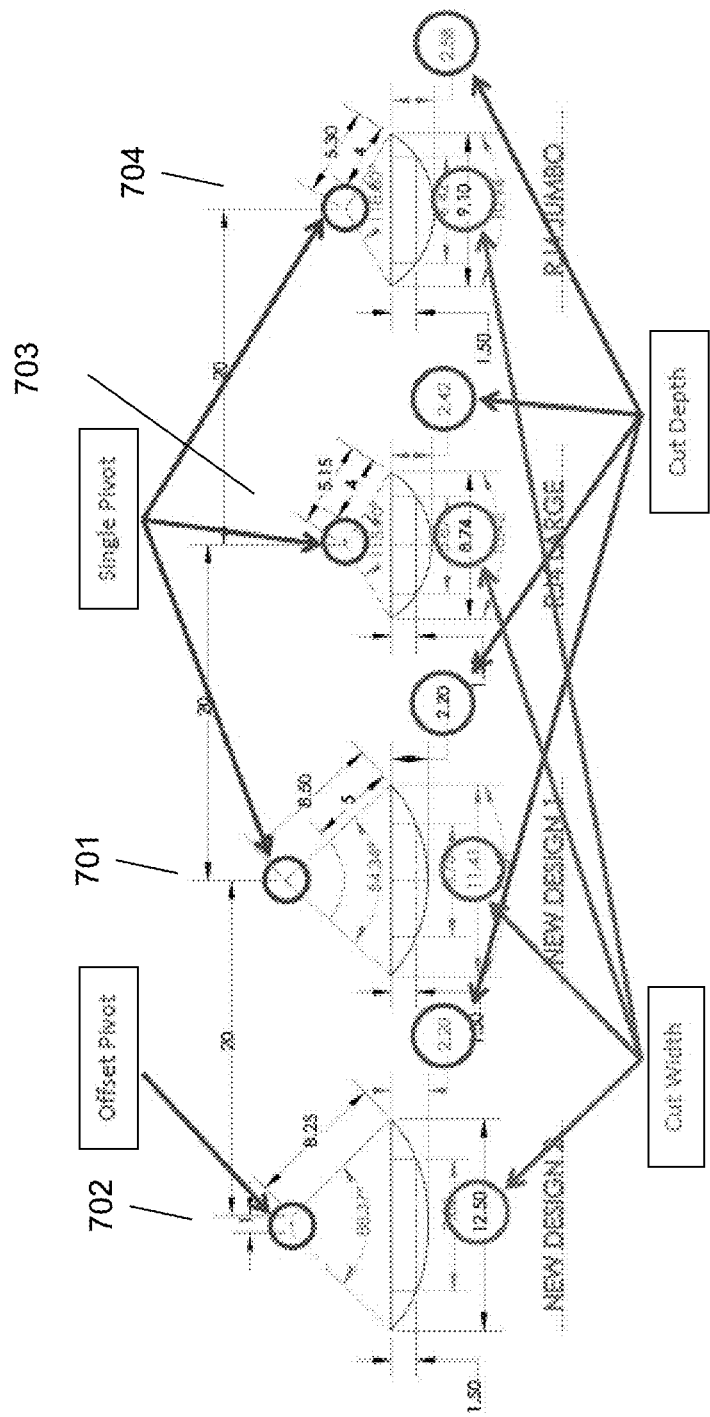
Figure 7 – Comparison of Biopsy Forceps for Sample Size

LARGE CAPACITY BIOPSY FORCEPS

CROSS REFERENCE

The present application relies on U.S. Provisional Patent Application No. 61/988,172, entitled "Large Capacity Biopsy Forceps" and filed on May 3, 2014, for priority. The aforementioned application is hereby incorporated by reference in its entirety.

FIELD

The present specification relates generally to surgical instruments. More particularly, the present specification relates to a biopsy forceps device used to obtain tissue samples from a patient using an endoscopic system, wherein the biopsy forceps is capable of taking a large sample size.

BACKGROUND

Endoscopes have attained great acceptance within the medical community since they provide means for performing procedures with minimal patient trauma while enabling the physician to view the internal anatomy of the patient. Over the years, numerous endoscopes have been developed and categorized according to specific applications, such as cystoscopy, colonoscopy, laparoscopy, upper gastrointestinal endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which includes pathways extending the length of the handle to the endoscope tip, referred to as working or service channels. Various surgical tools may be inserted through a working channel in the endoscope for performing different surgical procedures. The working channel may be accessed via a service channel connector placed within the handle of the endoscope. Usually, service channel connectors comprise a service channel being used for insertion of medical instruments and a suction channel for removing bodily fluids. The two channels within the service channel connector end in a unified working channel that is coupled to an elongated tubular shaft of the endoscope.

Medical tools are generally inserted within a service channel of an endoscope for removing polyps, taking a biopsy of a tissue sample, etc. Typically, a biopsy forceps device is employed for taking a biopsy of a tissue sample of a patient.

Existing products typically use a linkage system that tends to hinder a wider opening of the forceps device. For example, one conventional device (a cam actuated biopsy forceps) includes a single pivot point that moves during the opening and closing of the forceps. The closing movement causes the jaws of the forceps to retract toward the handle (away from the tissue) which can cause issues during sampling.

Hence, there is a requirement for a biopsy forceps device that allows for a larger biopsy sample size within an equivalent device diameter.

SUMMARY

The biopsy device of the present specification comprises a medical tool control handle; a catheter that comprises a tube within which at least one control wire is positioned; and the actual working tool portion itself (the forceps).

The biopsy forceps device allows for a larger biopsy sample size within an equivalent device diameter. The device also creates a shallower cut which reduces the chances of bleeding from the patient or perforation of the patient's inner tissues. In one embodiment, the movement of a needle is integrated, assisting in sample removal. In addition, the biopsy forceps design of the present specification is comprised of a reduced number of components which make the device easier to assemble.

The present specification describes a novel design that includes a cam mechanism which allows for a shorter mechanical motion to operate the device. The biopsy forceps of the present specification includes stationary pivots and thus, the jaws do not retract during closing. The biopsy forceps includes two pivot points and two linkages. The two pivot points reduce jaw mismatch. Further, the combination of the cam mechanism and the linkages allows for a larger opening distance of the forceps. Further, the biopsy needle extends toward the tissue during opening and retracts during closing.

The biopsy forceps of the present specification has a large "cup" size, longer jaw length, a squared front face, a tapered jaw design, and an offset pivot, which lend to a larger sample size.

In operation, the physician inserts the forceps end of the biopsy forceps medical tool (the working part of the medical tool) into the working channel opening, in the scope handle. The physician pushes the tool inside the working channel with the help of a catheter (having a length of at least 200 centimeter). The physician inserts the medical tool until he sees it in the front camera (or side camera if the scope has a side working channel). When the physician sees the forceps in the camera, he directs it to the polyp/abnormality he wishes to cut. The control of the jaws is made with the medical tool control handle as described below.

The biopsy forceps of the present specification is constructed using rigid materials. In some embodiments, the materials include stainless steel and/or rigid polymers, such as polyether ether ketone (PEEK). The primary method of manufacture includes metal injection molding and/or traditional polymer injection molding as well as stamping. There are also a reduced number of components, thus making this device easier to manufacture and assemble compared to prior art devices.

In one embodiment, the present specification describes a biopsy tool device for use with an endoscope, the biopsy tool device comprising: a control handle for manipulating a working portion; a catheter that comprises a tube within which at least one control or drive wire is positioned; and, a forceps portion, wherein the handle is connected to the forceps portion via the catheter. The forceps portion may comprise jaws, wherein said jaws comprise an upper portion and a lower portion; at least one pivot, for enabling movement of the jaws; linkages, wherein said linkages enable movement of the jaws; and a needle.

The linkages and pivots enable the movement of the jaws such that when closed, teeth of the upper portion and lower portion align in an offset position such that a tooth of one jaw portion will fit into a recess formed by two adjacent teeth of another jaw portion.

The forceps portion has at least one of a large cup size, a longer jaw length, a squared front face, a tapered jaw design, and an offset pivot that allow for acquiring a larger sample size.

When the drive wire is retracted using the control handle, the needle portion is also refracted.

The drive wire is optionally attached to a tang on the jaw portion in a 180 degree looped configuration.

The drive wire is optionally attached to the drive wire to a tang on the jaw portion in a 90 degree bent configuration.

The drive wire is optionally attached to a tang on the jaw portion using a rivet.

The drive wire is optionally attached to a tang on the jaw portion using a clip mechanism.

The drive wire is optionally attached to a tang on the jaw portion using a hook mechanism.

The present specification also discloses a biopsy device for use with an endoscope, the biopsy device comprising: a control handle and a drive wire, wherein the control handle is configured to manipulate said drive wire; an elongate tubular portion having a proximal end and a distal end, wherein the control handle is connected to the elongate tubular portion at the proximal end and wherein the drive wire extends from the control handle, through the elongate tubular portion, and to the distal end and wherein the drive wire terminates in a first linkage, a second linkage, and a needle; a first jaw and a second jaw, wherein said first jaw comprises a first plurality of teeth at its distal end and a first longitudinal slot at its proximal end and wherein said second jaw comprises a second plurality of teeth at its distal end and a second longitudinal slot at its proximal end; a coupling unit having a first end and a second end, wherein, at its first end, the coupling unit is attached to said distal end of the elongate tubular portion and wherein, at its second end, the coupling unit comprises: a first pivot point attached to the first jaw and a second pivot point attached to the second jaw, wherein the first pivot point and second pivot point are positioned at a same longitudinal distance along the length of coupling unit and are laterally offset from each other; a third pivot point attached to the first linkage and a fourth pivot point attached to the second linkage, wherein the third pivot point and fourth pivot point are positioned at a same longitudinal distance along the length of said drive wire, are positioned distal to the first pivot point and second pivot point, and are laterally offset from each other; and wherein the first jaw is coupled to the first linkage by a first pin attached to the first linkage and configured to slide within said first longitudinal slot and wherein the second jaw is coupled to the second linkage by a second pin attached to the second linkage and configured to slide within said second longitudinal slot.

The biopsy device may be operable between a first closed configuration and a second open configuration. When in said first closed configuration, said first plurality of teeth and said second plurality of teeth may be aligned so that each of the first plurality of teeth are positioned between each of the second plurality of teeth and each of the second plurality of teeth are positioned between each of the first plurality of teeth, thereby leaving no gaps between said first and second jaws.

The distal ends of said jaws may be rounded.

Distal movement of the drive wire via said control handle may cause said needle to move distally for piercing tissue.

The device may have a minimum cut depth in a range of 2 mm to 3 mm with a maximum cut width in a range of 10 mm to 13 mm A length of each jaw may be in a range of 8 mm to 9 mm.

Optionally, said first jaw further comprises a third longitudinal slot at its proximal end and said second jaw further comprises a fourth longitudinal slot at its proximal end and said first pin is configured to slide within said first longitudinal slot and said third longitudinal slot and said second pin is configured to slide within said second longitudinal slot and said fourth longitudinal slot.

The present specification also discloses a biopsy device for use with an endoscope, the biopsy device comprising: a control handle and a drive wire, wherein the control handle is configured to manipulate said drive wire; an elongate tubular portion having a proximal end and a distal end, wherein the control handle is connected to the elongate tubular portion at the proximal end and wherein the drive wire extends from the control handle, through the elongate tubular portion, and to the distal end wherein the drive wire terminates in a first linkage, a second linkage, and a needle; a first jaw and a second jaw, wherein said first jaw comprises a first plurality of teeth at its distal end and a first opening at its proximal end and wherein said second jaw comprises a second plurality of teeth at its distal end and a second opening at its proximal end; a coupling unit having a first end and a second end, wherein, at its first end, the coupling unit is attached to said distal end of the tubular portion and wherein, at its second end, the coupling unit comprises: a first pivot point attached to the first jaw and a second pivot point attached to the second jaw, wherein the first pivot point and second pivot point are positioned at a same longitudinal distance along the length of coupling unit; a third pivot point attached to the first linkage and a fourth pivot point attached to the second linkage, wherein the third pivot point and fourth pivot point are positioned at a same longitudinal distance along the length of said drive wire and are positioned distal to the first pivot point and second pivot point; and wherein the first jaw is coupled to the first linkage by a first pin attached to the first linkage and configured to rotate within said first opening and wherein the second jaw is coupled to the second linkage by a second pin attached to the second linkage and configured to rotate within said second opening.

The biopsy device may be operable between a first closed configuration and a second open configuration wherein, when in said first closed configuration, said first plurality of teeth and said second plurality of teeth are aligned so that each of the first plurality of teeth are positioned between each of the second plurality of teeth and each of the second plurality of teeth are positioned between each of the first plurality of teeth, thereby leaving no gaps between said first and second jaws.

The biopsy device may have a minimum cut depth in a range of 2 mm to 3 mm with a maximum cut width in a range of 10 mm to 13 mm.

The distal face of said jaws may be squared off.

Distal movement of the drive wire via said control handle may cause said needle to move distally for piercing tissue.

The jaws may have a maximum opening angle in a range of 80 degrees to 100 degrees.

A length of each jaw may be in a range of 8 mm to 9 mm.

Optionally, the biopsy device further comprises at least one clip attached to said first pin and at least one clip attached to said second pin wherein said clips maintain proper positioning of said pins within said openings.

Optionally, said first jaw further comprises a third opening at its proximal end and said second jaw further comprises a fourth opening at its proximal end and said first pin is configured to rotate within said first opening and said third opening and said second pin is configured to rotate within said second opening and said fourth opening.

A width of said jaws may be greater than a height of said jaws portion to provide a wider bite.

The present specification also discloses a biopsy device for use with an endoscope, the biopsy tool device comprising: a control handle and a drive wire, wherein the control handle is configured to manipulate said drive wire; an elongate tubular portion having a proximal end and a distal end, wherein the control handle is connected to the elongate tubular portion at the proximal end and wherein the drive wire extends from the control handle, through the elongate tubular portion, and to the distal end wherein the drive wire terminates in a first linkage, a second linkage, and a needle; a first jaw and a second jaw, wherein said first jaw comprises a first plurality of teeth at its distal end and a first opening at its proximal end and wherein said second jaw comprises a second plurality of teeth at its distal end and a second opening at its proximal end; a coupling unit having a first end and a second end, wherein, at its first end, the coupling unit is attached to said distal end of the tubular portion and wherein, at its second end, the coupling unit comprises: a first pivot point attached to the first jaw and a second pivot point attached to the second jaw, wherein the first pivot point and second pivot point are positioned at a same longitudinal distance along the length of coupling unit and are laterally offset from each other; a third pivot point attached to the first linkage and a fourth pivot point attached to the second linkage, wherein the third pivot point and fourth pivot point are positioned at a same longitudinal distance along the length of said drive wire, are positioned distal to the first pivot point and second pivot point, and are laterally offset from each other; and wherein the first jaw is coupled to the first linkage by a first pin attached to the first linkage and configured to rotate within said first opening and wherein the second jaw is coupled to the second linkage by a second pin attached to the second linkage and configured to rotate within said second opening; and wherein said first linkage includes a first component for attaching said drive wire and said second linkage includes a second component for attaching said drive wire.

The first and second components may comprise openings wherein said drive wire is passed through said openings and looped about, bent over, or riveted to said linkages.

The first and second components may comprise pegs wherein said drive wire is clipped or hooked about said pegs.

The present specification also discloses a biopsy device for use with an endoscope, the biopsy device comprising: a control handle and a drive wire, wherein the control handle is configured to manipulate said drive wire; an elongate tubular portion having a proximal end and a distal end, wherein the control handle is connected to the elongate tubular portion at the proximal end and wherein the drive wire extends from the control handle, through the elongate tubular portion, and to the distal end and wherein the first drive wire terminates in a first linkage, a second linkage, and a needle; a first jaw and a second jaw, wherein said first jaw comprises a first plurality of teeth at its distal end and a first longitudinal slot at its proximal end and wherein said second jaw comprises a second plurality of teeth at its distal end and a second longitudinal slot at its proximal end; a coupling unit having a first end and a second end, wherein, at its first end, the coupling unit is attached to said distal end of the elongate tubular portion and wherein, at its second end, the coupling unit comprises: a first pivot point attached to the first jaw and a second pivot point attached to the second jaw, wherein the first pivot point and second pivot point are positioned at a same longitudinal distance along the length of coupling unit and are laterally offset from each other; a third pivot point attached to the first linkage and a fourth pivot point attached to the second linkage, wherein the third pivot point and fourth pivot point are positioned at a same longitudinal distance along the length of said drive wire, are positioned distal to the first pivot point and second pivot point, and are laterally offset from each other; and wherein the first jaw is coupled to the first linkage only by a first pin attached to the first linkage and configured to slide within said first longitudinal slot and wherein the second jaw is coupled to the second linkage only by a second pin attached to the second linkage and configured to slide within said second longitudinal slot.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 2A illustrates an endoscope handle comprising a service channel port, in accordance with an embodiment of the present specification;

FIG. 2B illustrates a service channel connector, in accordance with an embodiment of the present specification;

FIG. 7 is a diagram showing a comparison of biopsy sample sizes from different forceps devices;

DETAILED DESCRIPTION

Figure 1:
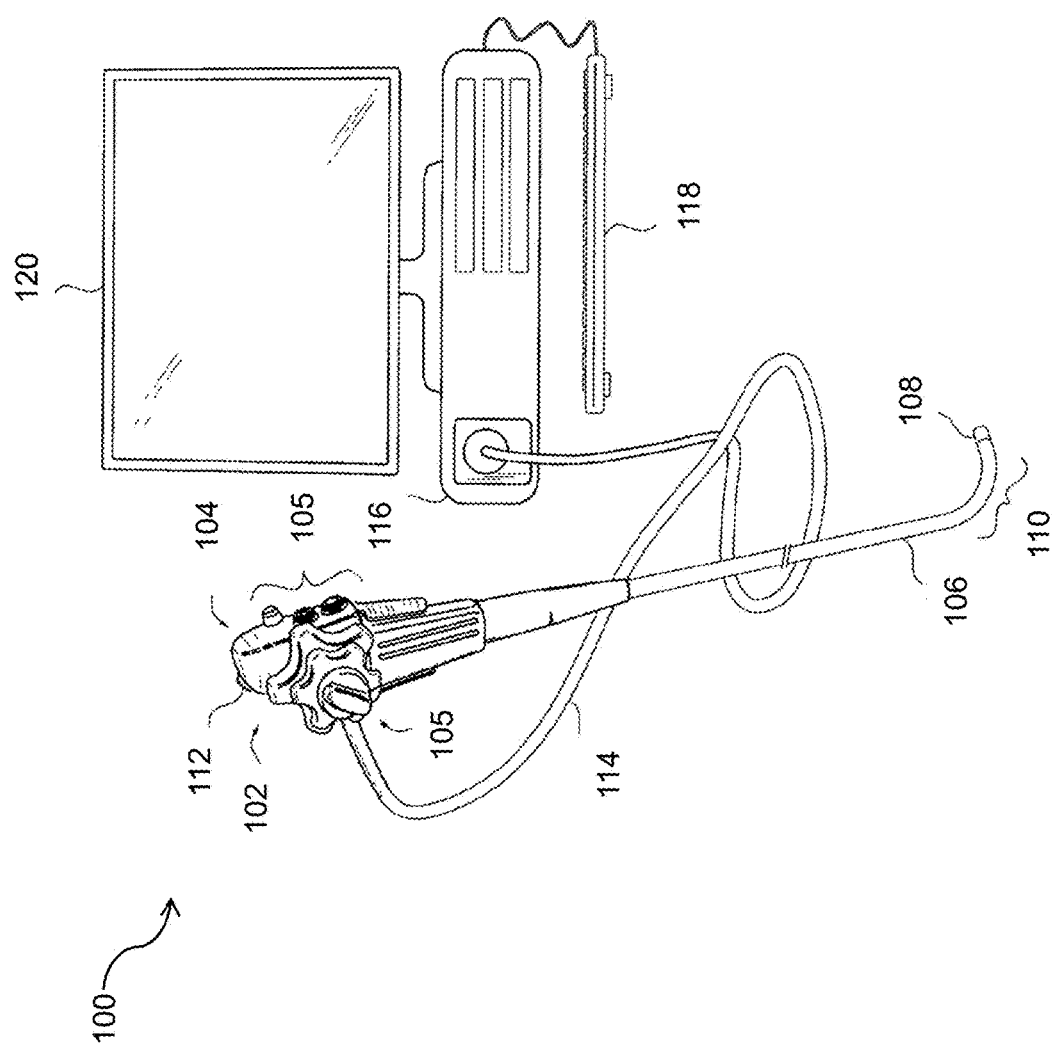
FIG. 1 illustrates a multiple viewing elements endoscopy system in which a service channel connector may be implemented in accordance with an embodiment of the present specification.

A biopsy device is a medical tool that is inserted into a working channel port located within the handle of an endoscope. The biopsy device comprises a medical tool control handle, a catheter that comprises a tube within which at least one control wire is positioned, and the actual working tool portion itself (the forceps).

The present specification describes a biopsy forceps device that allows for a larger biopsy sample size within an equivalent device diameter. The device also creates a shallower cut which reduces the chances of bleeding from the patient or perforation of the patient's inner tissues. In one embodiment, the movement of a needle is integrated, assisting in sample removal. In addition, the biopsy forceps design of the present specification is comprised of a reduced number of components which make the device easier to assemble.

Conventional biopsy forceps designs commonly use a linkage system. The present specification describes a novel structure that includes a cam, which allows for a shorter mechanical motion to operate the device. The biopsy forceps of the present specification includes stationary pivots and, in contrast with certain prior art devices, the jaws do not retract during closing. The biopsy forceps includes two pivot points and two linkages. The two pivot points reduce jaw mismatch. Further, the combination of the cam and linkage system allows for a larger opening. Further, the biopsy needle extends toward the tissue during opening and retracts during closing.

In operation, the physician inserts the forceps end of the biopsy forceps medical tool (the working part of the medical tool) into the working channel opening, in the scope handle. The physician pushes the tool inside the working channel with the help of a catheter (having a length of at least 200 centimeter). The physician inserts the medical tool until he sees it in the front camera (or side camera if the scope has a side working channel). When the physician sees the forceps in the camera, he directs it to the polyp/abnormality he wishes to cut. The control of the jaws is made with the medical tool control handle as described below.

The present specification also describes improved tangs and drive wires for the biopsy forceps device described above. Thus, a new means for attaching the jaws to drive wires is disclosed.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

FIG. 1 illustrates a multiple viewing elements endoscopy system 100 in which the medical tool of the present specification may be used. As would be apparent to persons of skill in the art, the medical tool described in the present specification may be implemented in any endoscope being used for inserting medical instruments into a patient's body.

Reference is now made to FIG. 1 which shows a semi-pictorial view of a multiple viewing elements endoscopy system 100. System 100 may include a multiple viewing elements endoscope 102. Multiple viewing elements endoscope 102 may include a handle 104, from which an elongated shaft 106 emerges. Elongated shaft 106 terminates with a tip section 108 which is turnable or maneuverable by way of a bending section 110. Handle 104 may be used for maneuvering elongated shaft 106 within a body cavity. The handle 104 may include one or more knobs and/or switches 105 which control bending section 110 as well as functions, such as fluid injection and suction and toggling between the multiple viewing elements of tip 108. Tip 108 may include multiple viewing elements. In accordance with an embodiment, tip 108 includes a front viewing element and one or two side viewing elements. In another embodiment, tip 108 may include only a front viewing element.

In addition, tip 108 may include at least one service/working channel exit point. In accordance with an embodiment, tip 108 includes a front service/working channel exit point and at least one side service channel exit point. In another embodiment, tip 108 may include two front service/working channel exit points.

A utility cable 114 may connect between handle 104 and a controller 116. Utility cable 114 may include therein one or more fluid channels and one or more electrical channels. The electrical channel(s) may include at least one data cable for receiving video signals from the front and side-viewing elements, as well as at least one power cable for providing electrical power to the viewing elements and to the discrete illuminators.

Controller 116 may govern power transmission to the endoscope's 102 tip section 108, such as for the tip section's viewing elements and illuminators. Controller 116 may further control one or more fluid, liquid and/or suction pumps which supply corresponding functionalities to endoscope 102. One or more input devices, such as a keyboard 118, a touchscreen display, and/or a computer may be connected to controller 116 for the purpose of human interaction with the controller. In another configuration, an input device, such as a keyboard and/or a touchscreen display may be integrated with the controller in the same casing.

A display 120 may be connected to controller 116, and configured to display images and/or video streams received from the viewing elements of the endoscope 102. Display 120 may further be operative to display a user interface for allowing a human operator to set various features of system 100. Display 120 may further be comprised of a plurality of monitors.

FIG. 2A illustrates an endoscope handle 200 including a Y-shaped service channel connector, in accordance with an embodiment of the present specification. The handle 200 comprises an umbilical tube/utility cable 202 for connecting the endoscope to a main controller, knobs 204 for maneuvering a bending section (not shown) of an insertion tube 206 within a lumen, and a service channel port 207, among other components as described with respect to FIG. 1. The service channel port 207 is positioned within a handle 200 of an endoscope, in the lower, distal portion of the handle 200, close to the insertion tube 206 of the endoscope. The service channel connector (not shown in FIG. 2A) of the present specification is connected to the endoscopic handle via a service channel port 207 and a suction channel and resides within the endoscope handle 200.

FIG. 2B illustrates a service channel connector 208, in accordance with an embodiment of the present specification. As shown, the service channel connector 208 is approximately Y-shaped and, in one embodiment, comprises at its proximal end 209 a service channel opening 210 and a suction channel opening 212. A distal end 214 of the connector 208 is connected to the insertion tube 206 via a working channel opening (not shown). The proximal end 209 is connected to the service channel port 207 of the handle 200 through service channel opening 210 and through a suction channel (not shown) which runs along the umbilical tube and is connected to a suction pump. Medical instruments, such as the biopsy forceps of the present specification, may be inserted through the service channel opening 210 into the insertion tube 206, via the working channel opening.

Figure 3:
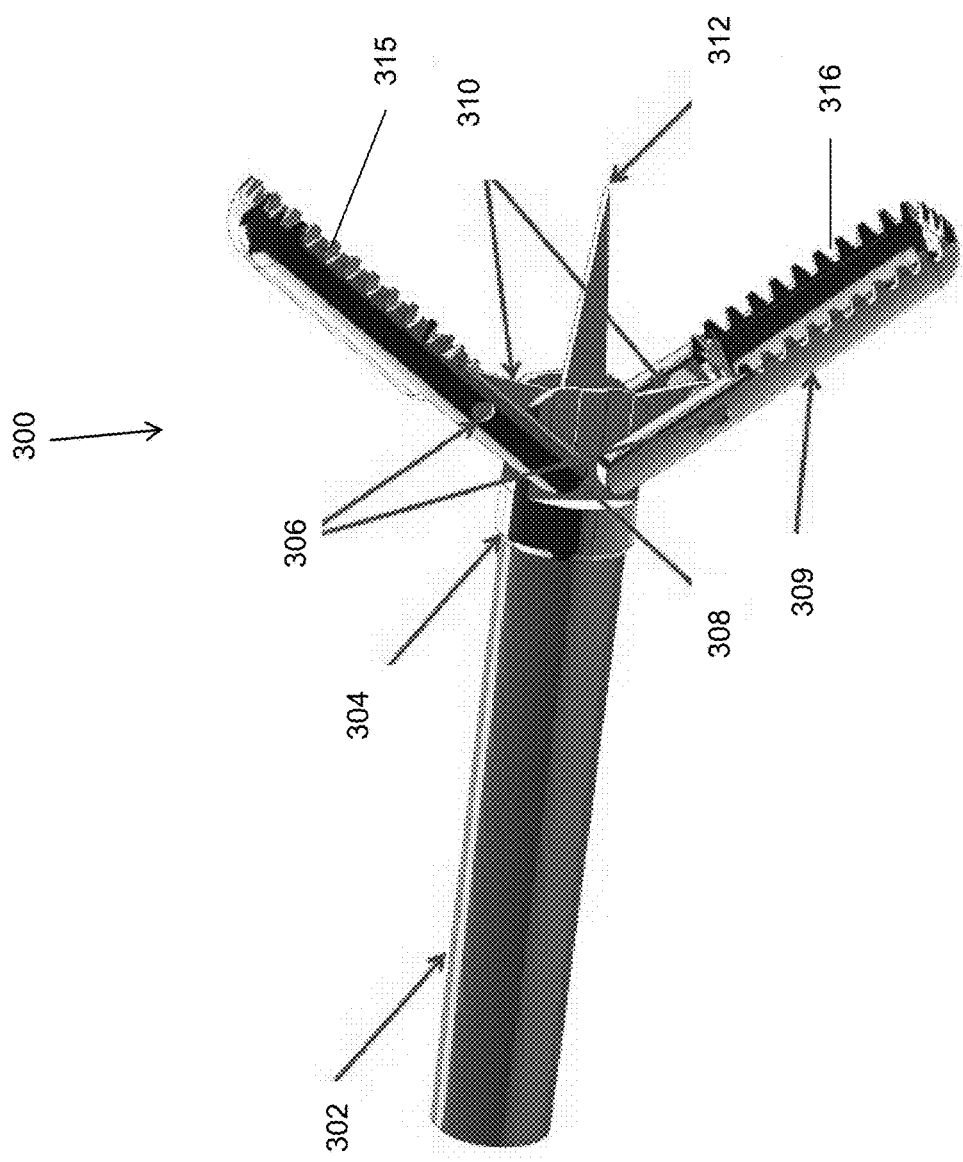
FIG. 3 is an illustration of a forceps portion of a biopsy tool in one embodiment of the present specification.

The biopsy medical tool comprises a medical tool control handle, a catheter that comprises a tube within which at least one control or drive wire is positioned, and the actual working tool portion itself (the biopsy forceps), wherein the handle is connected to the actual working tool portion via the catheter. The biopsy forceps of the present specification has a large "cup" size, longer jaw length, a squared front face, a tapered jaw design, and an offset pivot, which lend to a larger sample size. As shown in FIG. 3, the biopsy forceps working tool 300 includes a catheter 302, a clevis 304, pivots/pins 306, upper jaw 308, lower jaw 309, linkages 310, and a needle 312. In some embodiments, the linkages 310 and pivots 306 enable the movement of the upper and lower jaws 308, 309. When closed, the upper jaw 308 and lower jaw 309 are aligned in an offset position such that a tooth 315 of one jaw portion will fit into a recess 316 formed by two adjacent teeth of the other jaw portion, and vice-versa, namely teeth from the lower jaw will fit into the recesses formed between the teeth of the upper jaw.

Figure 4:
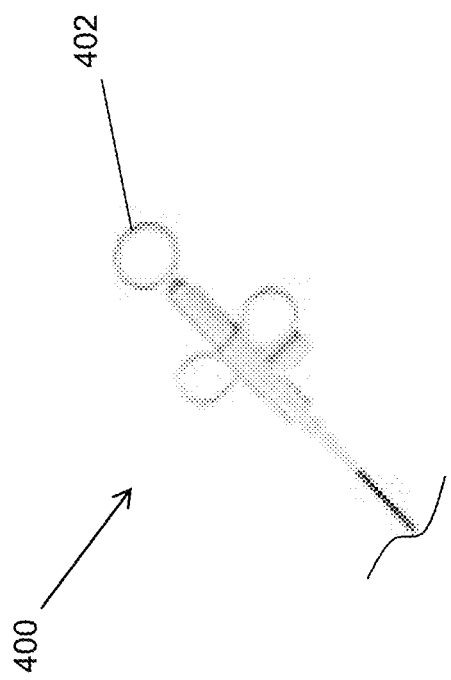
FIG. 4 is an illustration of a control handle of a biopsy tool in one embodiment of the present specification.

As shown in FIG. 4, in one embodiment, the biopsy medical tool 400 includes a control handle 402 that is used to manipulate the forceps device portion. The control handle 402 is pulled back, which effectuates closing the jaws.

Figure 5A:
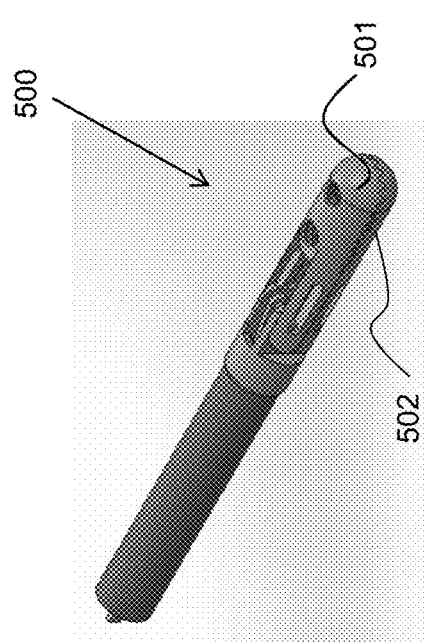
FIG. 5A is an isometric illustration of a forceps portion of a biopsy tool in a closed position, in accordance with one embodiment of the present specification.
Figure 5B:
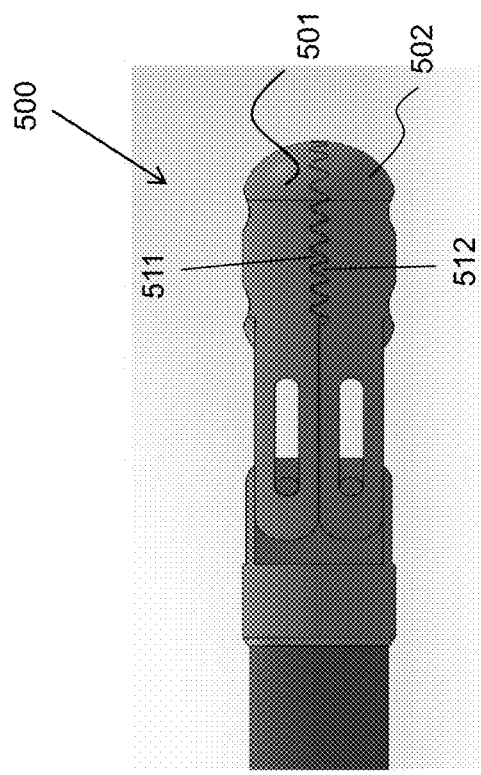
FIG. 5B is a right side view illustration of a forceps portion of a biopsy tool in a closed position, in accordance with one embodiment of the present specification.

FIGS. 5A and 5B show an isometric view and a right side view respectively, of the biopsy forceps 500 of the present specification when the upper jaw 501 and lower jaw 502 are in a closed position. As seen in FIG. 5B, teeth 511 of the upper jaw 501 are depicted aligned within recesses formed between teeth 512 of the lower jaw 502, and vice-versa, to ensure complete closure of the jaws 501, 502.

With the jaws 501, 502 in a closed position, the forceps 500 is then inserted into a working channel of an endoscope (shown as 207 in FIG. 2A). The physician pushes the tool inside the working channel with the help of a catheter (having a length of at least 200 centimeter).

Figure 6A:
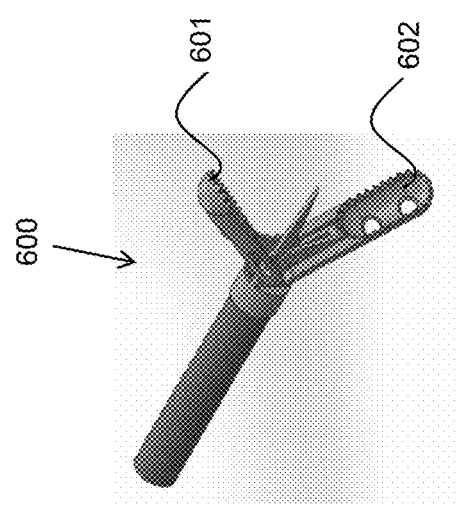
FIG. 6A is an isometric illustration of a forceps portion of a biopsy tool in a first open position, in accordance with one embodiment of the present specification.

Referring back to FIG. 4, handle 402 is advanced forward, which results in a first open configuration or position of the jaws. FIG. 6A shows a first open position of the biopsy forceps 600, depicting the upper jaw 601 positioned away from the lower jaw portion 602.

The physician inserts the medical tool until he sees it in the front camera (or side camera if the scope has a side working channel). When the physician sees the forceps in the camera, he directs it to the polyp/abnormality he wishes to cut. Referring back to FIG. 4, handle 402 is pulled back again, closing the jaws onto the desired tissue. The device is then removed from the scope.

Figure 6B:
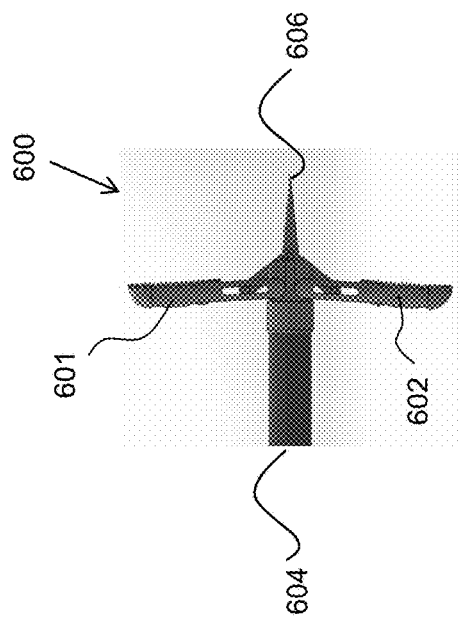
FIG. 6B is a right side view illustration of a forceps portion of a biopsy tool in a second open position, in accordance with one embodiment of the present specification.

As shown in FIG. 6B, once extracted from the scope, the biopsy medical tool 600 is opened into a second open configuration, allowing for facile extraction of the sample from the tool. Sample removal is facilitated by a control or drive wire that is located within the catheter portion 604. As the drive wire is refracted, so is the needle portion 606, releasing the tissue sample. In the second open configuration, the upper jaw 601 is positioned further from the lower jaw 602 compared to the first open configuration depicted in FIG. 6A, providing more space for a user to manipulate and remove a tissue sample.

FIG. 7 is a diagram showing a comparison of biopsy forceps with respect to sample size. The biopsy forceps of the present specification have a large "cup" size, longer jaw length, a squared front face, a tapered jaw design, and an offset pivot, which lend to a larger sample size. FIG. 7 illustrates a bite range of a first embodiment of forceps 702 having an offset pivot point and a second embodiment of forceps 701 having a single pivot point compared to bite ranges of prior art forceps 703, 704 each having a single pivot point. The forceps of the present specification also include longer jaw length, allowing for a shallower and wider cut during operation. For example, in some embodiments, the length of the jaws of forceps 702, 701 are in a range of 8 mm to 9 mm and are preferably equal to 8.25 mm and 8.50 mm respectively. Assuming a minimum cut depth in a range of 2 mm to 3 mm, and more preferably 2.20 mm, in some embodiments, the forceps 702, 701 of the present specification provide a wider maximum cut width in a range of 10 mm to 13 mm, preferably 11 mm to 13 mm, and more preferably in approximately 11.4 mm to 12.50 mm. Moreover, in some embodiments, the presently disclosed forceps jaws 702, 701 have an angle of opening in a range of 80-100 degrees, preferably 80-90 degrees. Therefore, the forceps 702, 701 of the present specification are capable of wider cuts without having to open to as wide an angle as those encountered in the prior art.

The biopsy forceps of the present specification is constructed using rigid materials. In some embodiments, the materials include stainless steel and/or rigid polymers, such as PEEK. The primary method of manufacture includes metal injection molding and/or traditional polymer injection molding as well as stamping. There are also a reduced number of components, thus making this device easier to manufacture and assemble compared to prior art devices. The device includes a plurality of pins that are press-fit, which require grinding after assembly, however, enabling an easier assembly of the tool.

Figure 8A:
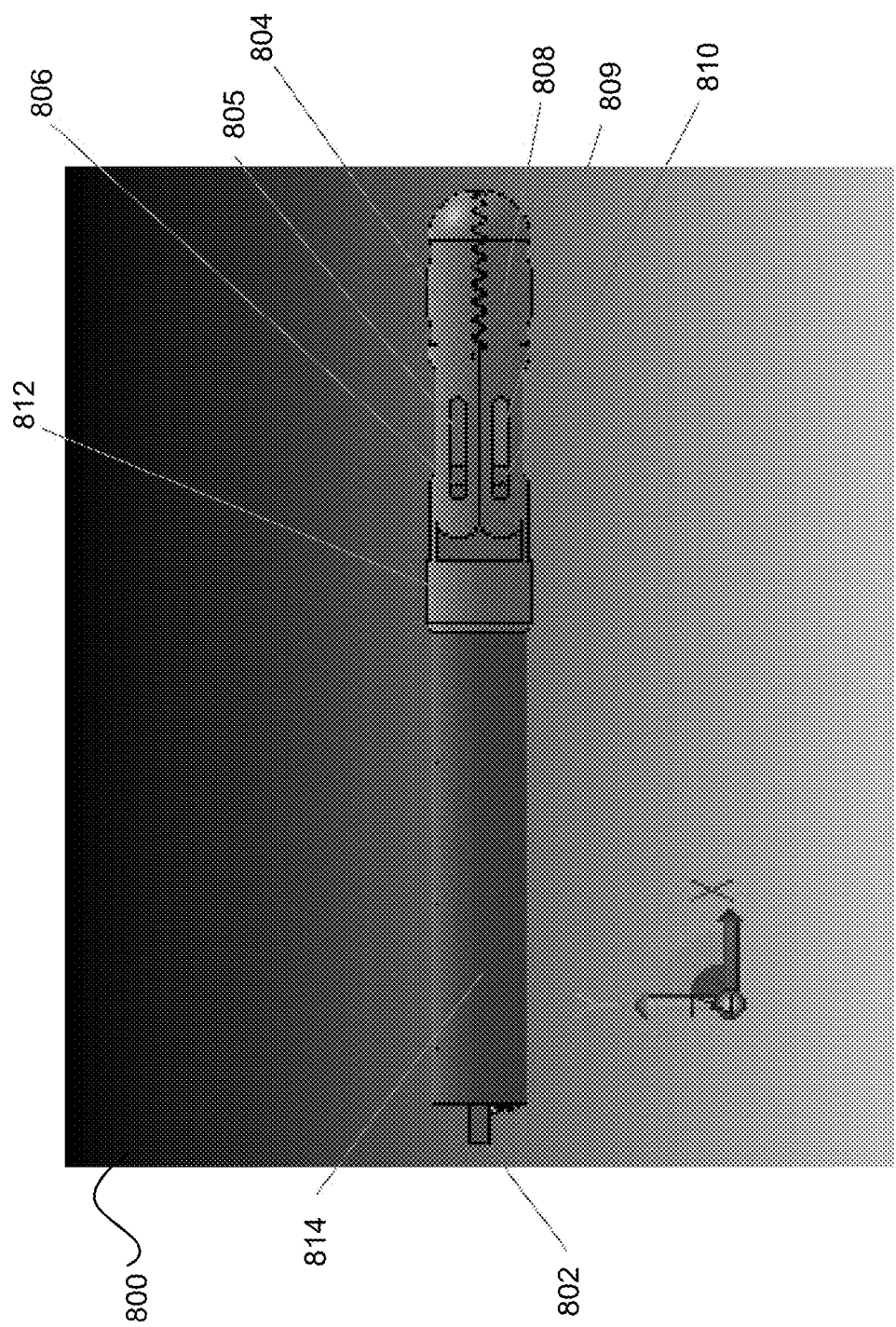
FIG. 8A illustrates a right side view of a biopsy forceps in a closed position, in accordance with an embodiment of the present specification.

FIG. 8A illustrates a right side view of a biopsy forceps 800 in a closed position, in accordance with an embodiment of the present specification. Forceps 800 comprises a needle drive wire 802, a first jaw 804 coupled with a first pin 806, a second jaw 808 coupled with a second pin 810, a coupling unit or clevis 812 and a spring wire jacket 814. Jaw 804 comprises a distal portion having a plurality of teeth, and a proximal portion having a longitudinal slot 805. In one embodiment, jaw 804 includes only one slot 805 on one side of said jaw 804. In another embodiment, jaw 804 includes a slot 805 on each side. Pin 806 is positioned at one end of slot 805 as shown. Jaw 808 comprises a distal portion having a plurality of teeth, and a proximal portion having a longitudinal slot 809. In one embodiment, jaw 808 includes only one slot 808 on one side of said jaw 808. In another embodiment, jaw 808 includes a slot 809 on each side. Pin 810 is positioned at one end of slot 809 as shown. In an embodiment, the clevis is a u-shaped component having a proximal base and two distal protrusions, one of which connects to a left proximal end of an upper jaw 804 at a first pivot point and to a left proximal end of a lower jaw 808 at a second pivot point. The second distal protrusion connects to a right proximal end portion of said upper jaw 804 at a third pivot point and to a right proximal end of said lower jaw 808 at a fourth pivot point.

Figure 8B:
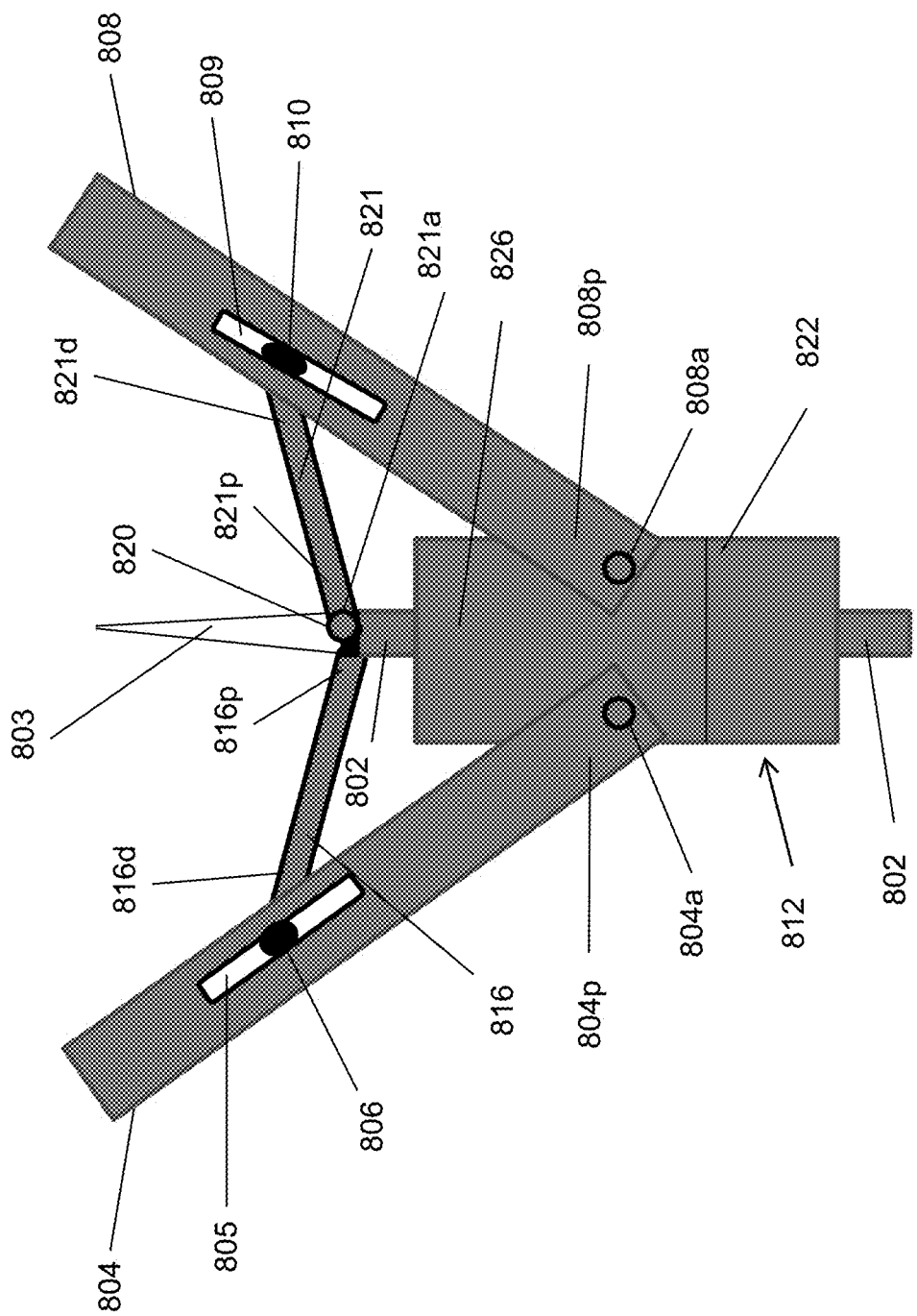
FIG. 8B illustrates a right side exemplary block diagram of the clevis of the biopsy forceps, in accordance with an embodiment of the present specification.

The needle drive wire 802 extends within the spring wire jacket 814 and connects to a device handle at its proximal end and to a junction point, which couples the needle drive wire with a pair of linkages, at its distal end. The needle drive wire 802 transfers actuation force from the device handle to a needle positioned between the jaws 804 and 808 and to a pair of linkages used to move the jaws 804, 808. The spring wire jacket 814 comprises an elongate flexible tube or catheter and contains a spring within, protecting the spring from damage. FIG. 8B illustrates a right side block diagram of an exemplary embodiment of the clevis portion 812. Clevis 812 is a stationary fixed base that holds the pivot points of jaws 804, 808. The clevis 812 comprises a base portion 822 and a left distal protrusion (not shown) and a right distal protrusion 826. A proximal left end (not shown) of the first jaw 804 is attached to said left distal protrusion (not shown) at a first jaw pivot point 804a and a proximal left end of the second jaw 808 is attached to said left distal protrusion (not shown) at a second jaw pivot point 808a. A proximal right end 804p of the first jaw 804 is attached to said right distal protrusion 826 at said first jaw pivot point 804a and a proximal right end 808p of the second jaw 808 is attached to said right distal protrusion 826 at said second jaw pivot point 808a.

The distal end of the needle drive wire 802 includes a first linkage pivot point (not shown) and a second linkage pivot point 821a. The first linkage pivot point (not shown) is positioned to the left of the needle drive wire 802 and allows for pivoting of the first linkage 816 relative to the needle drive wire 802. The second linkage pivot point 821 is positioned to the right of the needle drive wire 802 and allows for pivoting of the second linkage 821 relative to the needle drive wire 802. The pivot point (not shown) of linkage 816 and the pivot point 821a of linkage 821 are offset, both longitudinally (being located further distally on the device) and laterally, from the pivot points 804a, 808a of jaws 804, 808. Proximal ends 816p and 821p of the linkages 816 and 821 respectively, are connected at a junction point 820 to the needle drive wire 802 such that the proximal ends 816p and 821p of the linkages 816, 821 move proximally and distally with the needle drive wire 802 and pivot about said needle drive wire 802 as the needle drive wire 802 is moved longitudinally with respect to the clevis 812. The distal ends 816d and 821d of the linkages 816, 821 are coupled with pins 806 and 810 respectively. The pins 806, 810 are positioned within slots 805, 809 of the first jaw 804 and second jaw 808 respectively. When the needle drive wire 802 is pushed distally using the device handle, the linkages 816, 821 move distally and rotate about their pivot points on the needle drive wire 802, causing the pins 805, 810 to slide distally within the slots 805, 809 which results in the jaws 804, 808 pivoting about their pivot points on the clevis protrusion 826 and opening. When the needle drive wire 802 is pulled proximally using the device handle, the linkages 816, 821 move proximally and rotate about their pivot points on the needle drive wire 802, causing the pins 806, 810 to slide proximally within the slots 805, 809 which results in the jaws 804, 808 rotating about their pivot points on the clevis protrusion 826 and closing. This cam mechanism causes the jaws 804, 808 to open and close. Attached to the needle drive wire 802 distal to said junction point 820 is a needle 803 used for piercing tissues. The needle 803 also moves proximally and distally with longitudinal movement of the needle drive wire 802. Therefore, in one embodiment, as the device handle is pushed distally to open the jaws 804, 808, the needle 803 is extended distally. As the device handle is pulled proximally to close the jaws 804, 808, the needle 803 is retracted.

As described above, the clevis 812, which is a coupling unit, has two different pivoting points, one each for connecting with first jaw 804 and second jaw 808. Referring again to FIG. 8B, pivot points 804a and 808a on distal protrusion 826 of clevis 812 are the same distance longitudinally from an end of the clevis 812, but are offset laterally. The right side of jaw 804 is connected to pivoting point 804a while the right side of jaw 808 is connected to pivoting point 808a.

Figure 8D:
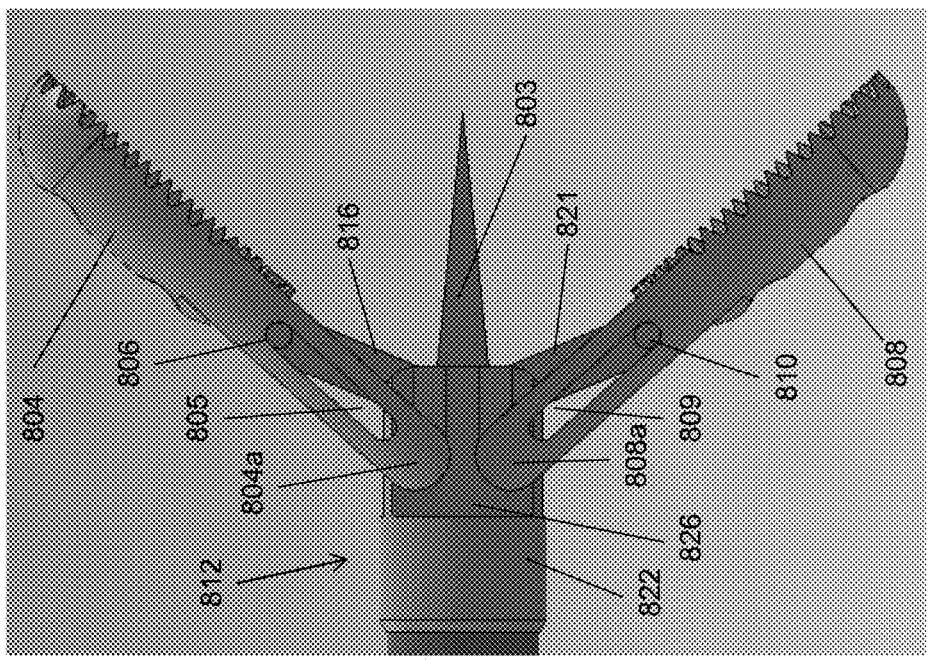
FIG. 8D is a right side view illustration of the clevis and jaws of one embodiment of the biopsy forceps device of the present specification.
Figure 8C:
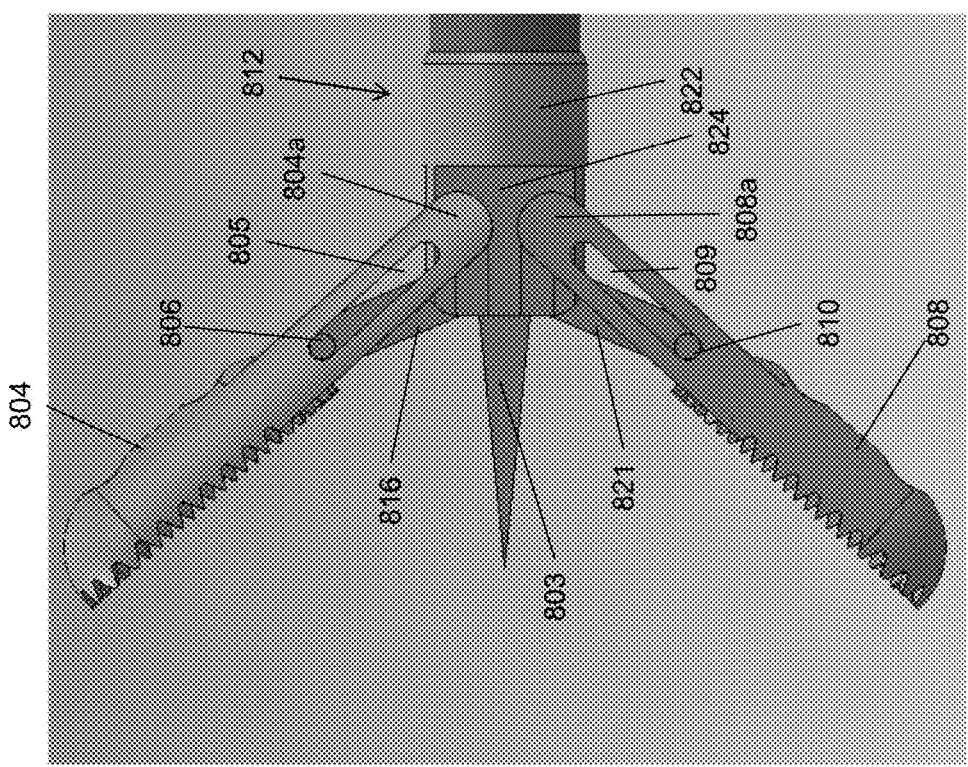
FIG. 8C is a left side view illustration of the clevis and jaws of one embodiment of the biopsy forceps device of the present specification.
Figure 8F:
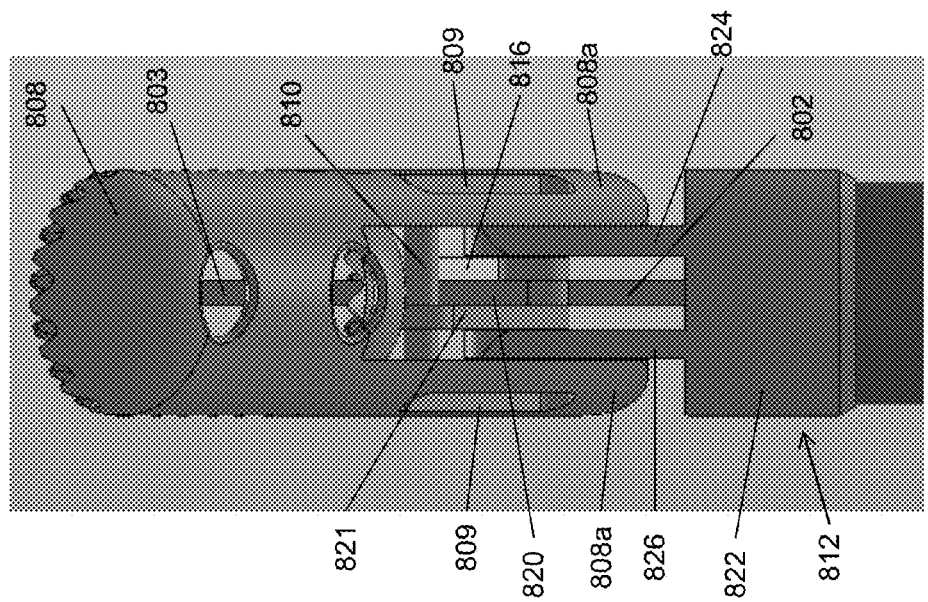
FIG. 8F is a bottom-up view illustration of the clevis and jaws of one embodiment of the biopsy forceps device of the present specification.
Figure 8E:
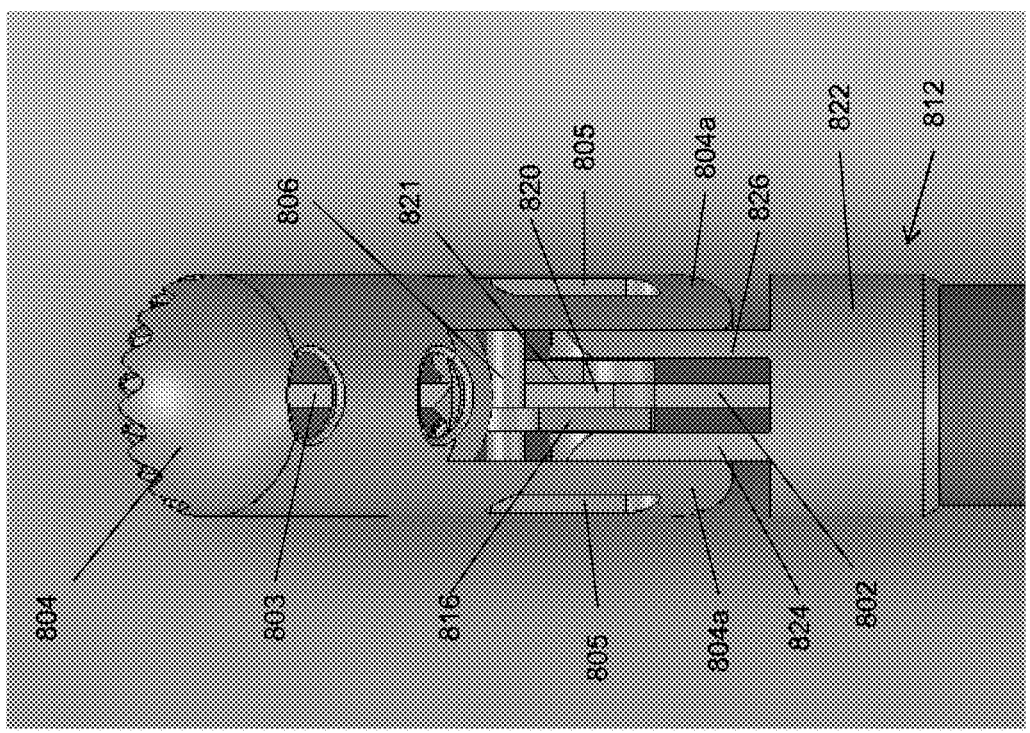
FIG. 8E is a top-down view illustration of the clevis and jaws of one embodiment of the biopsy forceps device of the present specification.

FIGS. 8C and 8D are left and right side view illustrations respectively, of the clevis 812 and jaws 804, 808 of one embodiment of the biopsy forceps device of the present specification. FIGS. 8E and 8F are top-down and bottom-up view illustrations respectively, of the clevis 812 and jaws 804, 808 of one embodiment of the biopsy forceps device of the present specification. Referring to FIGS. 8C through 8F simultaneously, the clevis 812 includes a base portion 822, a left protrusion 824, and a right protrusion 826. The left proximal end of the first jaw 804 is attached to the left protrusion 824 at a first jaw pivot point 804a and the left proximal end of the second jaw 808 is attached to the left protrusion 824 at a second jaw pivot point 808a. The right proximal end of the first jaw 804 is attached to the right protrusion 826 at said first jaw pivot point 804a and the right proximal end portion of the second jaw 808 is attached to the right protrusion 826 at said second jaw pivot point 808a. First jaw pivot point 804a and second jaw pivot point 808a are offset laterally with respect to one another but are at the same longitudinal position on the biopsy forceps device.

The first jaw 804 includes a slot 805 on its left side and right side. A first pin 806 is positioned with its ends within these slots 805. A first linkage 816, having a proximal end and a distal end, is attached with its distal end to the first pin 806. The proximal end of the first linkage 816 is attached to a junction point 820 on a needle drive wire 802. The second jaw 808 includes a slot 809 on its left side and right side. A second pin 810 is positioned with its ends within these slots 809. A second linkage 821, having a proximal end and a distal end, is attached with its distal end to the second pin 810. The proximal end of the second linkage 821 is attached to a junction point 820 on a needle drive wire 802. Opening and closing of the jaws 804, 808 is effectuated by longitudinal movement of the needle drive wire 802 which is translated to movement and pivoting of the linkages 816, 821 and movement of the pins 806, 810 within the slots 805, 809 causing pivoting of the proximal ends of the jaws 804, 808 about their pivot points 804a, 808a as described above. The junction point 820, where the first linkage 816, second linkage 821, and needle drive wire 802 are coupled together, is positioned between the left protrusion 824 and right protrusion 826 of the clevis 812. A needle 803 is attached to, and extends distally from, the junction point 820.

In an embodiment, the length of each of jaws 804, 808 is approximately 8 mm. The jaws 804, 808 have rounded distal ends, thereby eliminating sharp edges that may interfere with the device function when inserted within a body lumen, while still maintaining a closed geometry that enables the device's function as forceps. The present device design comprises fewer number of device parts as compared to prior art designs, thereby making the manufacture of the present device easier.

Figure 8G:
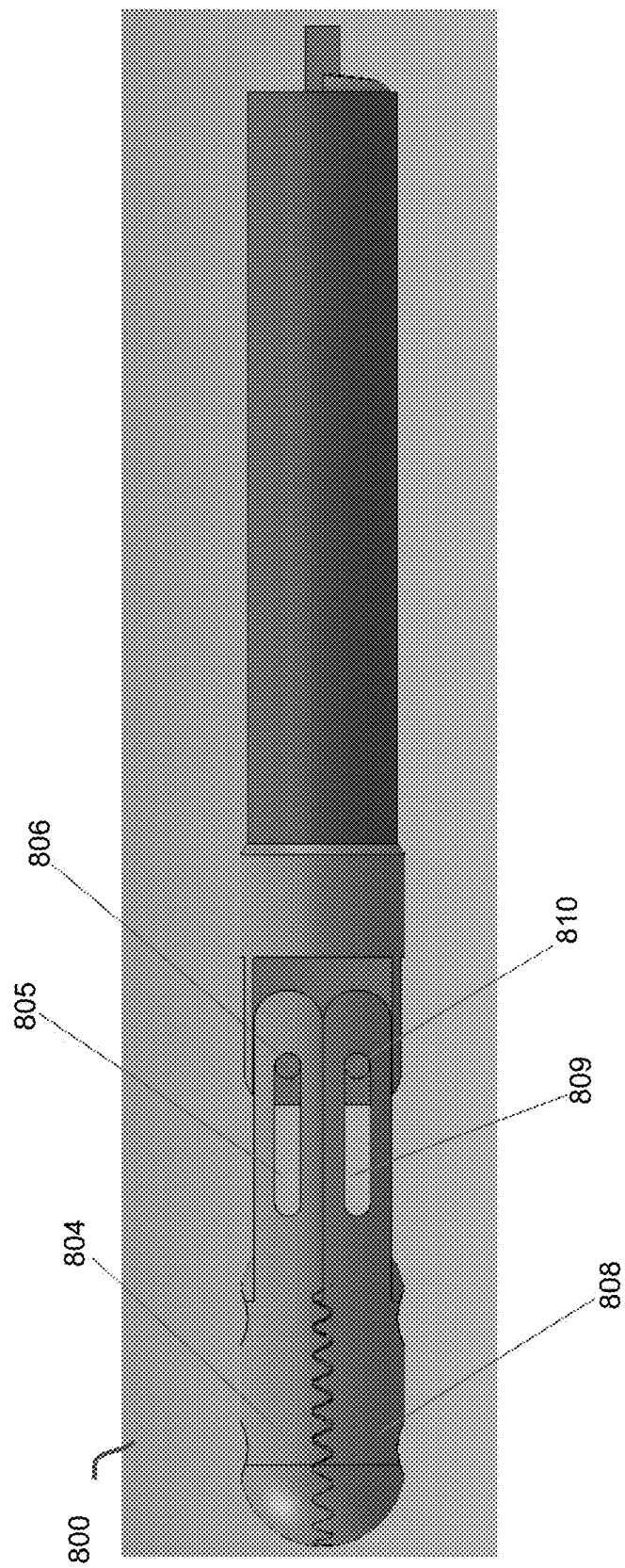
FIG. 8G illustrates a left side view of a biopsy forceps in a closed position, in accordance with an embodiment of the present specification.

FIG. 8G illustrates a left side view of a biopsy forceps 800 in a closed position, in accordance with an embodiment of the present specification. Pins 806 and 810 are positioned at distal ends of slots 805 and 809 respectively and enable the open and close movement of the jaws 804 and 808.

Figure 8H:
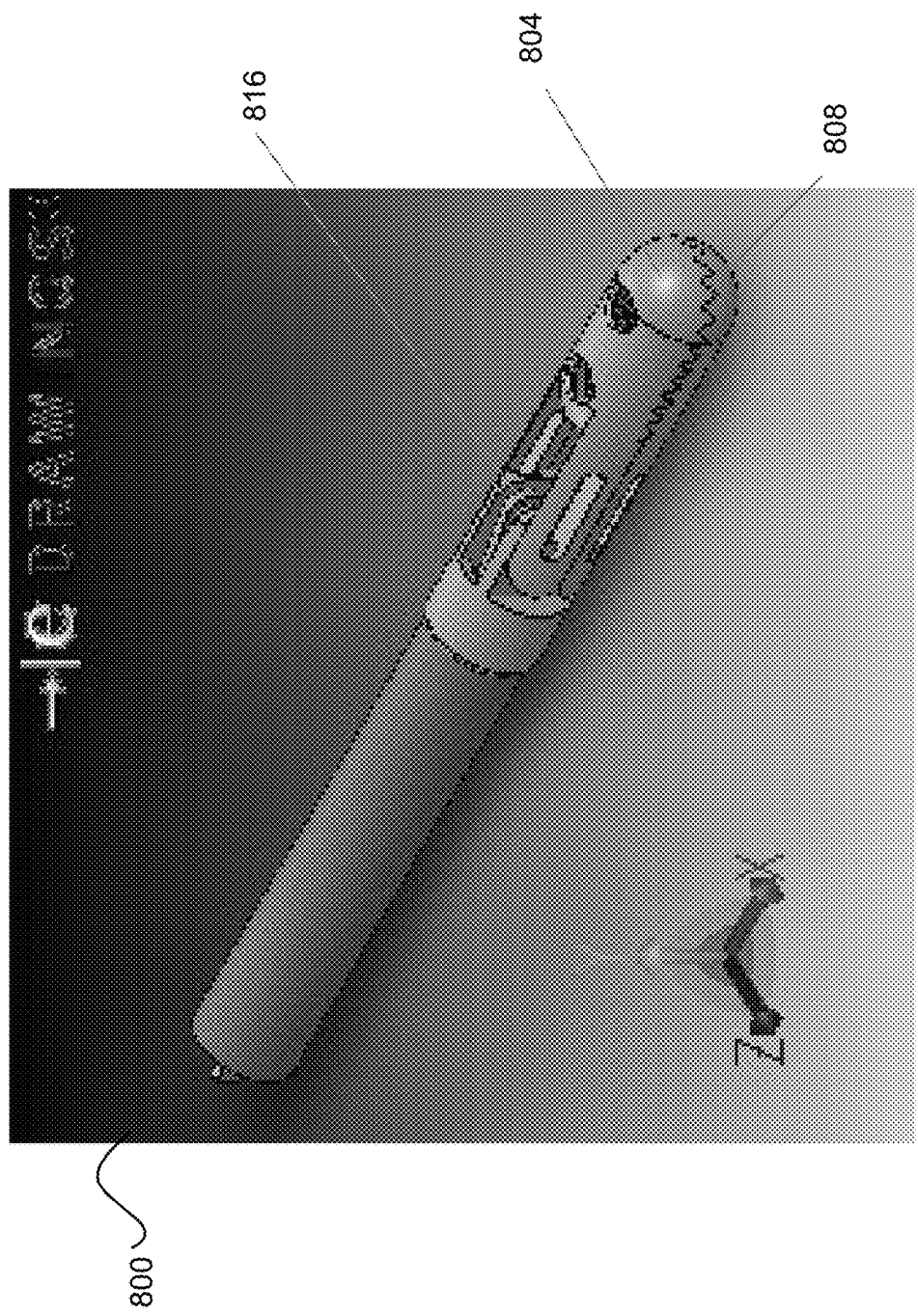
FIG. 8H illustrates an isometric view of a biopsy forceps in a closed position, in accordance with an embodiment of the present specification.

FIG. 8H illustrates an isometric view of a biopsy forceps 800 in a closed position, in accordance with an embodiment of the present specification. A first linkage 816 that enables jaws 804 and 808 to open and close can be seen in FIG. 8H.

Figure 8I:
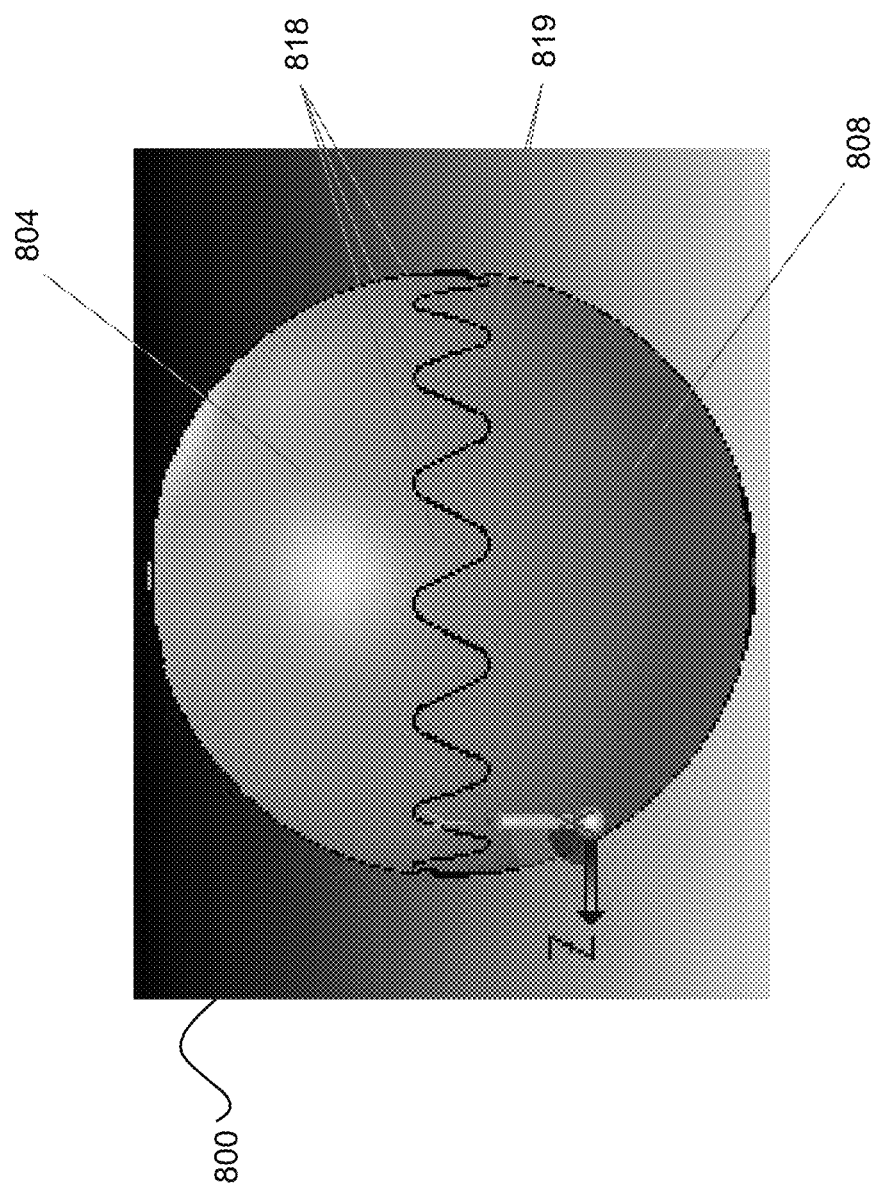
FIG. 8I illustrates a front view of a biopsy forceps in a closed position, in accordance with an embodiment of the present specification.

FIG. 8I illustrates a front view of a biopsy forceps 800 in a closed position, in accordance with an embodiment of the present specification. As seen in FIG. 8I, the teeth 818 of jaw 804 interlock with teeth 819 of jaw 808 in a closed position, such that there are no gaps between the interlocking teeth 818 and 819.

Figure 8J:
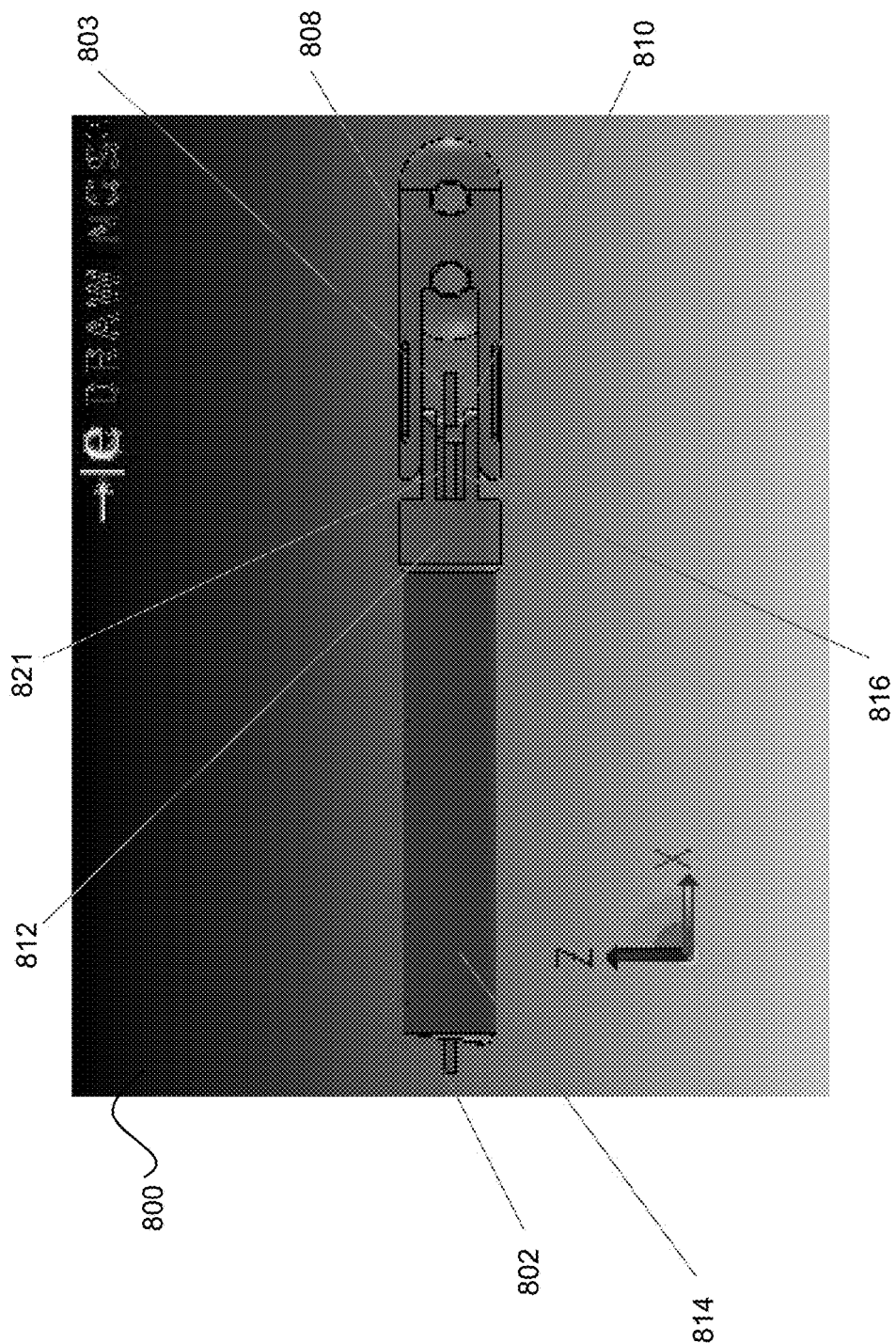
FIG. 8J illustrates a bottom-up view of a biopsy forceps in a closed position, in accordance with an embodiment of the present specification.

FIG. 8J illustrates a bottom-up view of a biopsy forceps 800 in a closed position, in accordance with an embodiment of the present specification. Jaw 808 can be seen coupled with the second pin 810. A linkage 821 and pin 810 along with linkage 816 enable jaws 804 and 808 to open and close. Needle drive wire 802 passes through spring wire with jacket 814 and emerges as a needle 803 through clevis 812 between the first jaw and the second jaw 808.

Figure 8K:
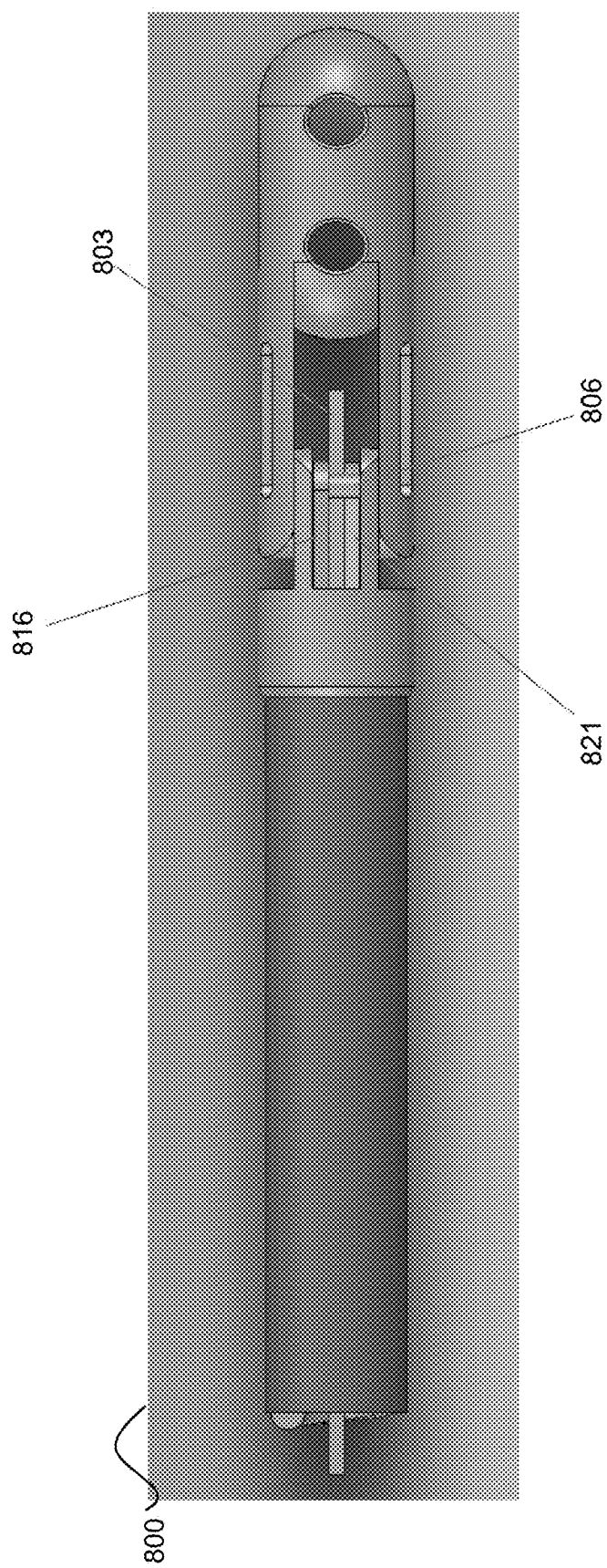
FIG. 8K illustrates a top-down view of a biopsy forceps in a closed position, in accordance with an embodiment of the present specification.

FIG. 8K illustrates a top-down view of a biopsy forceps 800 in a closed position, in accordance with an embodiment of the present specification. Linkage 816 and pin 806 along with linkage 821 can be seen surrounding the needle 803 in FIG. 8F.

Figure 8L:
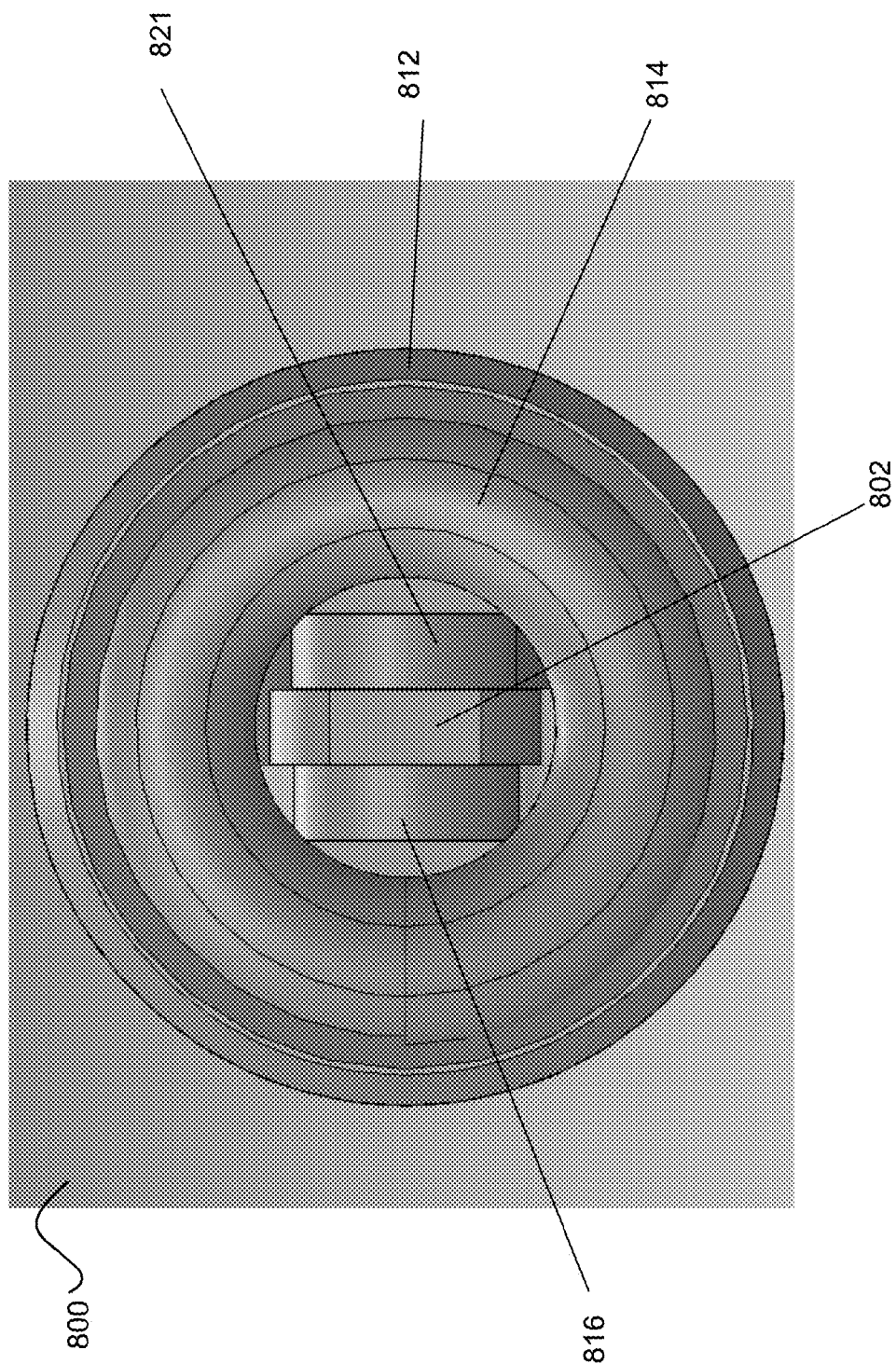
FIG. 8L illustrates a cross sectional rear view of the embodiment of the biopsy forceps of FIG. 8A in a closed position.

FIG. 8L illustrates a cross sectional rear view of the embodiment of the biopsy forceps 800 of FIG. 8A in a closed position. The position of the cross section depicted in FIG. 8L is at the junction point 820 of FIGS. 8E and 8F. Referring to FIGS. 8A through 8L, needle drive wire 802 passes through spring wire jacket 814 and emerges through clevis 812 as a needle 803 on an opposite side of forceps 800 between jaws 804 and 808. Linkages 816 and 821 are positioned on either side of needle 803 for supporting movement of the jaws 804 and 808. The spring wire jacket 814 is depicted surrounding the proximal portions of the linkages 816, 821 and needle drive wire 802.

Figure 8M:
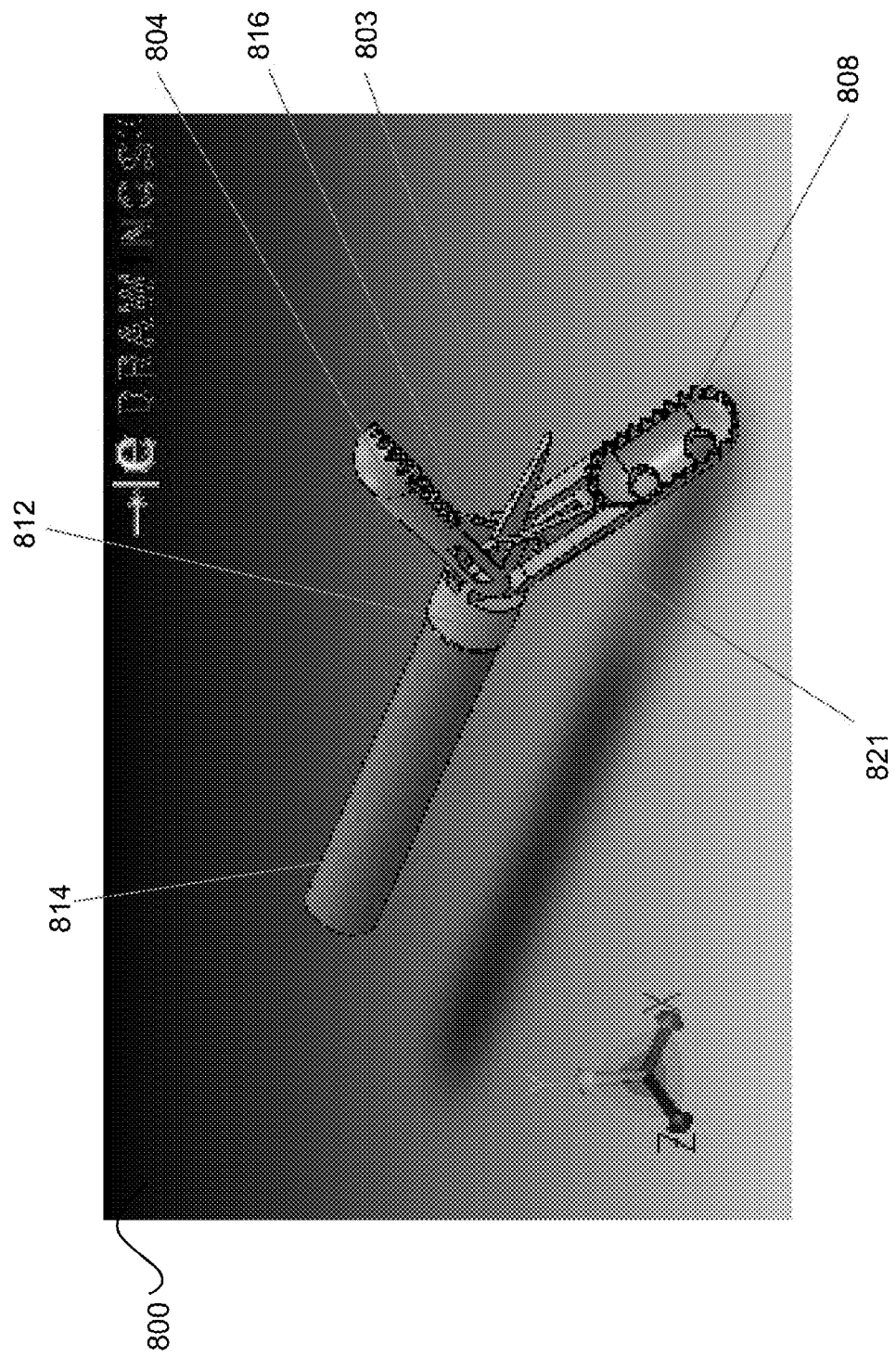
FIG. 8M illustrates a biopsy forceps in an open position, in accordance with an embodiment of the present specification.

FIG. 8M illustrates a biopsy forceps 800 in an open position, in accordance with an embodiment of the present specification. Forceps 800 are shown with jaws 804 and 808 in an open position with linkages 816 and 821 supporting the jaws 804, 808. The needle drive wire passes through spring wire with jacket 814 and is visible emerging through clevis 812 as needle 803, between the linkages 816 and 821.

Figure 8N:
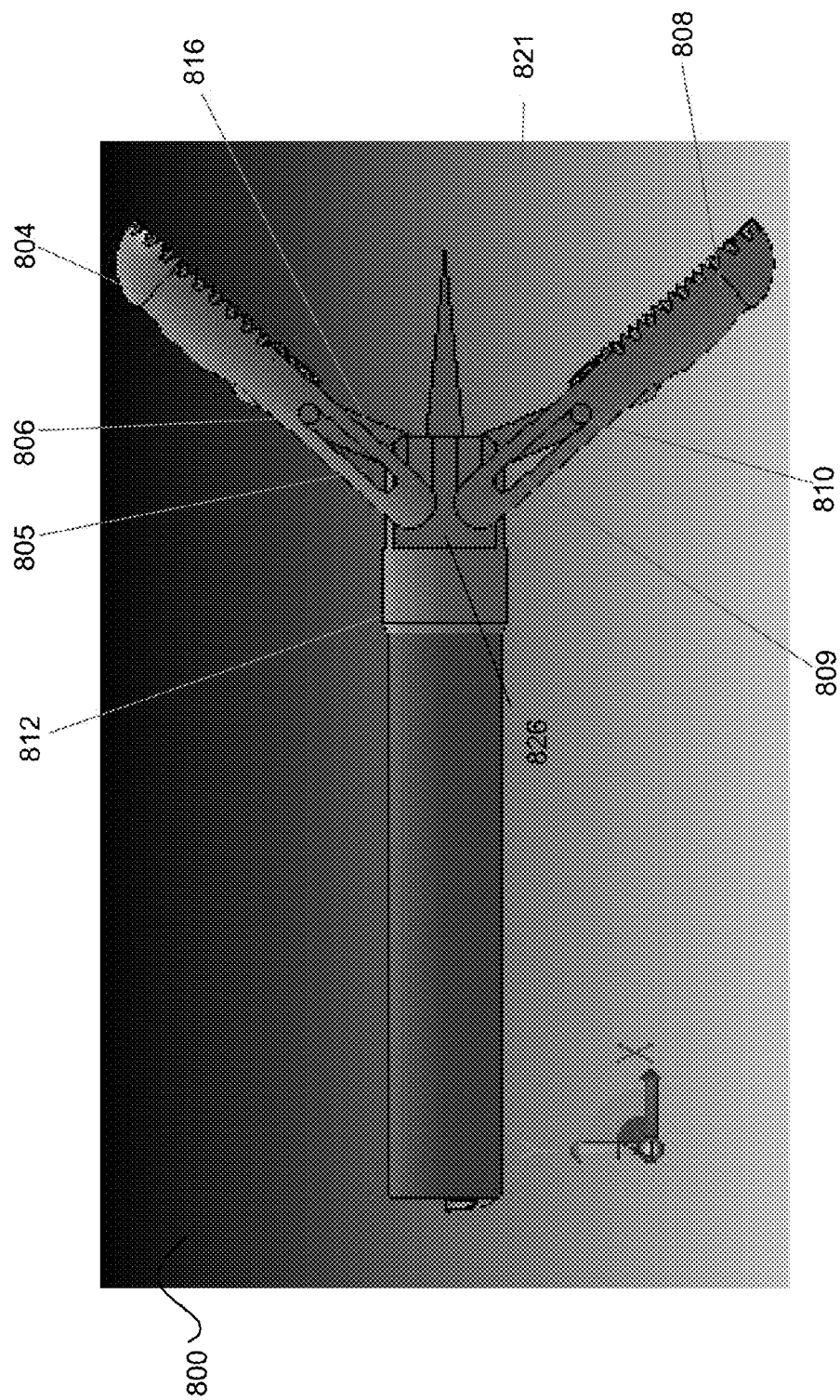
FIG. 8N illustrates a right side view of a biopsy forceps in an open position, in accordance with an embodiment of the present specification.

FIG. 8N illustrates a right side view of a biopsy forceps 800 in an open position, in accordance with an embodiment of the present specification. Linkage 816 emerges from behind the right protrusion 826 of clevis 812, where it is connected to the needle drive wire, and is connected by means of pin 806 to slot 805 of jaw 804. Similarly, linkage 821 emerges from behind the right protrusion 826 of clevis 812, where it is also connected to the needle drive wire, and is connected by means of pin 810 to slot 809 of jaw 808.

Figure 8O:
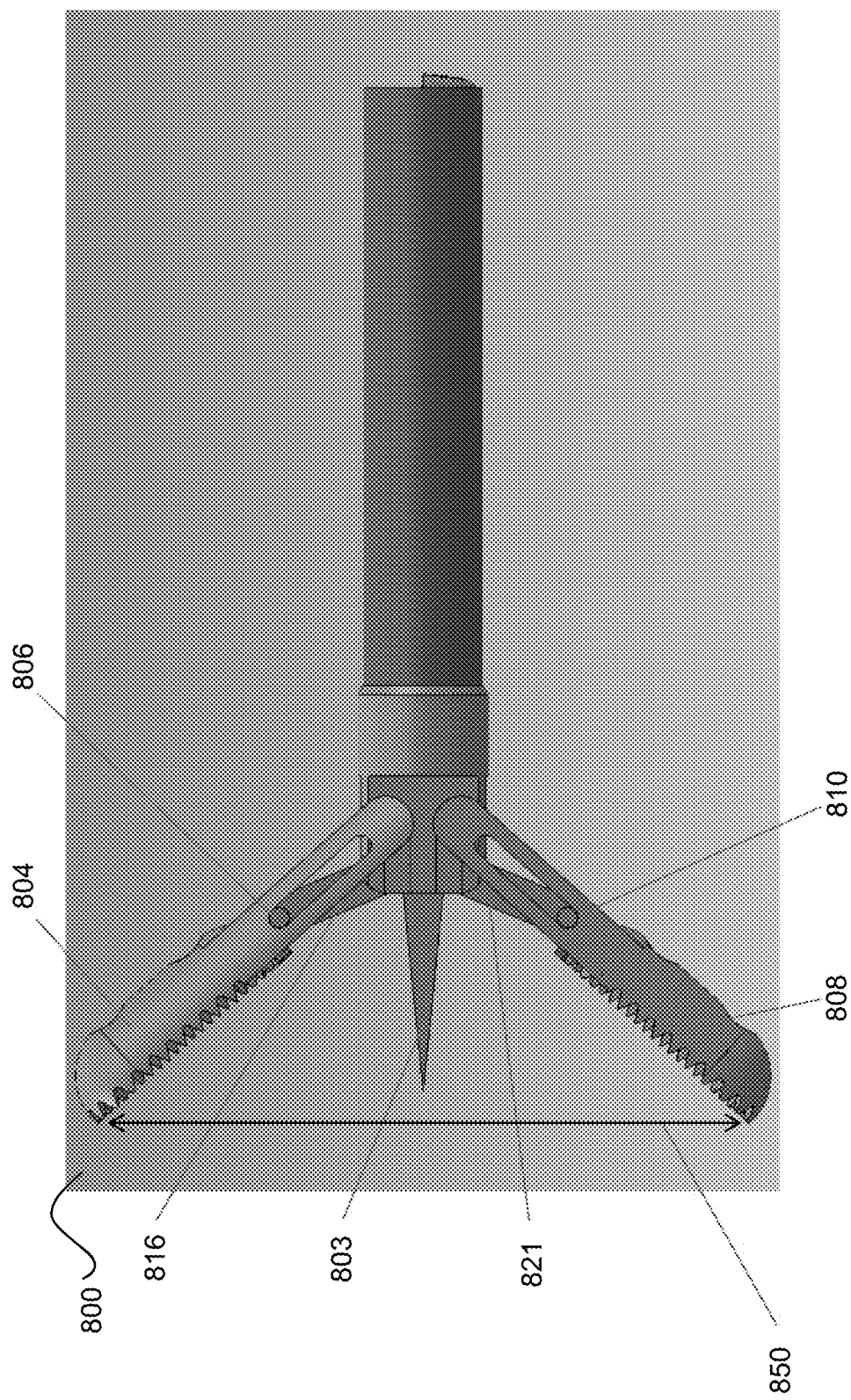
FIG. 8O illustrates a left side view of a biopsy forceps in an open position, in accordance with an embodiment of the present specification.

FIG. 8O illustrates a left side view of a biopsy forceps 800 in an open position, in accordance with an embodiment of the present specification. Linkage 816 coupled with pin 806 enables open and close movements of jaw 804. Linkage 821 coupled with pin 810 enables open and close movements of jaw 808. In the open position of jaws 804 and 808 as shown in FIG. 8O, needle 803 is exposed. In one embodiment, distance 850 marked on FIG. 8J denotes a maximum opening distance of forceps 800.

Figure 8P:
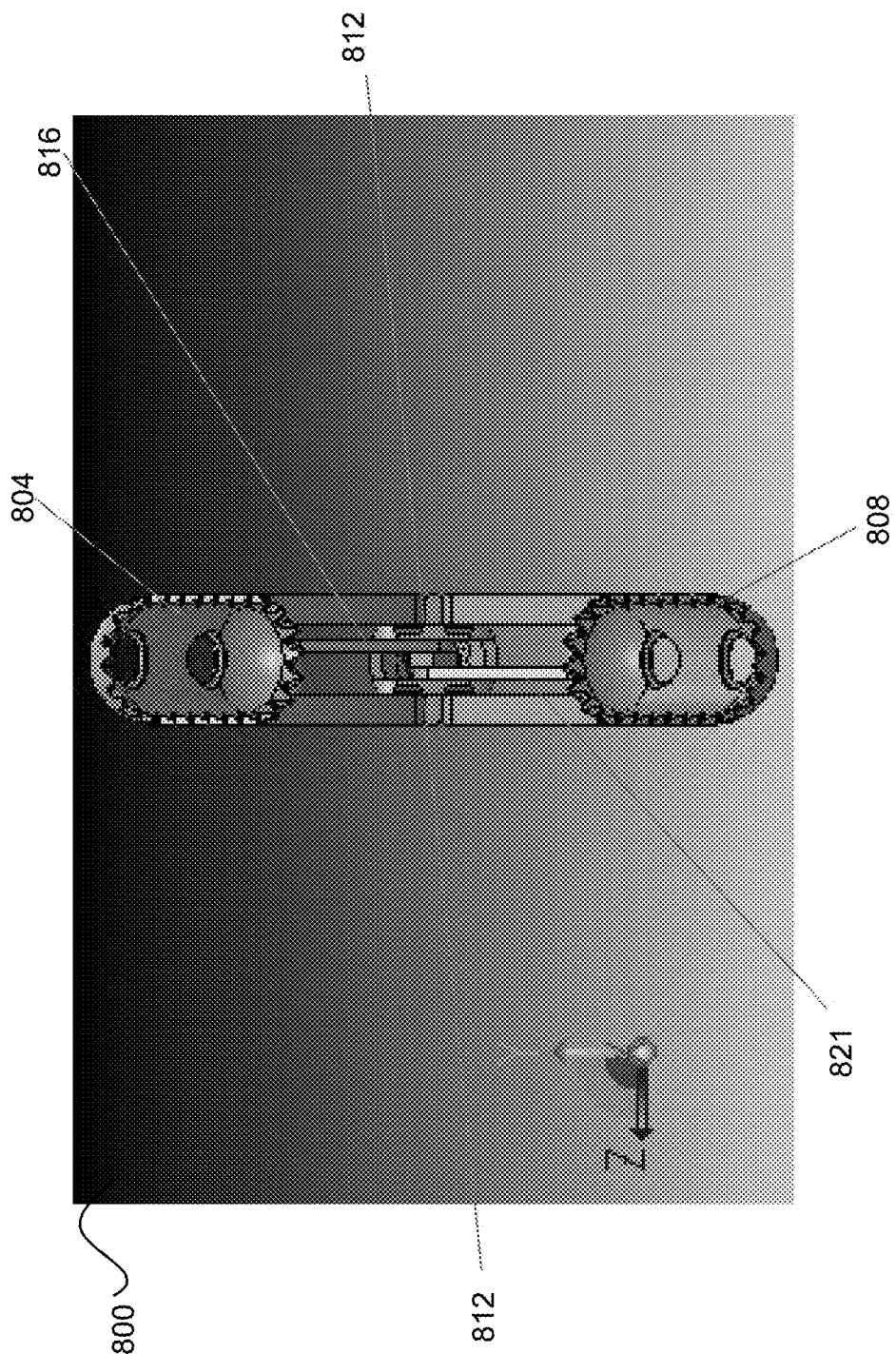
FIG. 8P illustrates a front view of a biopsy forceps in an open position, in accordance with an embodiment of the present specification.

FIG. 8P illustrates a front view of a biopsy forceps 800 in an open position, in accordance with an embodiment of the present specification. As can be seen in FIG. 8P, a distal end of linkage 816 extends toward jaw 804 where it is connected to the jaw by a first pin while a proximal end extends toward clevis 812. Similarly, a distal end of linkage 821 extends toward jaw 808 where it is connected to the jaw by a second pin while a proximal end extends toward clevis 812. The proximal ends of the linkages 816, 821 connect with the needle drive wire at a junction point positioned between the left and right protrusions of the clevis 812.

Figure 8Q:
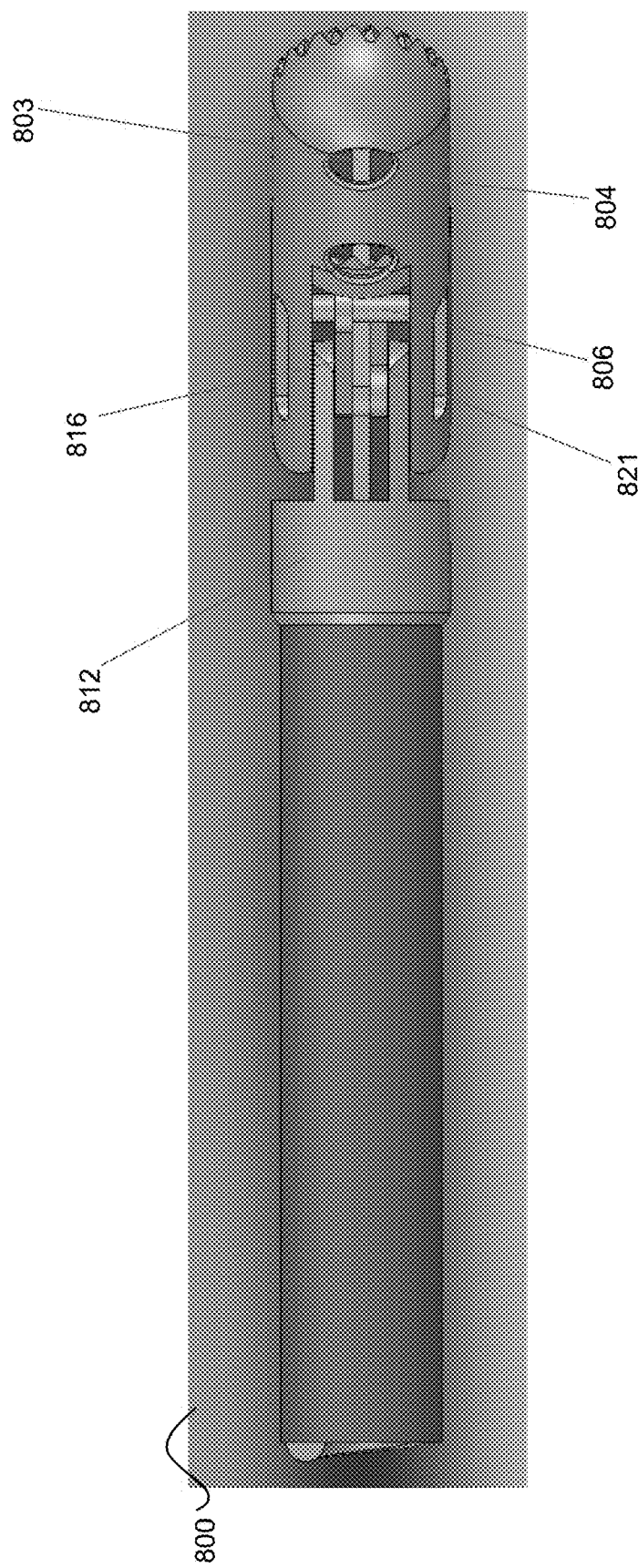
FIG. 8Q illustrates a top-down view of a biopsy forceps in an open position, in accordance with an embodiment of the present specification.

FIG. 8Q illustrates a top-down view of a biopsy forceps 800 in an open position, in accordance with an embodiment of the present specification. Linkage 816 coupled with pin 806 for enabling open and close movement of jaw 804 can be seen in FIG. 8Q. A portion of linkage 821 is also visible in this view. Needle 803 emerges from clevis 812 between first jaw 804 and the second jaw (not visible in this view).

Figure 8R:
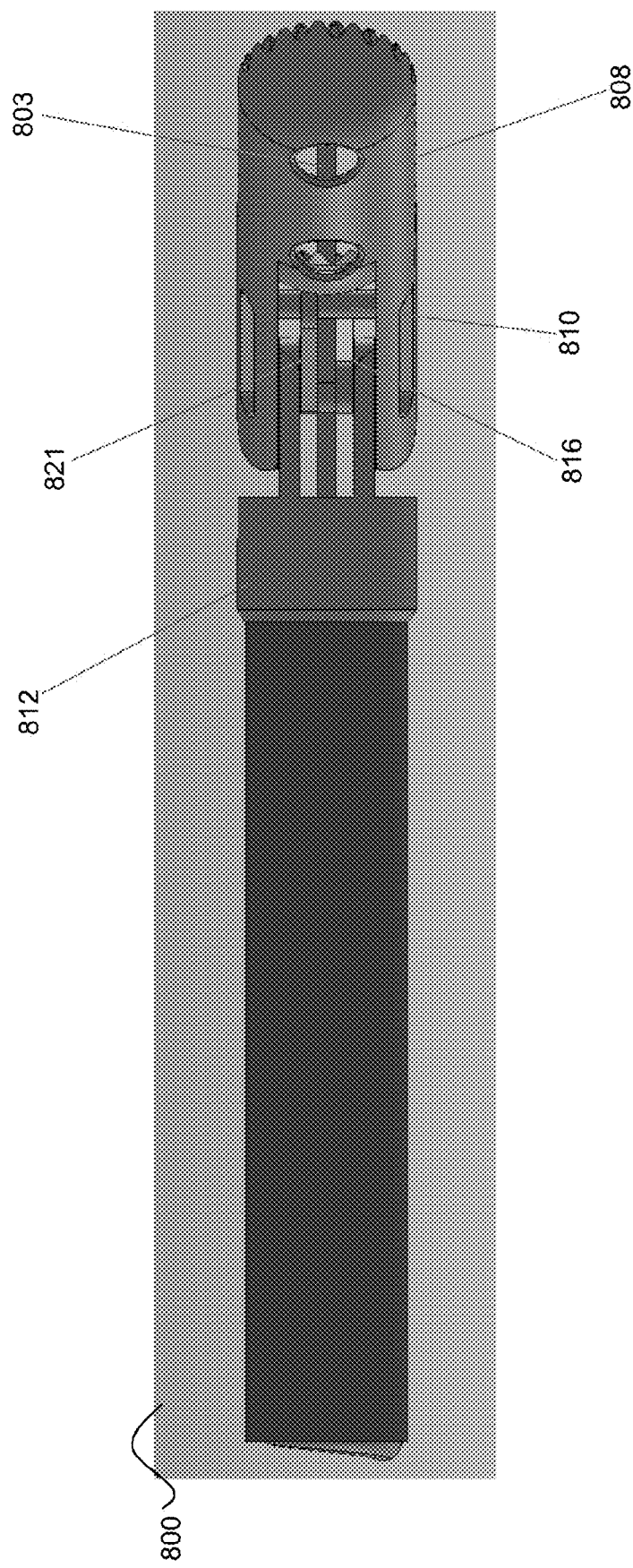
FIG. 8R illustrates a bottom-up view of a biopsy forceps in an open position, in accordance with an embodiment of the present specification.

FIG. 8R illustrates a bottom-up view of a biopsy forceps 800 in an open position, in accordance with an embodiment of the present specification. Linkage 821 coupled with pin 810 for enabling open and close movement of jaw 808 can be seen in FIG. 8R. A portion of linkage 816 is also visible in this view. Needle 803 emerges from clevis 812 between second jaw 808 and the first jaw (not visible in this view).

Figure 8S:
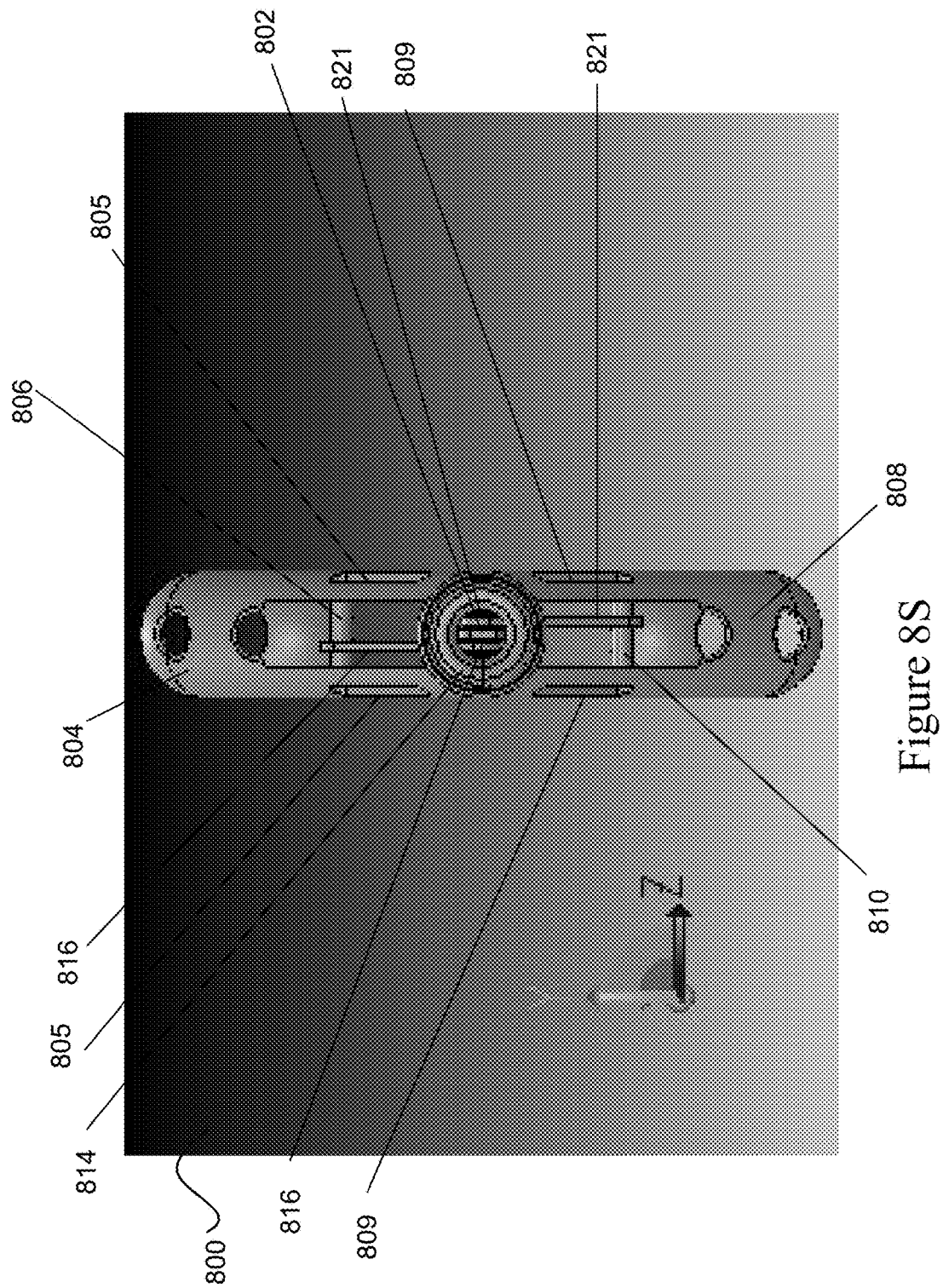
FIG. 8S illustrates a cross sectional rear view of a biopsy forceps in an open position, in accordance with an embodiment of the present specification.

FIG. 8S illustrates a cross sectional rear view of a biopsy forceps 800 in an open position, in accordance with an embodiment of the present specification. The position of the cross section depicted in FIG. 8S is at the junction point 820 of FIGS. 8E and 8F. Linkage 816 is connected by means of pin 806 to slots 805 of jaw 804. A first end of pin 806 is positioned within a slot 805 on a left side of jaw 804 and a second end of pin 806, opposite said first end, is positioned within a slot 805 on a right side of jaw 804. Similarly, linkage 821 is connected by means of pin 810 to slots 809 of jaw 808. Needle drive wire 802 passes through spring wire jacket 814. A first end of pin 810 is positioned within a slot 809 on a left side of jaw 808 and a second end of pin 810, opposite said first end, is positioned within a slot 809 on a right side of jaw 808.

The proximal portions of the linkages 816, 821 are depicted connected to the needle drive 802. Referring to FIGS. 8A through 8S, longitudinal movement of the needle drive wire 802 within the spring wire jacket 814 is translated, at pivot points on said needle drive wire 802, to up and down movement of linkage 816 and linkage 821 at the distal end of the forceps 800. This up and down movement of the linkages 816, 821 causes the pins 806, 810 to move back and forth within the slots 805, 809 respectively, causing the jaws 804, 808 to open and close. The inclusion of the slots 805, 809 and ability of the pins 806, 810 to slide within said slots 805, 809 provides offset pivot points for the jaws 804, 808 on the clevis 812. Referring to FIGS. 8B through 8F, the pivot points 804a, 804b, 808a, 808b for the jaws 804, 808 are depicted on the left and right protrusions 824, 826 of the clevis 812.

Referring again to FIGS. 8A through 8N, to open the jaws 804, 808, in one embodiment, an operator pushes in on a handle at the proximal end of the forceps 800. This pushing motion results in longitudinal distal motion of the needle drive wire 802 within the spring wire jacket 814. At a junction point 820 connecting the first linkage 816 and second linkage 821 to the distal end of the needle drive wire 802, the distal motion causes a pivoting of each linkage 816, 821 such that a distal end of linkage 816 extends upward and a distal end of linkage 821 extend downwards. Upward movement of the distal end of linkage 816 causes pin 806 to slide distally within slots 805, resulting in upward movement of the distal end of the first jaw 804 relative to pivot points 804a, 804b on the left protrusion 824 and right protrusion 826 respectively, of the clevis 812. Downward movement of the distal end of linkage 821 causes pin 810 to slide distally within slots 809, resulting in downward movement of the distal end of the second jaw 808 relative to pivot points 808a, 808b on the left protrusion 824 and right protrusion 826 respectively, of the clevis.

To close the jaws 804, 808, an operator pulls back on the forceps 800 handle, causing longitudinal movement of the needle drive wire 802 in a proximal direction within the spring wire jacket 814. At a junction point 820 connecting the first linkage 816 and second linkage 821 to the distal end of the needle drive wire 802, the proximal motion causes pivoting of each linkage 816, 821 such that a distal end of linkage 816 extends downward and a distal end of linkage 821 extends upward. Downward movement of the distal end of linkage 816 causes pin 806 to slide proximally within slots 805, resulting in downward movement of the distal end of the first jaw 804 relative to pivot points 804a, 804b on the left protrusion 824 and right protrusion 826 respectively, of the clevis 812. Upward movement of the distal end of linkage 821 causes pin 810 to slide proximally within slots 809, resulting in upward movement of the distal end of the second jaw 808 relative to pivot points 808a, 808b on the left protrusion 824 and right protrusion 826 respectively, of the clevis.

Figure 9A:
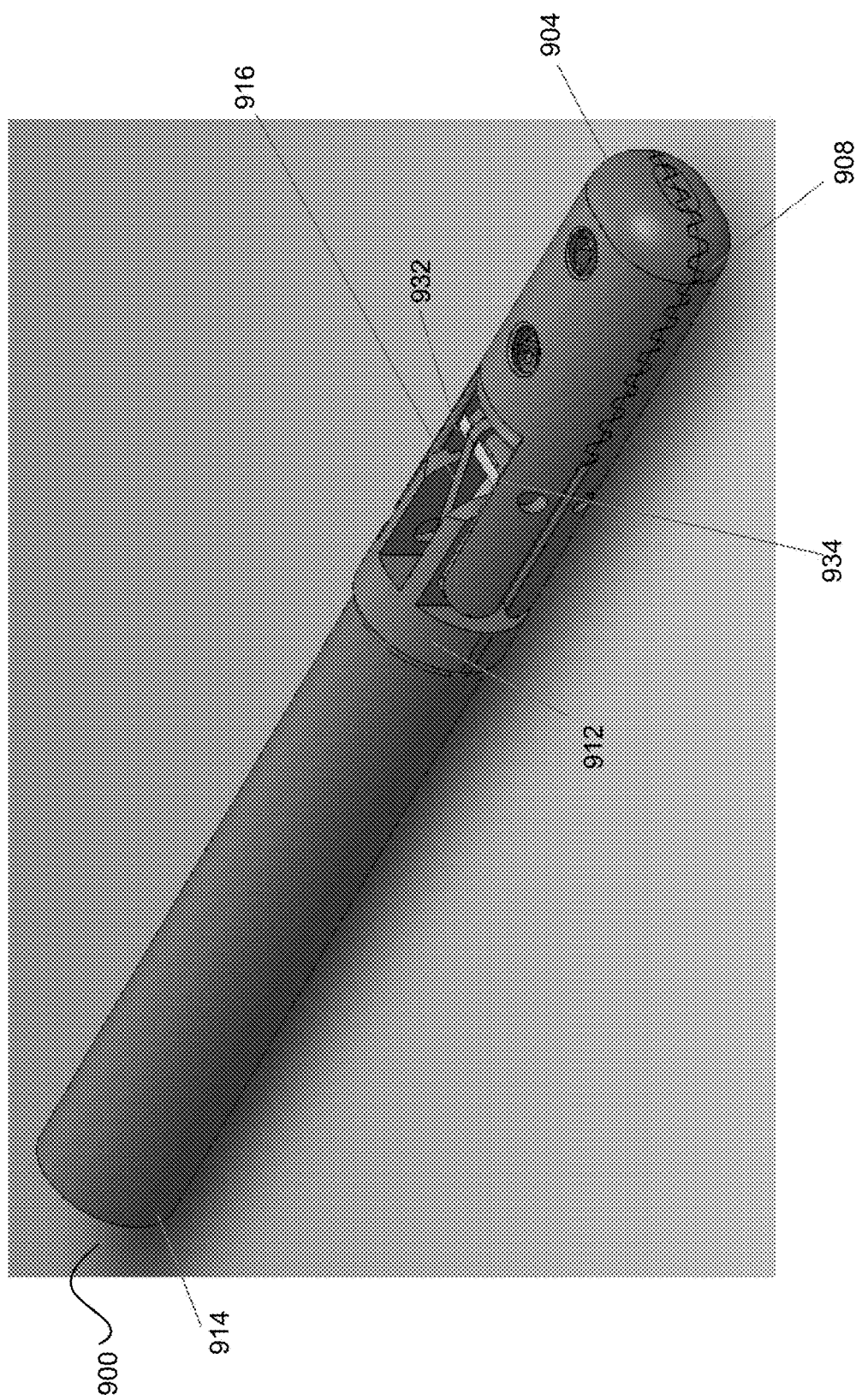
FIG. 9A illustrates an isometric view of another embodiment of a biopsy forceps in a closed position.

FIG. 9A illustrates an isometric view of another embodiment of a biopsy forceps 900 in a closed position. FIG. 9A illustrates forceps 900 comprising a spring wire jacket 914 coupled at a distal end with a proximal end of a coupling unit or clevis 912. A distal end of clevis 912 is coupled with proximal ends of a first jaw 904 and a second jaw 908. The first jaw 904 is also coupled with a linkage 916, a small clip 932 and a large clip 934.

Figure 9B:
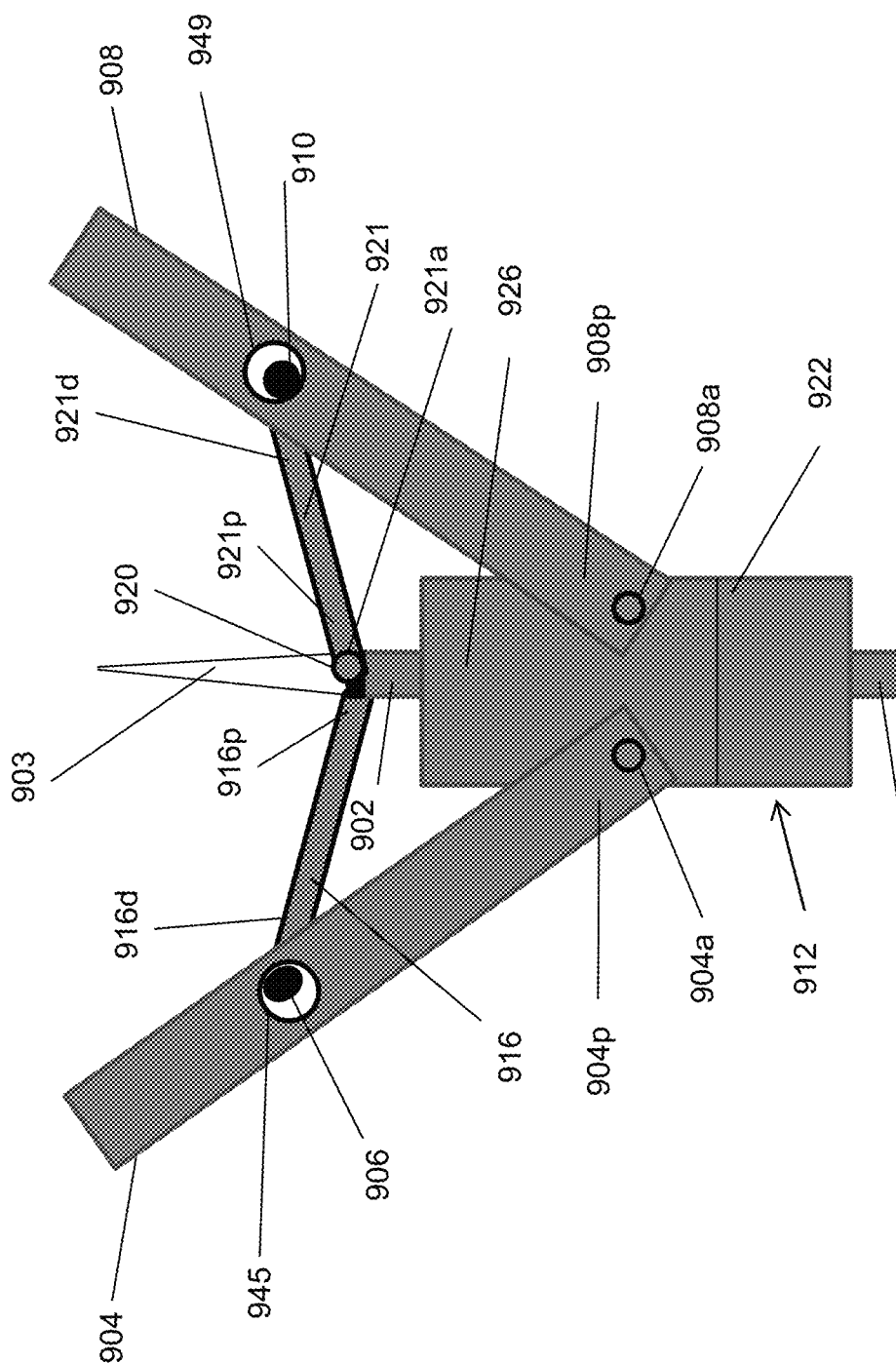
FIG. 9B illustrates a right side exemplary block diagram of the clevis of the biopsy forceps, in accordance with an embodiment of the present specification.

FIG. 9B illustrates a right side block diagram of an exemplary embodiment of the clevis portion 912. Clevis 912 is a stationary fixed base that holds the pivot points of jaws 904, 908. The clevis 912 comprises a base portion 922 and a left distal protrusion (not shown) and a right distal protrusion 926. A proximal left end (not shown) of the first jaw 904 is attached to said left distal protrusion (not shown) at a first jaw pivot point 904a and a proximal left end of the second jaw 908 is attached to said left distal protrusion (not shown) at a second jaw pivot point 908a. A proximal right end 904p of the first jaw 904 is attached to said right distal protrusion 926 at said first jaw pivot point 904a and a proximal right end 908p of the second jaw 908 is attached to said right distal protrusion 926 at said second jaw pivot point 908a.

The distal end of the needle drive wire 902 includes a first linkage pivot point (not shown) and a second linkage pivot point 921a. The first linkage pivot point (not shown) is positioned to the left of the needle drive wire 902 and allows for pivoting of the first linkage 916 relative to the needle drive wire 902. The second linkage pivot point 921 is positioned to the right of the needle drive wire 902 and allows for pivoting of the second linkage 921 relative to the needle drive wire 902. The pivot point (not shown) of linkage 916 and the pivot point 921a of linkage 921 are offset, both longitudinally (being located further distally on the device) and laterally, from the pivot points 904a, 908a of jaws 904, 908. Proximal ends 916p and 921p of the linkages 916 and 921 respectively, are connected at a junction point 920 to the needle drive wire 902 such that the proximal ends 916p and 921p of the linkages 916, 921 move proximally and distally with the needle drive wire 902 and pivot about said needle drive wire 902 as the needle drive wire 902 is moved longitudinally with respect to the clevis 912. The distal ends 916d and 921d of the linkages 916, 921 are coupled with pins 906 and 910 respectively. The pins 906, 910 are positioned within openings 945, 949 of the first jaw 904 and second jaw 908 respectively. In one embodiment, jaw 904 includes only one opening 945 on one side of said jaw 904. In another embodiment, jaw 904 includes an opening 945 on each side. In one embodiment, jaw 908 includes only one opening 949 on one side of said jaw 908. In another embodiment, jaw 908 includes an opening 949 on each side.

When the needle drive wire 902 is pushed distally using the device handle, the linkages 916, 921 move distally and rotate about their pivot points on the needle drive wire 902, causing the pins 905, 910 to rotate within the openings 945, 949 and push on the jaws 904, 908 which results in the jaws 904, 908 pivoting about their pivot points on the clevis protrusion 926 and opening. When the needle drive wire 902 is pulled proximally using the device handle, the linkages 916, 921 move proximally and rotate about their pivot points on the needle drive wire 902, causing the pins 906, 910 to rotate within the openings 945, 949 and pull on the jaws 904, 908 which results in the jaws 904, 908 rotating about their pivot points on the clevis protrusion 926 and closing. This cam mechanism causes the jaws 904, 908 to open and close. Attached to the needle drive wire 902 distal to said junction point 920 is a needle 903 used for piercing tissues. The needle 903 also moves proximally and distally with longitudinal movement of the needle drive wire 902. Therefore, in one embodiment, as the device handle is pushed distally to open the jaws 904, 908, the needle 903 is extended distally. As the device handle is pulled proximally to close the jaws 904, 908, the needle 903 is retracted.

As described above, the clevis 912, which is a coupling unit, has two different pivoting points, one each for connecting with of the first jaw 904 and the second jaw 908. Referring again to FIG. 9B, pivot points 904a and 908a on distal protrusion 926 of clevis 912 are the same distance longitudinally from an end of the clevis 912, but are offset laterally. The right side of jaw 904 is connected to pivoting point 904a while the right side of jaw 908 is connected to pivoting point 908a.

Figure 9D:
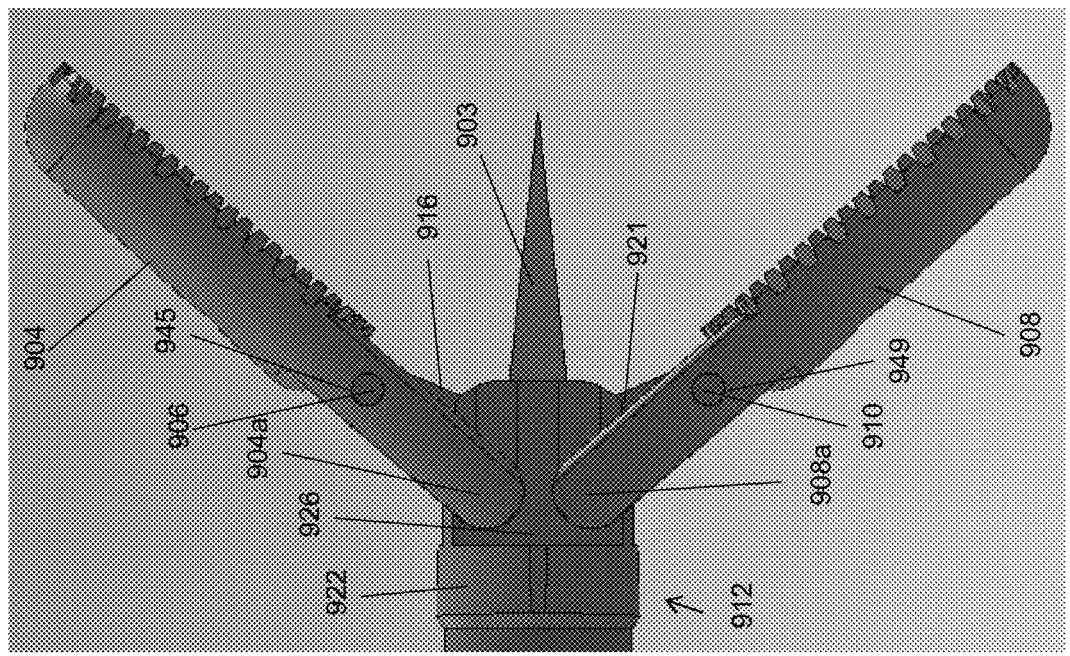
FIG. 9D is a right side view illustration of the clevis and jaws of one embodiment of the biopsy forceps device of the present specification.
Figure 9C:
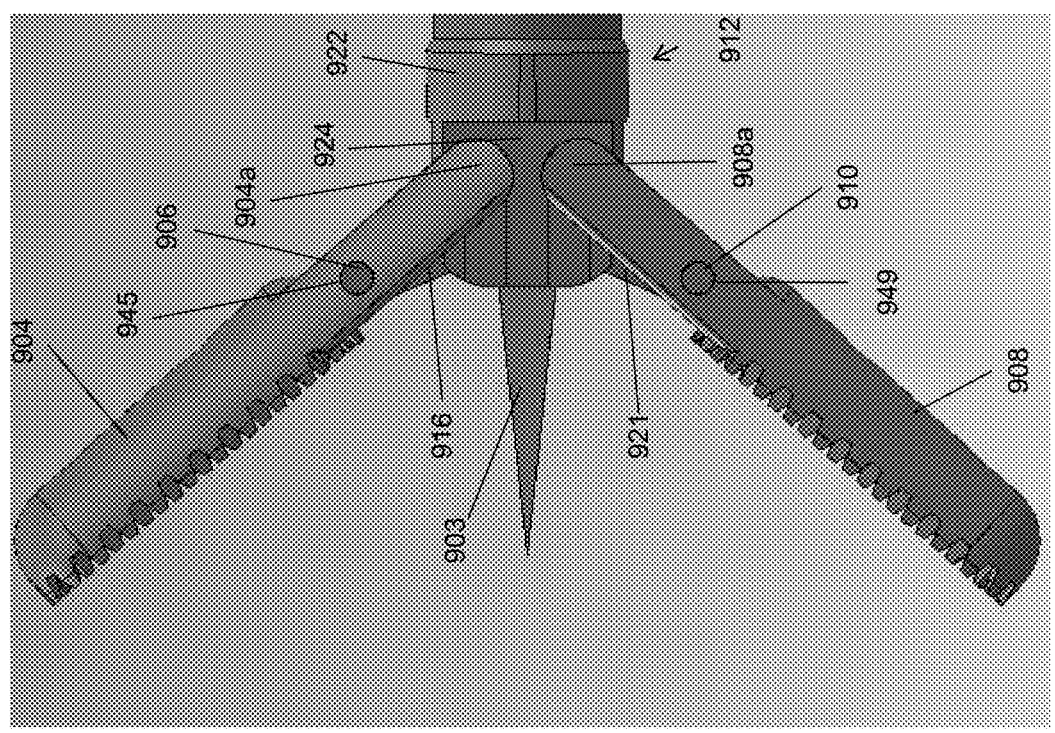
FIG. 9C is a left side view illustration of the clevis and jaws of one embodiment of the biopsy forceps device of the present specification.
Figure 9F:
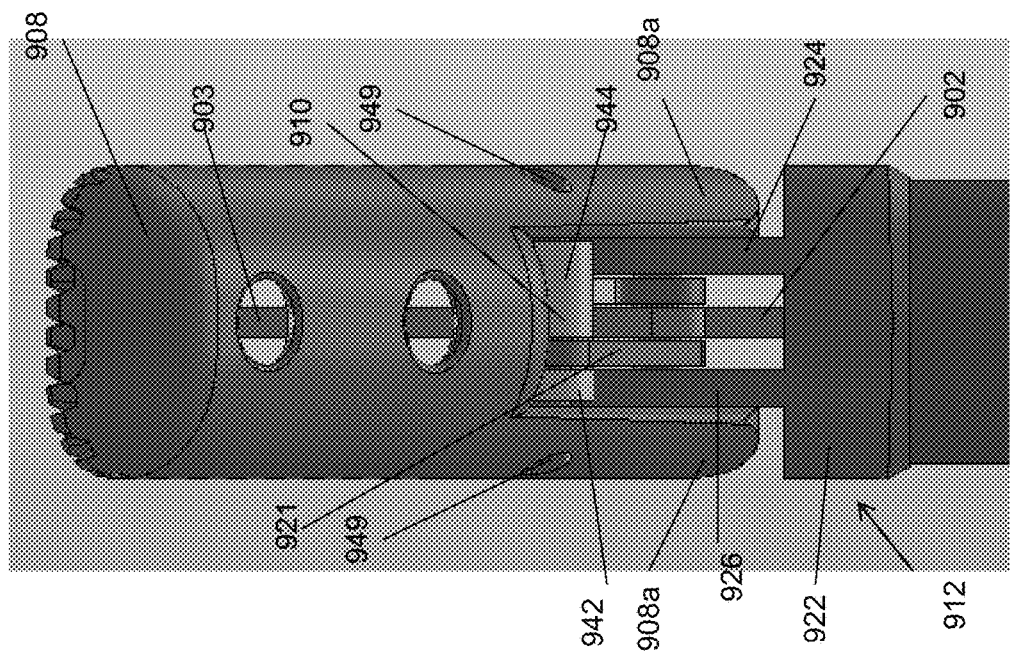
FIG. 9F is a bottom-up view illustration of the clevis and jaws of one embodiment of the biopsy forceps device of the present specification.
Figure 9E:
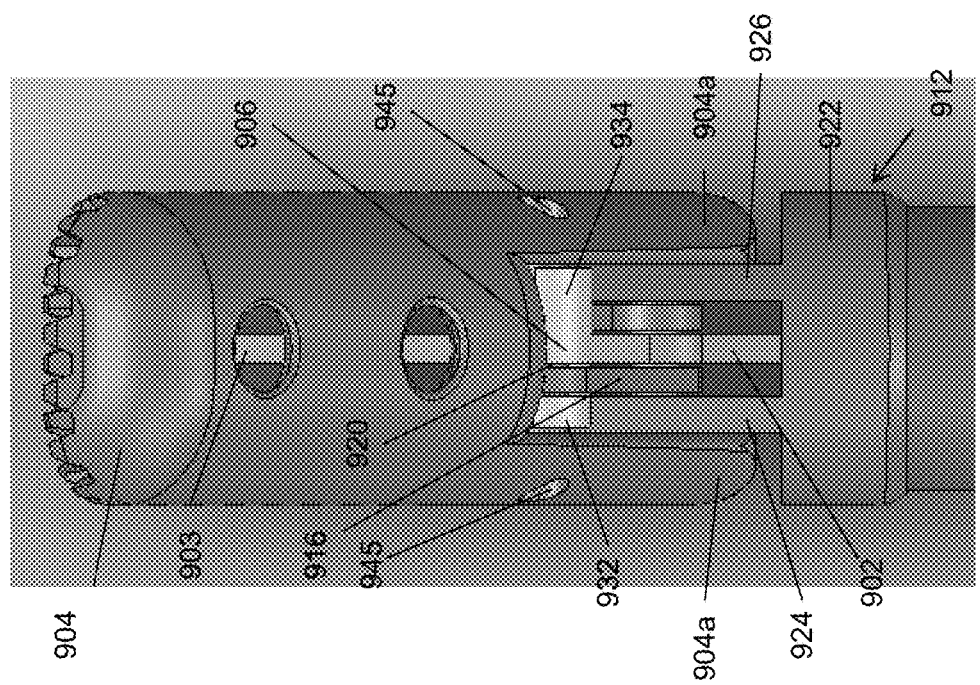
FIG. 9E is a top-down view illustration of the clevis and jaws of one embodiment of the biopsy forceps device of the present specification.

FIGS. 9C and 9D are left and right side view illustrations respectively, of the clevis 912 and jaws 904, 908 of one embodiment of the biopsy forceps device of the present specification. FIGS. 9E and 9F are top-down and bottom-up view illustrations respectively, of the clevis 912 and jaws 904, 908 of one embodiment of the biopsy forceps device of the present specification. Referring to FIGS. 9C through 9F simultaneously, the clevis 912 includes a base portion 922, a left protrusion 824, and a right protrusion 826. The left proximal end of the first jaw 904 is attached to the left protrusion 924 at a first jaw pivot point 904a and the left proximal end of the second jaw 908 is attached to the left protrusion 924 at a second jaw pivot point 908a. The right proximal end of the first jaw 904 is attached to the right protrusion 926 at said first jaw pivot point 904a and the right proximal end portion of the second jaw 908 is attached to the right protrusion 926 at said second jaw pivot point 908a. First jaw pivot point 904a and second jaw pivot point 908a are offset laterally with respect to one another but are at the same longitudinal position on the biopsy forceps device.

The first jaw 904 includes an opening 945 on its left side and right side. A first pin 906 is positioned with its ends within these openings 945. A first linkage 916, having a proximal end and a distal end, is attached with its distal end to the first pin 906. The proximal end of the first linkage 916 is attached to a junction point 920 on a needle drive wire 902. A small clip 932 and a large clip 934 are positioned over the pin 906 and prevent lateral movement of the pin 906 to keep it from falling out of the openings 945. The second jaw 908 includes an opening 949 on its left side and right side. A second pin 910 is positioned with its ends within these opening 949. A second linkage 921, having a proximal end and a distal end, is attached with its distal end to the second pin 910. The proximal end of the second linkage 921 is attached to a junction point 920 on a needle drive wire 902. A small clip 942 and a large clip 944 are positioned over the pin 910 and prevent lateral movement of the pin 910 to keep it from falling out of the openings 949. Opening and closing of the jaws 904, 908 is effectuated by longitudinal movement of the needle drive wire 902 which is translated to movement and pivoting of the linkages 916, 921 and rotations of the pins 906, 910 within the openings 945, 949 causing pivoting of the proximal ends of the jaws 904, 908 about their pivot points 904a, 908a as described above. The junction point 920, where the first linkage 916, second linkage 921, and needle drive wire 902 are coupled together, is positioned between the left protrusion 924 and right protrusion 926 of the clevis 912. A needle 903 is attached to, and extends distally from, the junction point 920.

Figure 9G:
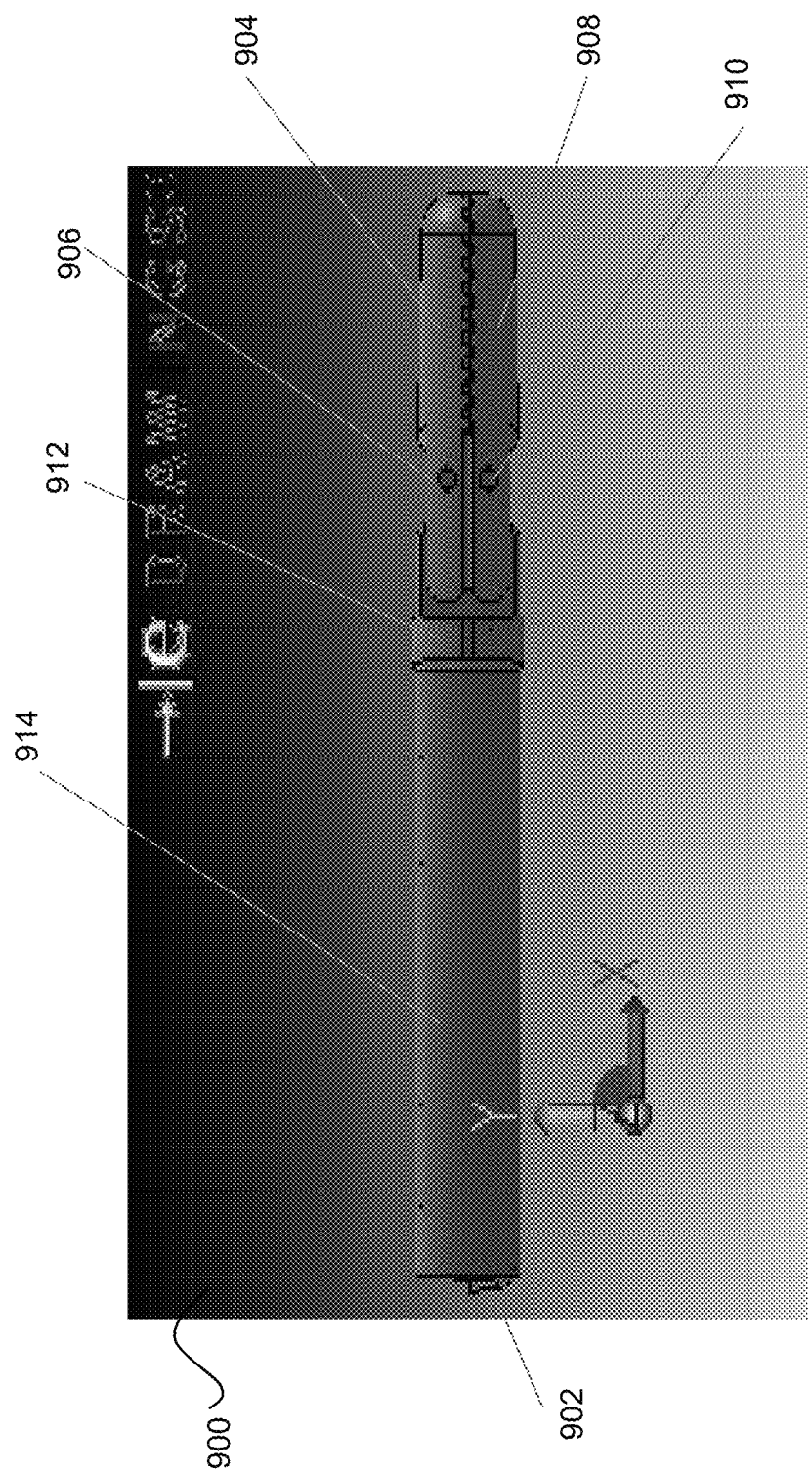
FIG. 9G illustrates a right side view of another embodiment of a biopsy forceps in a closed position.

FIG. 9G illustrates a right side view of another embodiment of a biopsy forceps 900 in a closed position. Forceps 900 comprise a needle drive wire 902, a first jaw 904 coupled with a first pin 906, a second jaw 908 coupled with a second pin 910, a clevis 912 and a spring wire jacket 914.

Figure 9H:
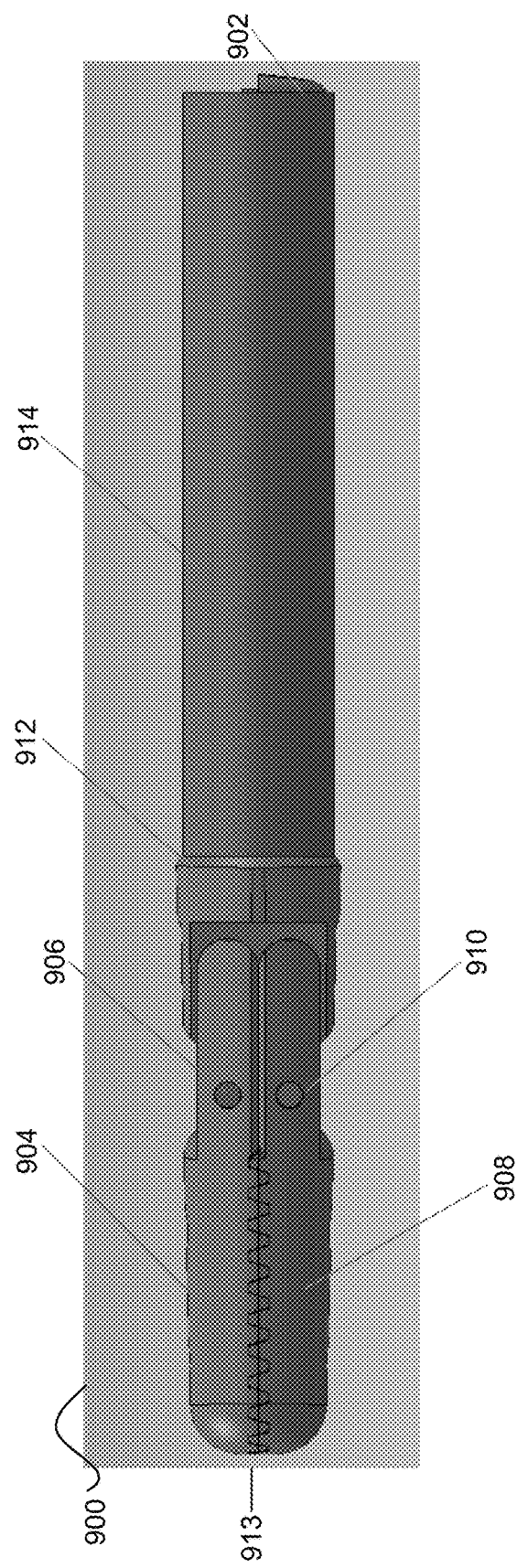
FIG. 9H illustrates a left side view of another embodiment of biopsy forceps in a closed position.

FIG. 9H illustrates a left side view of another embodiment of biopsy forceps 900 in a closed position. First jaw 904 is coupled with first pin 906 and second jaw 908 is coupled with second pin 910. Needle drive wire 902 passes through spring wire jacket 914 and emerges as a needle through clevis 912. The front face 913 of the forceps is squared off, allowing for a larger sample size as more tissue is collected on the sides of the bite as compared to a rounded front face.

Figure 9I:
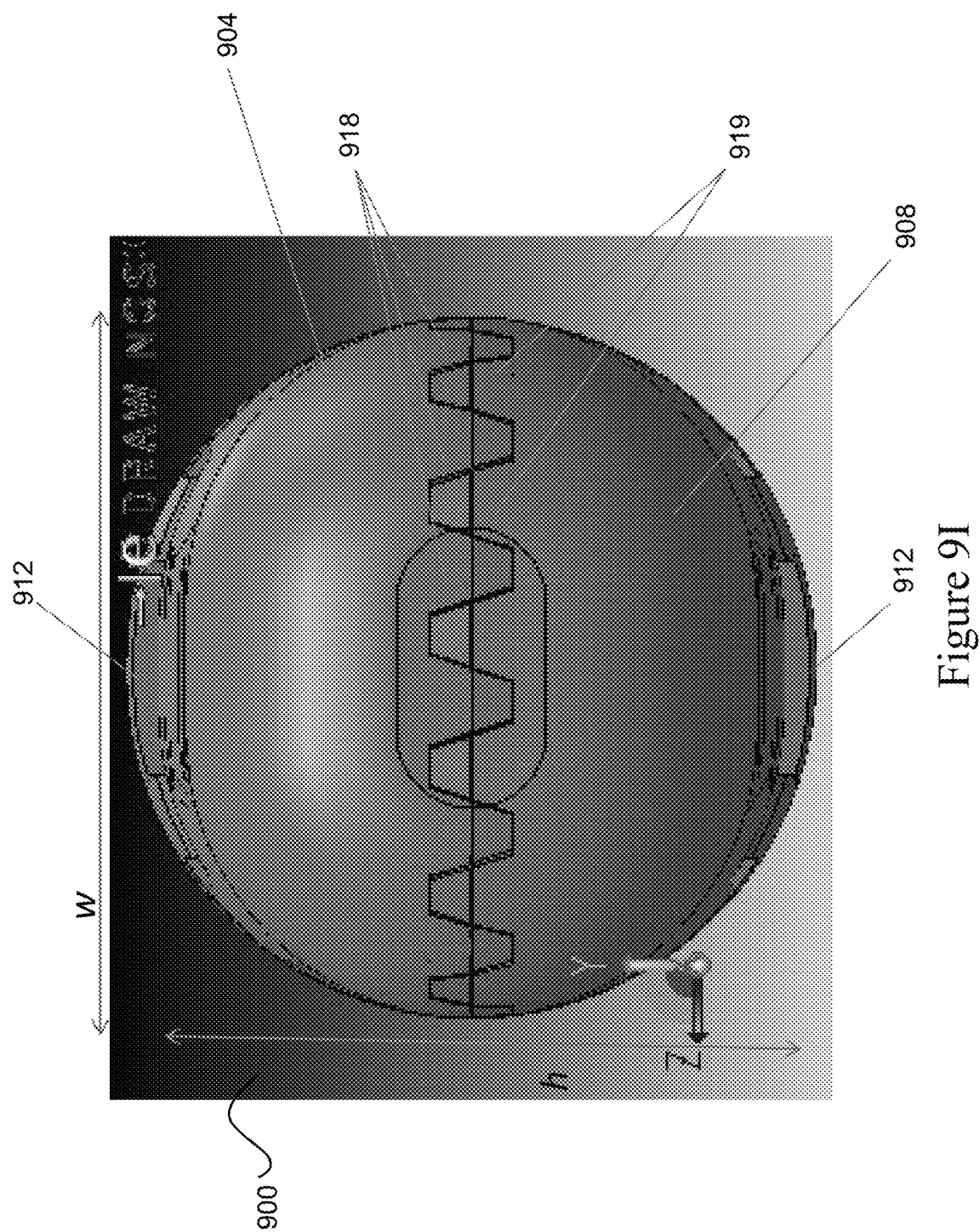
FIG. 9I illustrates a front view of the embodiment of the biopsy forceps of FIG. 9A in a closed position.

FIG. 9I illustrates a front view of the embodiment of the biopsy forceps 900 of FIG. 9A in a closed position. As seen in the figure, teeth 918 of jaw 904 interlock with teeth 919 of jaw 908 in a closed position, such that there are no gaps between the interlocking teeth 918 and 919. A portion of clevis 912 coupled with jaws 904 and 908 is also visible in the figure. Referring to FIGS. 9D and 8D simultaneously, the forceps 900 of FIG. 9D has a more oval shaped distal end, with a width w greater than a height h, compared to the forceps 800 of FIG. 8D, allowing for a bite having a greater width.

Figure 9J:
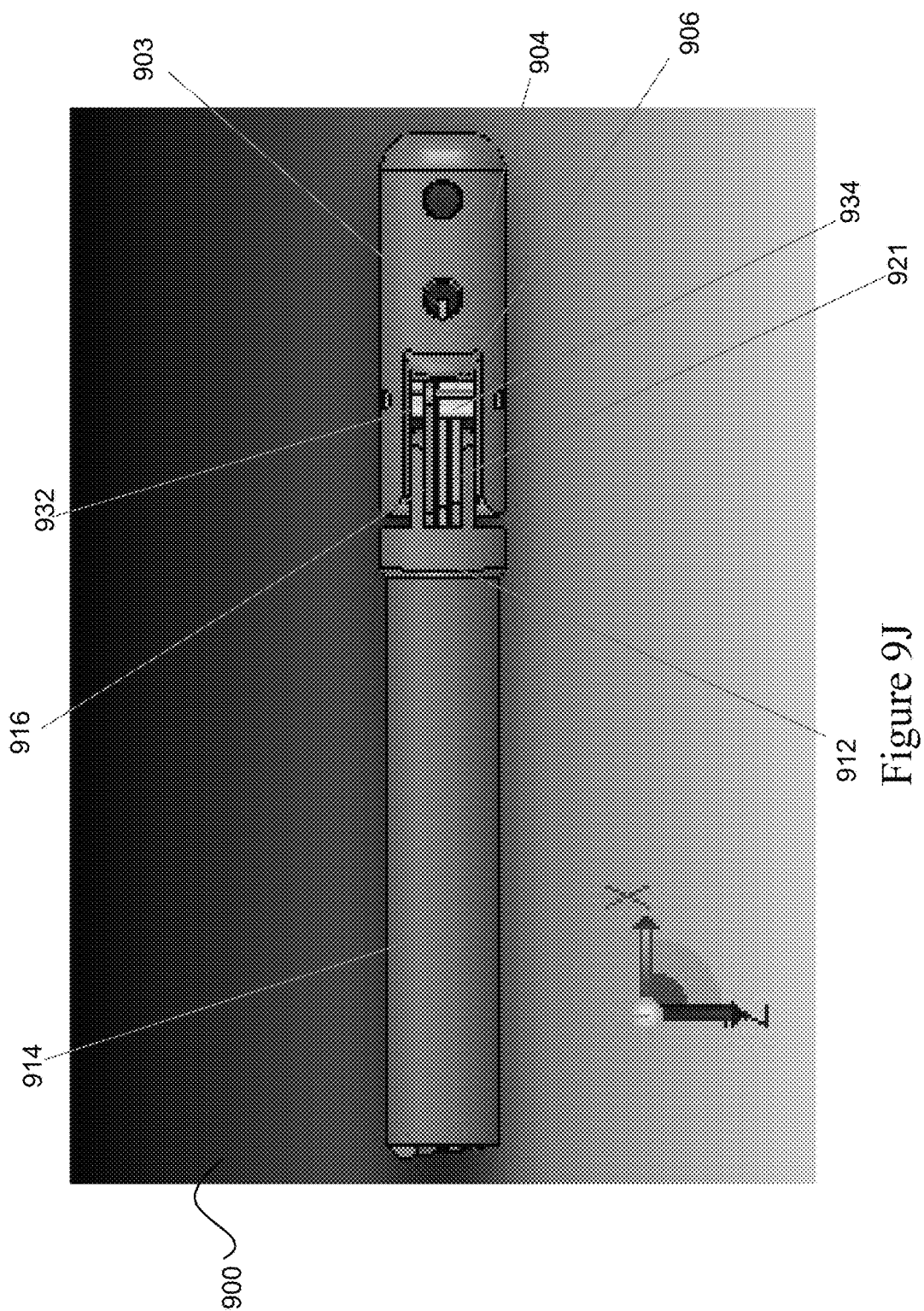
FIG. 9J illustrates a top-down view of the embodiment of the biopsy forceps of FIG. 9A in a closed position.

FIG. 9J illustrates a top-down view of the embodiment of the biopsy forceps 900 of FIG. 9A in a closed position. Jaw 904 is coupled with pin 906, linkage 916, a small clip 932 and a large clip 934. Small clip 932 and large clip 934 hold pin 906 and linkage 916 from releasing each other. Linkage 916 is connected at a junction point to the needle drive wire extending longitudinally through sleeve wire jacket 914 and works in conjunction with pin 906, small clip 932 and large clip 934 enabling movement of jaw 904. Small clip 932 and large clip 934 are designed to keep the pin 906 and the linkage 916 aligned with each other. The needle drive wire passes through spring wire jacket 914 and emerges as a needle 903 through clevis 912 between linkages 916 and 921.

Figure 9K:
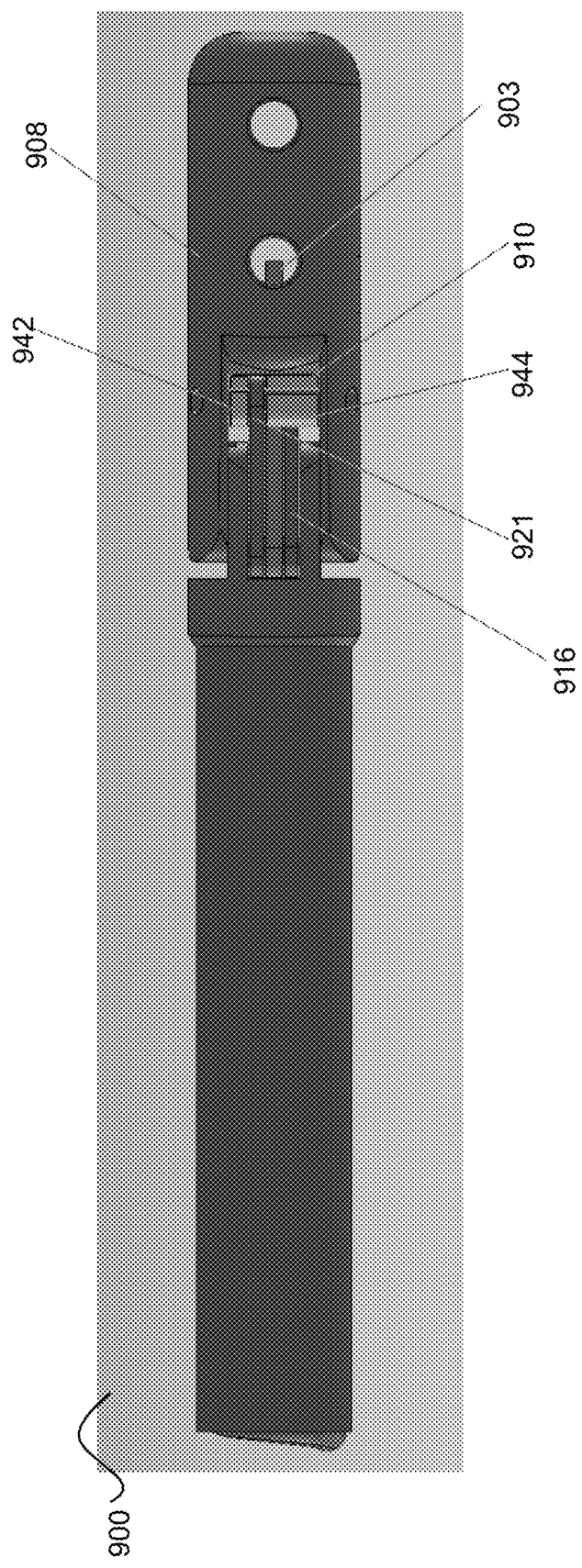
FIG. 9K illustrates a bottom-up view of the embodiment of the biopsy forceps of FIG. 9A in a closed position.

FIG. 9K illustrates a bottom-up view of the embodiment of the biopsy forceps 900 of FIG. 9A in a closed position. Jaw 908 is coupled with linkage 921, pin 910, a small clip 942 and a large clip 944. Linkage 921 is connected at a junction point to the needle drive wire extending longitudinally through sleeve wire jacket 914 and works in conjunction with pin 910, small clip 942 and large clip 944 enabling movement of jaw 908. Small clip 942 and large clip 944 are designed to keep the pin 910 and the linkage 921 aligned with each other. The needle drive wire passes through spring wire with jacket 914 and emerges as a needle 903 through clevis 912 between linkages 916 and 921.

Figure 9L:
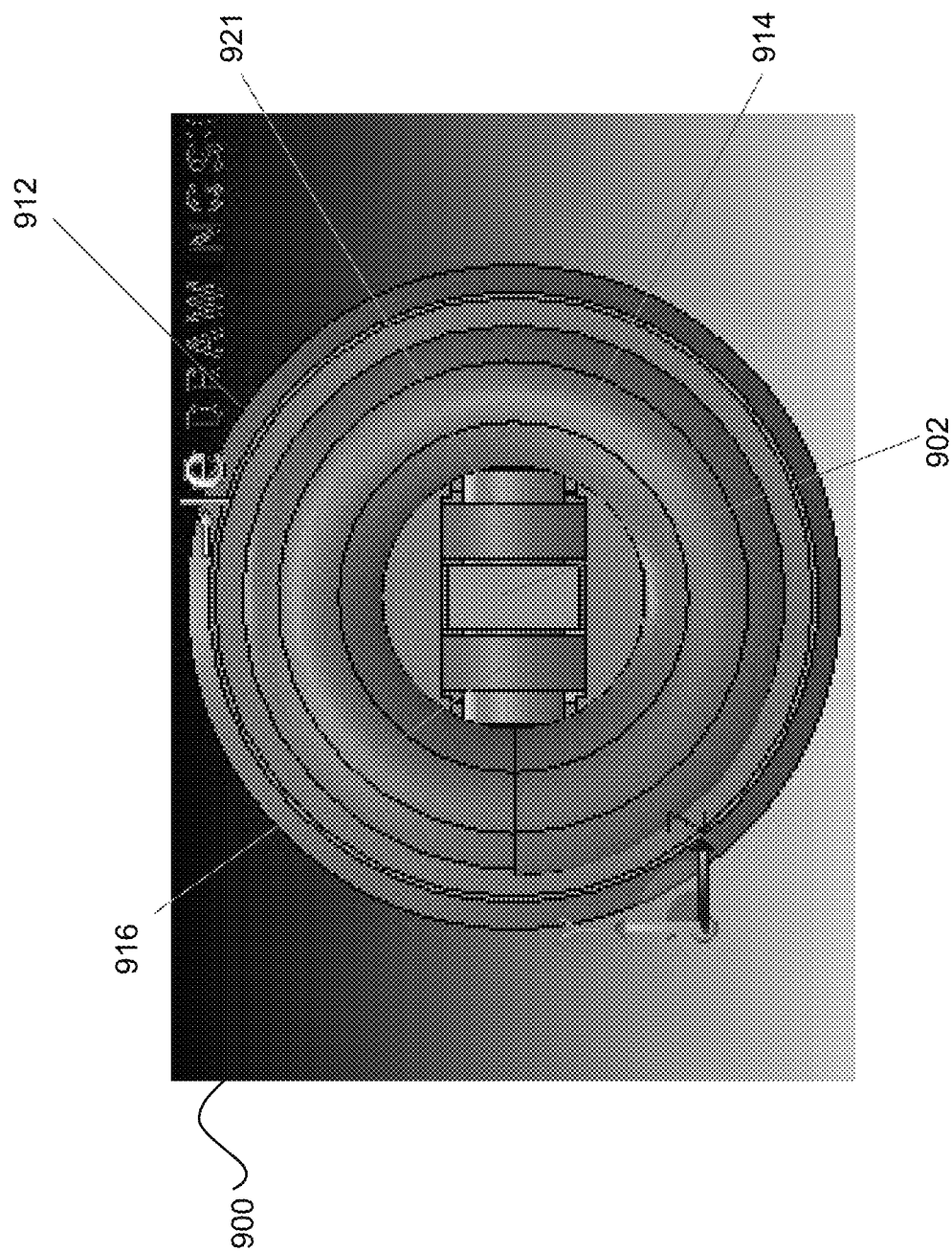
FIG. 9L illustrates a cross sectional rear view of the embodiment of the biopsy forceps of FIG. 9A in a closed position.

FIG. 9L illustrates a cross sectional rear view of the embodiment of the biopsy forceps 900 of FIG. 9A in a closed position. The position of the cross section depicted in FIG. 9L is at the junction point 920 of FIGS. 9E and 9F. Referring to FIGS. 9A through 9L, needle drive wire 902 passes through spring wire jacket 914 and emerges through clevis 912 as a needle 903 on an opposite side of forceps 900 between jaws 904 and 908. Linkages 916 and 921 are positioned on either side of needle 903 for supporting movement of the jaws 904 and 908. The spring wire jacket 914 is depicted surrounding the proximal portions of the linkages 916, 921 and needle drive wire 902.

Figure 9M:
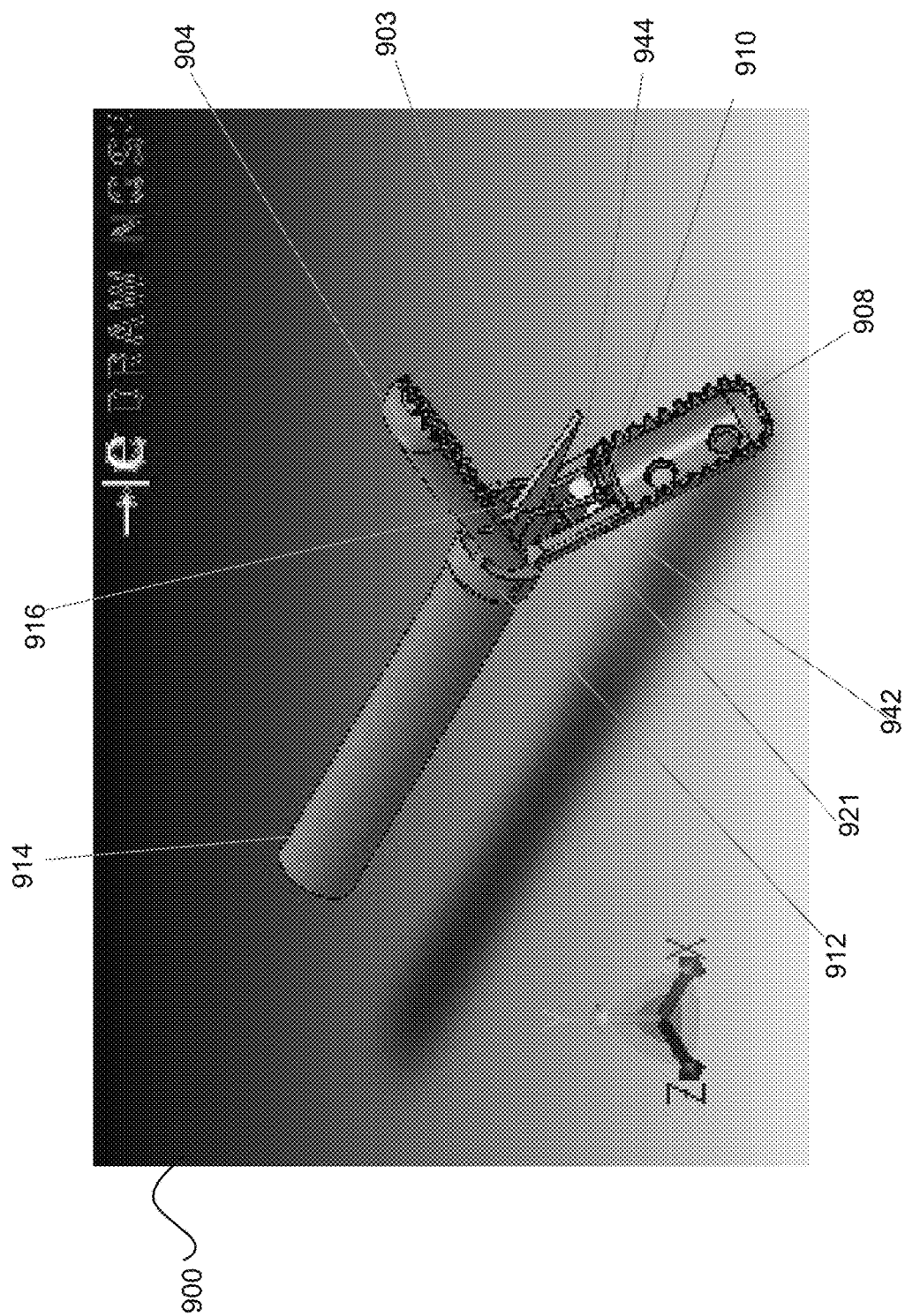
FIG. 9M illustrates the embodiment of the biopsy forceps of FIG. 9A in an open position.

FIG. 9M illustrates the embodiment of the biopsy forceps 900 of FIG. 9A in an open position. Forceps 900 are shown with jaws 904 and 908 in an open position with linkages 916 and 921 supporting the jaws 904, 908. As can be seen in FIG. 9M, linkage 921 emerges from behind the right distal protrusion of clevis 912, where it is connected via a junction point to the needle drive wire extending longitudinally within the spring wire jacket 914, and connects via small clip 942, large clip 944, and pin 910 to the second jaw 908. The needle drive wire passes through spring wire jacket 914 and emerges as needle 903 through clevis 912 between jaws 904 and 908.

Figure 9N:
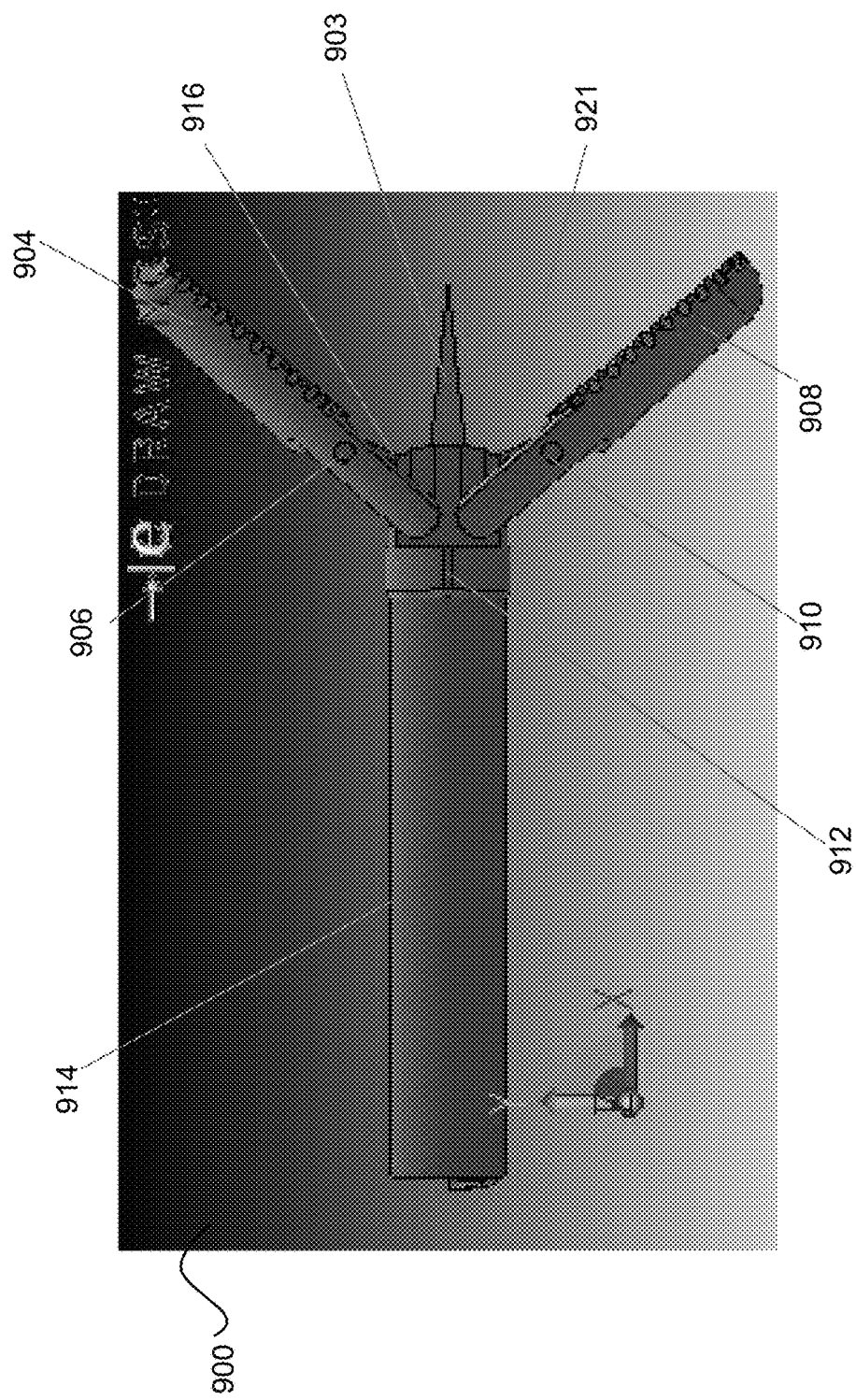
FIG. 9N illustrates a right side view of the embodiment of the biopsy forceps of FIG. 9A in an open position.

FIG. 9N illustrates a right side view of the embodiment of the biopsy forceps 900 of FIG. 9A in an open position. Pin 906 connects linkage 916 with jaw 904 and pin 910 connects linkage 921 with jaw 908. In one embodiment, in an open position, jaws 904 and 908 are at an angle of approximately 45 degrees with respect to each other. The needle drive wire passes through spring wire jacket 914 and emerges as needle 903 through clevis 912 between jaws 904 and 908.

Figure 9O:
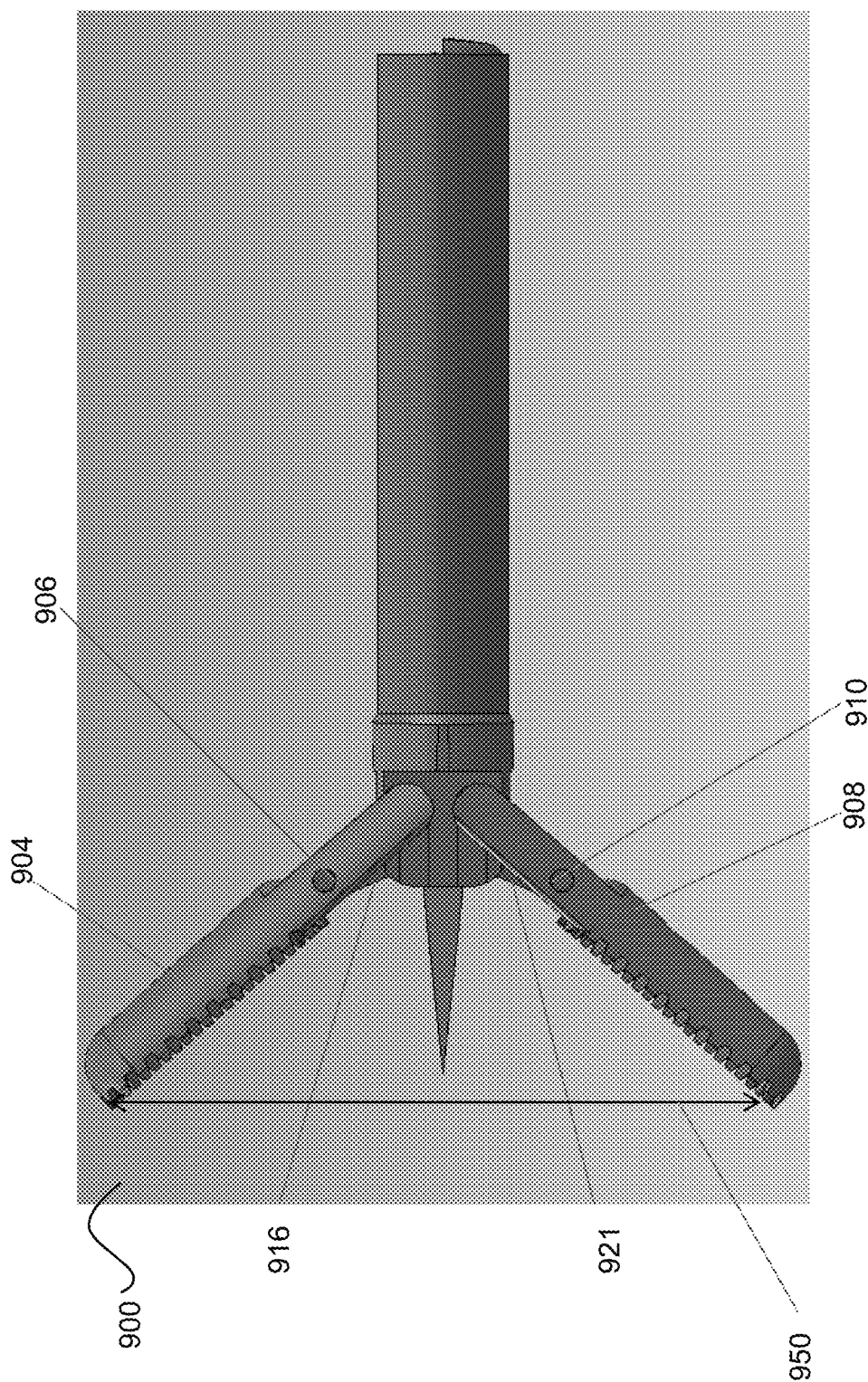
FIG. 9O illustrates a left side view of the embodiment of the biopsy forceps of FIG. 9A in an open position.

FIG. 9O illustrates a left side view of the embodiment of the biopsy forceps 900 of FIG. 9A in an open position. Pin 906 and linkage 916 enable the movement of jaw 904. Similarly, pin 910 and linkage 921 enable the movement of jaw 908. In one embodiment, distance 950 marked on FIG. 9O denotes a maximum opening distance of forceps 900.

Figure 9P:
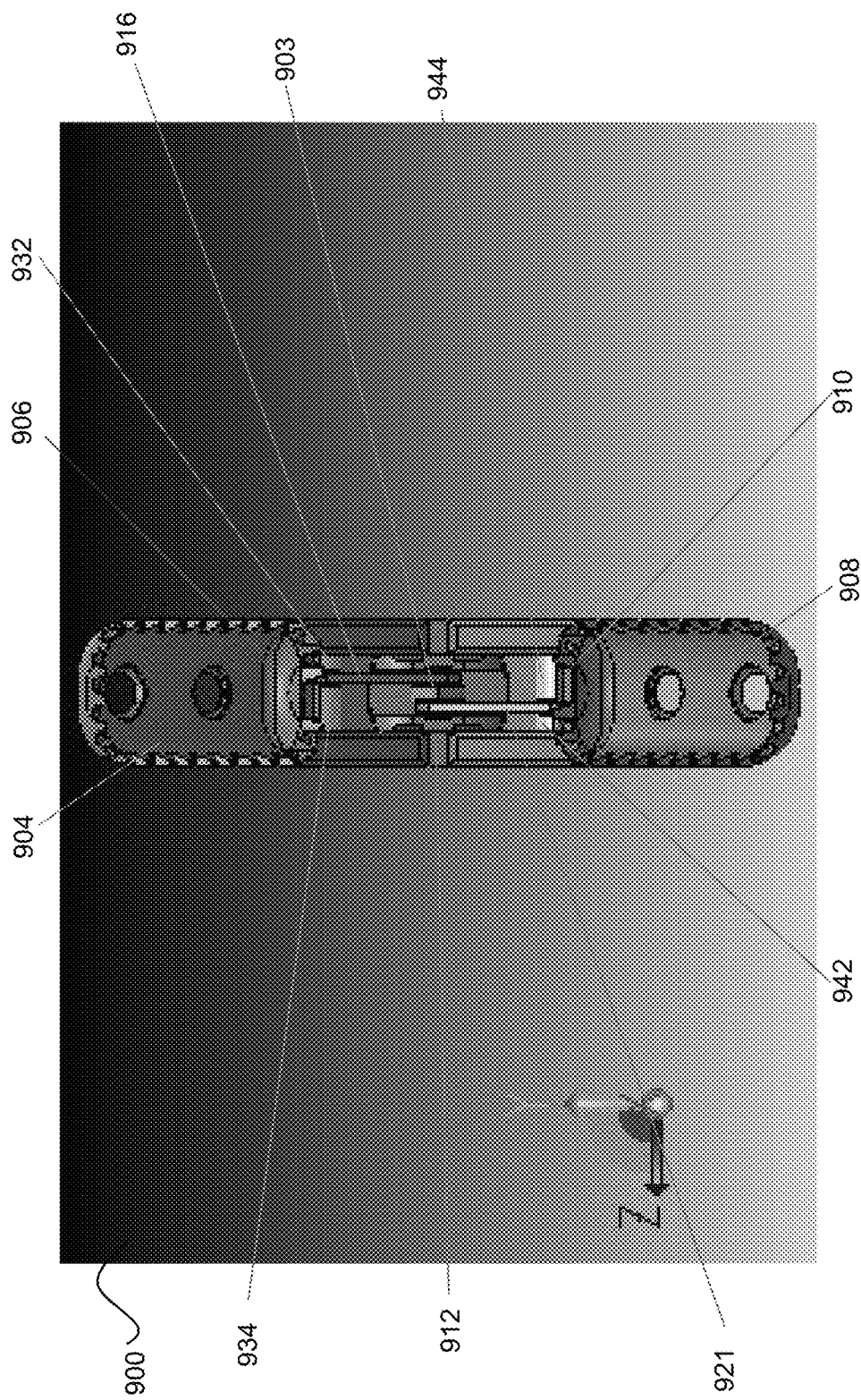
FIG. 9P illustrates a front view of the embodiment of the biopsy forceps of FIG. 9A in an open position.

FIG. 9P illustrates a front view of the embodiment of the biopsy forceps 900 of FIG. 9A in an open position. Jaw 904 is coupled with pin 906, linkage 916, a small clip 932 and a large clip 934. Linkage 916 extends toward clevis 912 and is connected to the needle drive wire extending longitudinally through the sleeve wire jacket and works in conjunction with pin 906, small clip 932 and large clip 934, enabling movement of jaw 904. Jaw 908 is coupled with linkage 921, pin 910, a small clip 942 and a large clip 944. Linkage 921 extends toward clevis 912 and is connected to the needle drive wire extending longitudinally through the sleeve wire jacket and works in conjunction with pin 910, small clip 942 and large clip 944, enabling movement of jaw 908. The needle drive wire passes through the spring wire jacket and emerges as a needle 903 through clevis 912 between jaws 904 and 908.

Figure 9Q:
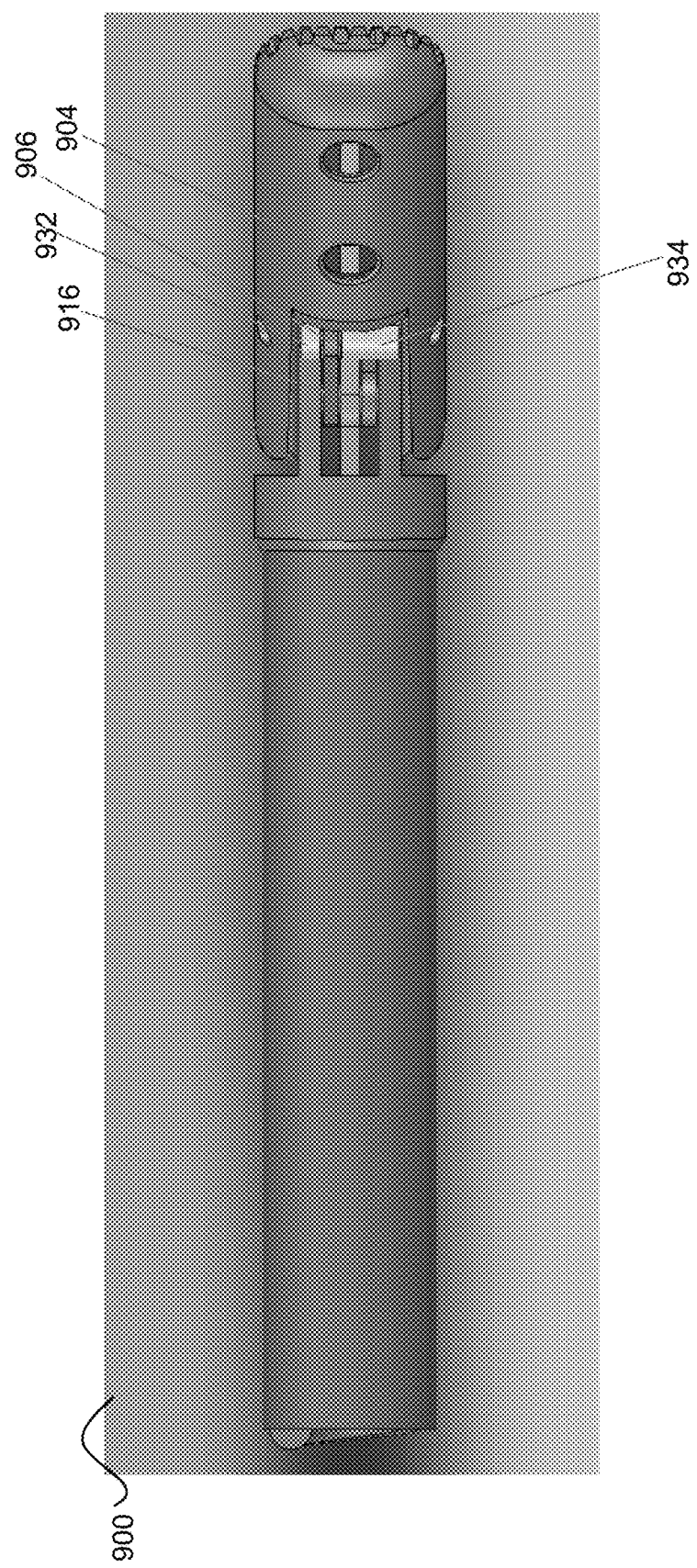
FIG. 9Q illustrates a top-down view of the embodiment of the biopsy forceps of FIG. 9A in an open position.

FIG. 9Q illustrates a top-down view of the embodiment of the biopsy forceps 900 of FIG. 9A in an open position. Jaw 904 is illustrated in an open position coupled with linkage 916, small clip 932, large clip 934, and pin 906.

Figure 9R:
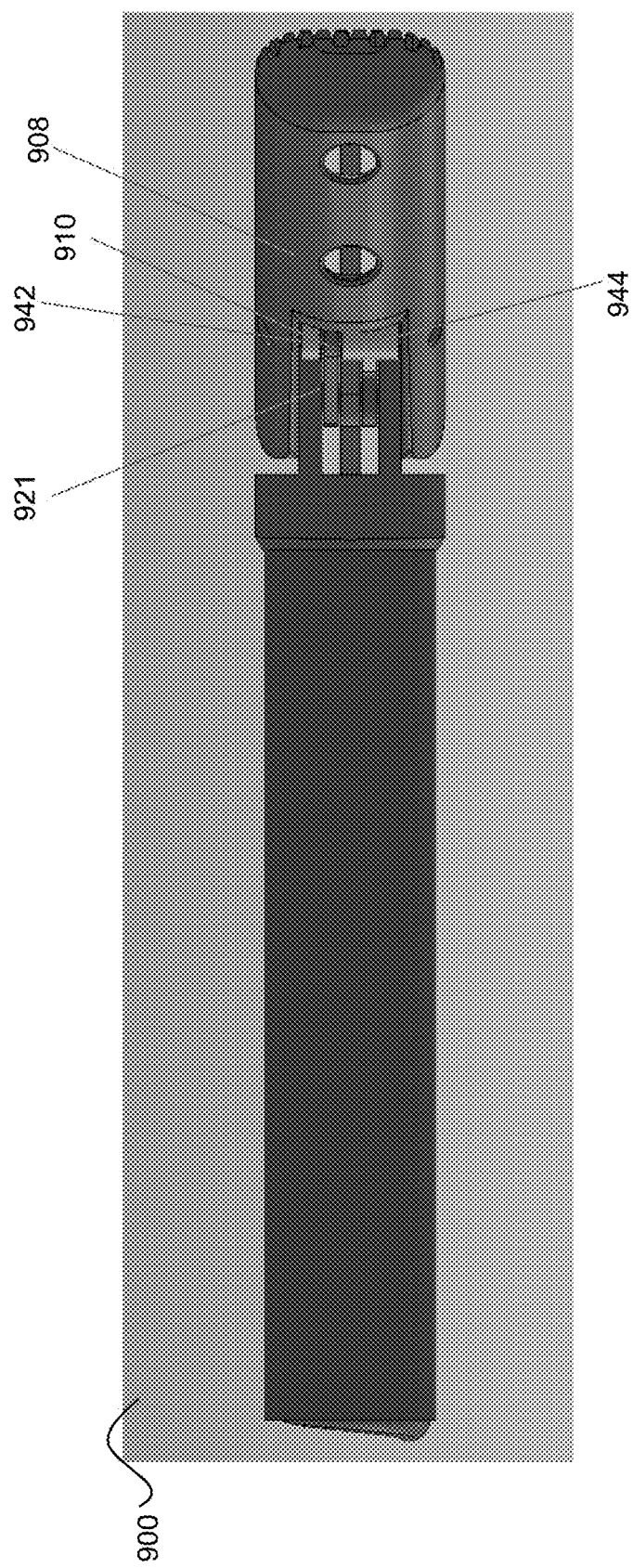
FIG. 9R illustrates a bottom-up view of the embodiment of the biopsy forceps of FIG. 9A in an open position.

FIG. 9R illustrates a bottom-up view of the embodiment of the biopsy forceps 900 of FIG. 9A in an open position. Jaw 908 is illustrated in an open position coupled with linkage 921, small clip 942, large clip 944, and pin 910.

Figure 9S:
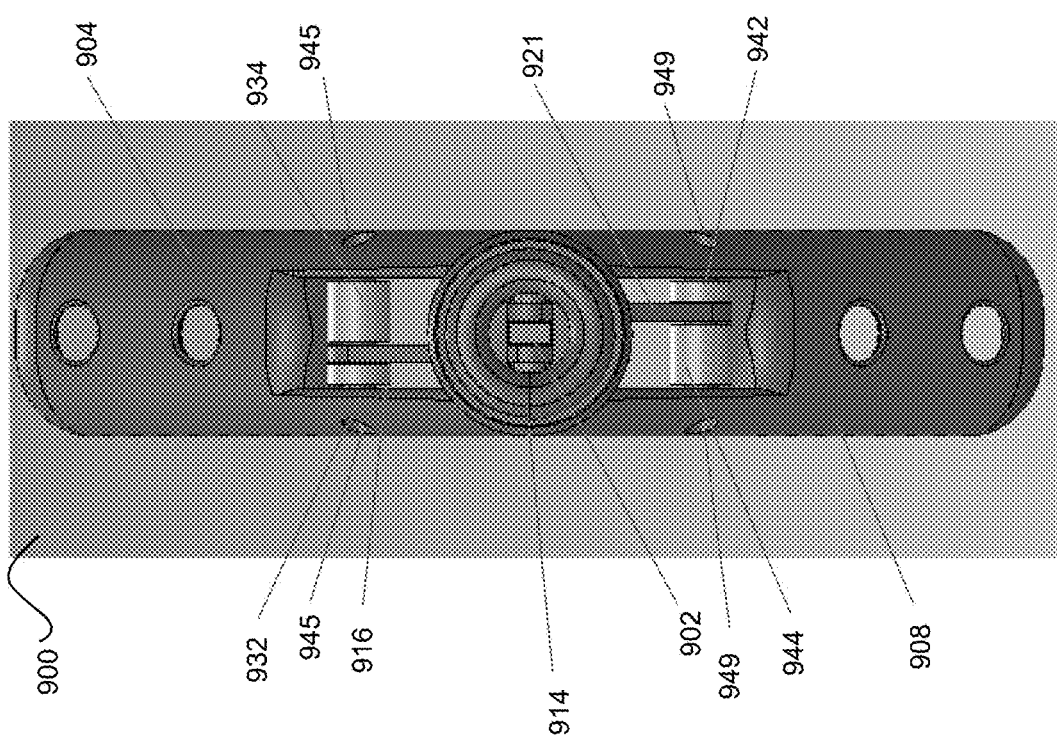
FIG. 9S illustrates a cross sectional rear view of the embodiment of the biopsy forceps of FIG. 9A in an open position.

FIG. 9S illustrates a rear view of the embodiment of the biopsy forceps 900 of FIG. 9A in an open position. The position of the cross section depicted in FIG. 9S is at the junction point 920 of FIGS. 9E and 9F. Referring to FIGS. 9A through 9S, needle drive wire 902 passes through spring wire jacket 914 and emerges as needle 903 through clevis 912 on an opposite side of forceps 900 between jaws 904 and 908. Linkages 916 and 921 are positioned on either side of needle drive wire 902 for supporting movement of the jaws 904 and 908. In the open position, jaw 904, coupled with linkage 916, small clip 932 and large clip 934 and, jaw 908, coupled with linkage 921, small clip 942 and large clip 944, extend outward from the plane of the needle drive wire 902 up to a maximum angle of 45 degrees with respect to said plane. Further, as shown in FIG. 9S, the rear view of forceps 900 in an open position illustrates small clip 932 and large clip 934 positioned on a left side and right side of linkage 916 respectively, near a distal end of linkage 916, the distal end of linkage 916 being coupled with pin 906 which is positioned within openings 945 of jaw 904. Similarly, the rear view of forceps 900 in an open position illustrates small clip 942 and large clip 944 positioned on a right side and left side of linkage 921 respectively, near a distal end of linkage 921, the distal end of linkage 921 being coupled with pin 910 which is positioned within openings 949 of jaw 908. The clips 932, 934, 942, 944 serve to position the pins 906, 910 correctly and prevent the pins 906, 910 from sliding out of openings 945 on the first jaw 904 and openings 949 on the second jaw 908.

Figure 9T:
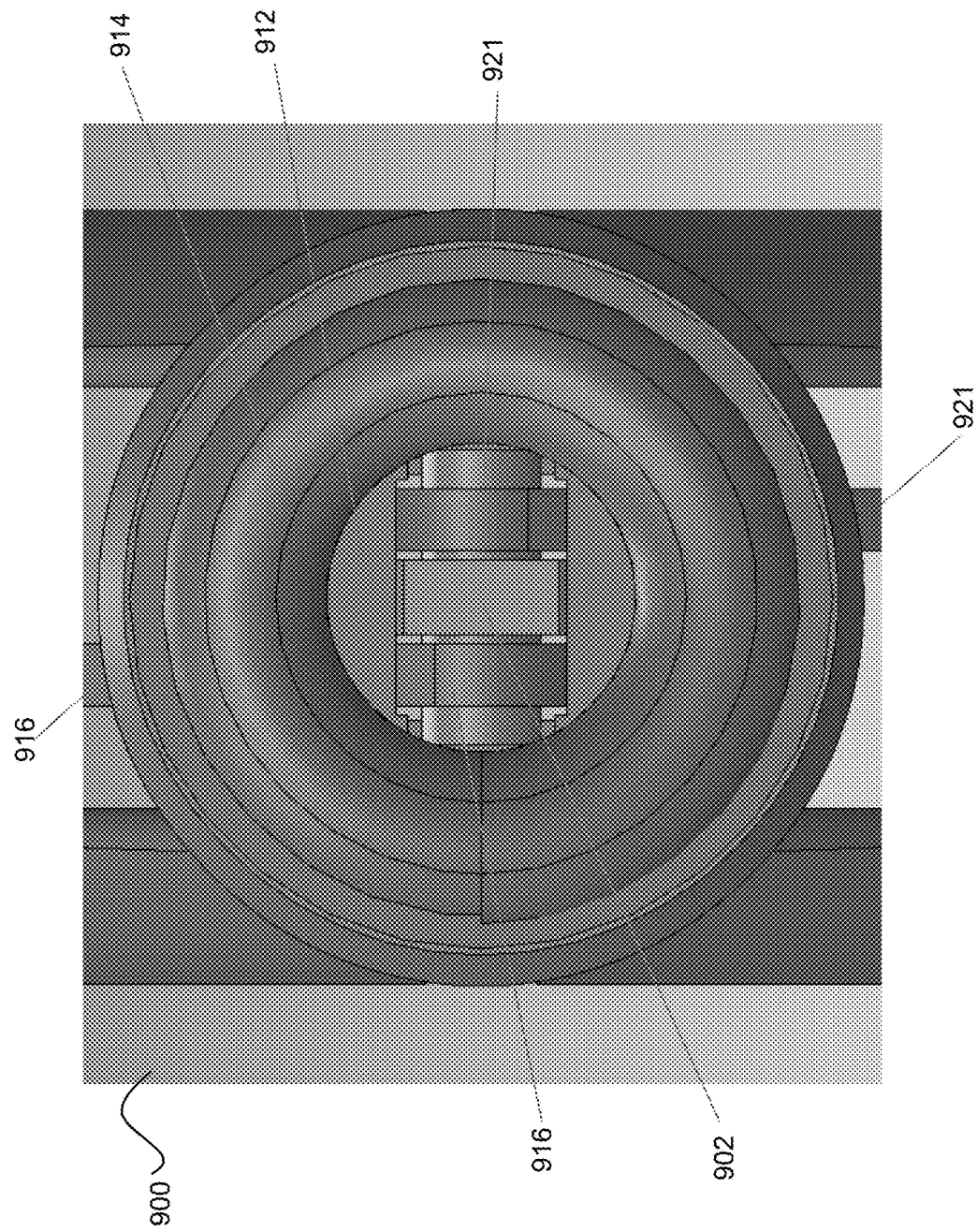
FIG. 9T illustrates a close up of rear view shown in FIG. 9S of the embodiment of the biopsy forceps of FIG. 9A in an open position.

FIG. 9T illustrates a close up of rear view shown in FIG. 9N of the embodiment of the biopsy forceps 900 of FIG. 9A in an open position. As can be seen in the figure, needle drive 902 passes through spring wire jacket 914 and clevis 912. In the rear view illustrated in FIG. 9T, proximal portions of linkages 916, 921 are connected to, and positioned on a left side and a right side of, the needle drive 902 respectively. The needle drive wire 902 extends longitudinally within spring wire jacket 914 along the length of the forceps 900 and is connected to linkage 916 between the distal protrusions of the clevis at its distal end and is connected to an actuator or handle at its proximal end. The needle drive wire 902 is also connected to linkage 921 between the distal protrusions of the clevis at its distal.

Referring to FIGS. 9A through 9T, longitudinal movement of the needle drive wire 902 within the spring wire jacket 914 is translated, at linkage pivot points positioned on the distal end of said needle drive wire 902, to up and down movement of linkage 916 and linkage 921 at the distal end of the forceps 900. This up and down movement of the linkages 916, 921 causes the jaws 904, 908 to open and close. For example, in one embodiment, an operator pushes in on a handle at the proximal end of the forceps 900. This pushing motion results in longitudinal distal motion of the needle drive wire 902 within the spring wire jacket 914. At a junction point 920 connecting the first linkage 916 and second linkage 921 to the distal end of the needle drive wire 902, the distal motion causes a pivoting of each linkage 916, 921 such that a distal end of linkage 916 extends upward and a distal end of linkage 921 extends downward. As the distal ends of each linkage 916, 921 are directly coupled to jaws 904, 908 via pins 906, 910, upward movement of the distal end of linkage 916 causes upward movement of the distal end of jaw 904 and downward movement of linkage 921 causes downward movement of jaw 908 to open the jaws.

To close the jaws 904, 908, an operator pulls back on the forceps 900 handle, causing longitudinal movement of the needle drive wire 902 in a proximal direction within the spring wire jacket 914. At a junction point 920 connecting the first linkage 916 and the second linkage 921 to the distal end of the needle drive wire 902, the proximal motion causes pivoting of each linkage 916, 921 such that a distal end of linkage 916 extends downward and a distal end of linkage 921 extends upward. Downward movement of the distal end of linkage 916 results in downward movement of the distal end of the first jaw 904 relative to pivot points 904a, 904b on the left protrusion 924 and right protrusion 926 respectively, of the clevis 912. Upward movement of the distal end of linkage 940 results in upward movement of the distal end of the second jaw 908 relative to pivot points 908a, 908b on the left protrusion 924 and right protrusion 926 respectively, of the clevis.

Figure 10A:
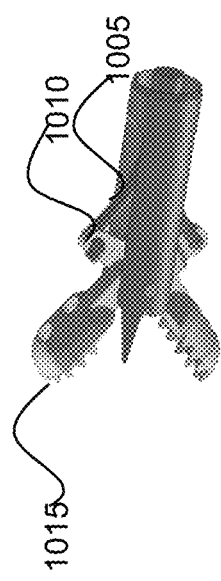
FIG. 10A is a design for attaching a guide wire to a tang on a jaws portion of a forceps portion of a biopsy tool, according to one embodiment of the present specification.
Figure 10B:
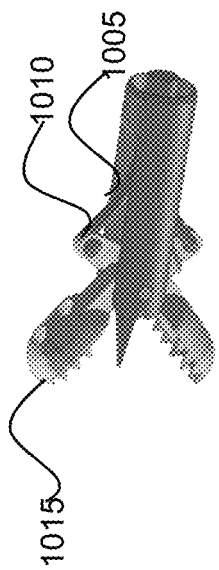
FIG. 10B is a design for attaching a guide wire to a tang on a jaws portion of a forceps portion of a biopsy tool, according to another embodiment of the present specification.

The present specification also describes improved tangs and drive wires for current design biopsy forceps and for the biopsy forceps devices described above. Thus, a new means for attaching the jaws to at least one drive wire, or for attaching the linkages (tangs) to the drive wire of the present forceps devices, is disclosed. As shown in FIG. 10A, conventional designs employ a single wire 1005 that is bent forward through an opening in the tang 1010 of the jaw 1015. As shown in FIG. 10B, in another conventional configuration, the wire 1005 is inserted through the opening in the tang 1010 of the jaw 1015 and then peened onto the jaw to prevent separation.

Figure 11B:
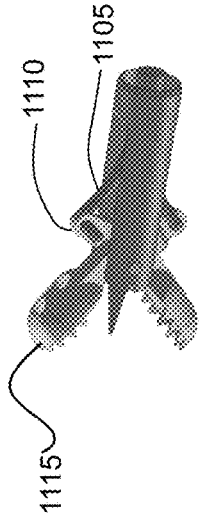
FIG. 11B is an illustration of a mechanism for attaching a guide wire to a tang on a jaws portion of a forceps portion of a biopsy tool in another embodiment of the present specification.
Figure 11A:
FIG. 11A is an illustration of a mechanism for attaching a guide wire to a tang on a jaws portion of a forceps portion of a biopsy tool in one embodiment of the present specification.

As shown in FIG. 11A, in some embodiments of the present specification, the wire is passed through the opening in the tang, or linkage of jaw 1115 and then looped in a 180 degree looped configuration.

As shown in FIG. 11B, in some embodiments of the present specification, the wire is passed through the opening in the tang, or linkage of the jaw 1115 and then bent in a 90 degree bent orientation.

Figure 11E:
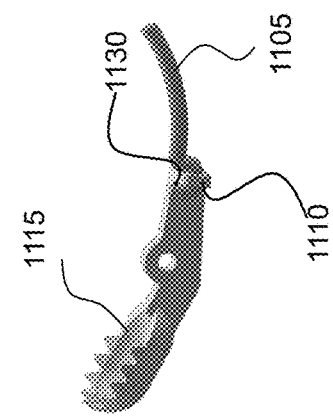
FIG. 11E is an illustration of a mechanism for attaching a guide wire to a tang on a jaws portion of a forceps portion of a biopsy tool in yet another embodiment of the present specification.
Figure 11D:
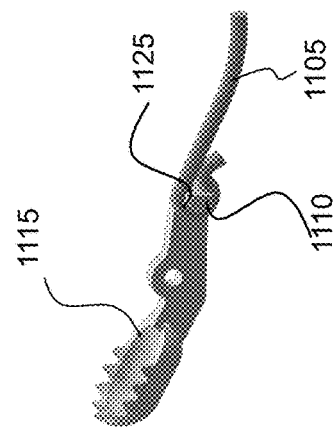
FIG. 11D is an illustration of a mechanism for attaching a guide wire to a tang on a jaws portion of a forceps portion of a biopsy tool in another embodiment of the present specification.
Figure 11C:
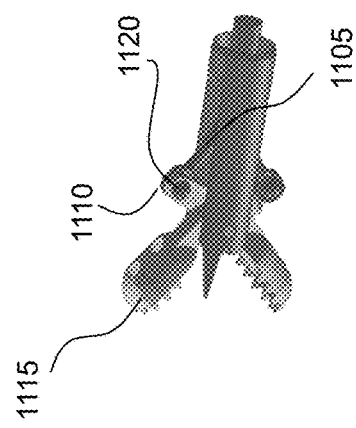
FIG. 11C is an illustration of a mechanism for attaching a guide wire to a tang on a jaws portion of a forceps portion of a biopsy tool in another embodiment of the present specification.

As shown in FIG. 11C, in some embodiments, a rivet 1120 is used as a separate attachment mechanism to secure the drive wire to the tang, or linkage of the jaws 1115 after passing said wire 1105 through an opening in said tang 1110.

As shown in FIG. 11D, in some embodiments, a clip mechanism 1125 is used to secure the drive wire to the tang, or linkage of the jaws 1115. The drive wire 1105 is wrapped about a peg on the tang 1110 and bent into a clip 1125 configuration. As shown in FIG. 11E, in some embodiments, a hook mechanism 1130 is used to secure the drive wire 1105 to the tang, or linkage of the jaws 1115. The drive wire 1105 is hooked about a peg on the tang 1110 and bent into a hook 1130 configuration. With respect to FIGS. 11D and 11E, the tang 1110 is modified to allow for such attachments with the drive wire.

Thus, the drive wire and tang connection mechanism of the present specification allows for improved manufacturability and reliability of the connection between the jaw and the drive wire.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A biopsy device for use with an endoscope, the biopsy device comprising:
   a control handle and a drive wire, wherein the control handle is configured to manipulate said drive wire;
   an elongate tubular portion having a proximal end and a distal end;
   wherein the control handle is connected to the elongate tubular portion at the proximal end of said elongate tubular portion, and wherein the drive wire extends from the control handle, through the elongate tubular portion, and to the distal end of said elongate tubular portion, and
   wherein at said distal end of said elongate tubular portion, the drive wire is coupled to a first linkage, a second linkage, and a needle, wherein a first pivot point is attached to said first linkage and a second pivot point is attached to said second linkage, and wherein said first pivot point and said second pivot point are positioned at a same longitudinal distance along a length of said drive wire;

a first jaw and a second jaw, wherein said first jaw comprises a first plurality of teeth at a distal end of said first jaw, and a first opening at a proximal end of said first jaw, and wherein said second jaw comprises a second plurality of teeth at a distal end of said second jaw, and a second opening at a proximal end of said second jaw; and a coupling unit having a first end and a second end, wherein, at said first end, the coupling unit is attached to said distal end of the elongate tubular portion and wherein, at said second end, the coupling unit comprises:

a third pivot point attached to the first jaw and a fourth pivot point attached to the second jaw, wherein the third pivot point and fourth pivot point are positioned at a same longitudinal distance along a length of the coupling unit, are offset from each other, and are positioned proximal to the first pivot point and second pivot point;

wherein the first jaw is coupled to the first linkage by a first pin attached to the first linkage and configured to rotate within said first opening, and wherein the second jaw is coupled to the second linkage by a second pin attached to the second linkage and configured to rotate within said second opening.

2. The biopsy device of claim 1, operable between a closed configuration and an open configuration, and wherein, when in said closed configuration, said first plurality of teeth and said second plurality of teeth are aligned so that teeth of the first plurality of teeth are positioned between teeth of the second plurality of teeth, and teeth of the second plurality of teeth are positioned between teeth of the first plurality of teeth.

3. The biopsy device of claim 2 wherein said device has a minimum cut depth in a range of 2 mm to 3 mm with a maximum cut width in a range of 10 mm to 13 mm.

4. The biopsy device of claim 1, wherein the distal face of at least one of said jaws is squared off.

5. The biopsy device of claim 1, wherein distal movement of the drive wire via said control handle causes said needle to move distally for piercing tissue.

6. The biopsy device of claim 1, wherein said jaws have a maximum opening angle in a range of 80 degrees to 100 degrees.

7. The biopsy device of claim 1, wherein a length of each jaw is in a range of 8 mm to 9 mm.

8. The biopsy device of claim 1, further comprising at least one clip attached to said first pin and at least one clip attached to said second pin, wherein said clips maintain proper positioning of said pins within said openings.

9. The biopsy device of claim 1, wherein said first jaw further comprises a third opening at the proximal end of the first jaw, and said second jaw further comprises a fourth opening at the proximal end of the second jaw, and wherein said first pin is configured to rotate within said first opening and said third opening and said second pin is configured to rotate within said second opening and said fourth opening.

10. The biopsy device of claim 1, wherein, with the jaws in an open configuration, a width of said jaws is greater than a height of said jaws to provide a wider bite.

11. A biopsy device for use with an endoscope, the biopsy device comprising:

a control handle and a drive wire, wherein the control handle is configured to manipulate said drive wire;

an elongate tubular portion having a proximal end and a distal end, wherein the control handle is connected to the elongate tubular portion at the proximal end of said elongate tubular portion, and wherein the drive wire extends from the control handle, through the elongate tubular portion, and to the distal end of said elongate tubular portion, wherein at said distal end of said elongate tubular portion, the drive wire is coupled to a first linkage, a second linkage, and a needle, wherein a first pivot point is attached to said first linkage and a second pivot point is attached to said second linkage, and wherein said first pivot point and said second pivot point are positioned at a same longitudinal distance along a length of said drive wire;

a first jaw and a second jaw, wherein said first jaw comprises a first plurality of teeth at a distal end of said first jaw, and a first opening at a proximal end of said first jaw, and wherein said second jaw comprises a second plurality of teeth at a distal end of said second jaw, and a second opening at a proximal end of said second jaw;

a coupling unit having a first end and a second end, wherein, at said first end, the coupling unit is attached to said distal end of the tubular portion, and wherein, at said second end, the coupling unit comprises:

a third pivot point attached to the first jaw and a fourth pivot point attached to the second jaw, wherein the third pivot point and fourth pivot point are positioned at a same longitudinal distance along a length of the coupling unit, are laterally offset from each other, and are positioned proximal to said first pivot point and second pivot point;

wherein the first jaw is coupled to the first linkage by a first pin attached to the first linkage and configured to rotate within said first opening, and wherein the second jaw is coupled to the second linkage by a second pin attached to the second linkage and configured to rotate within said second opening; and wherein said first linkage includes a first component for attaching said drive wire and said second linkage includes a second component for attaching said drive wire.

12. The biopsy device of claim 11, wherein said first and second components comprise openings, and said drive wire is passed through said openings and looped about, bent over, or riveted to said linkages.

13. The biopsy device of claim 11, wherein said first and second components comprise pegs, and said drive wire is clipped or hooked about said pegs.

* * * * *